United States Patent [19]
Shimura et al.

[11] Patent Number: 5,359,080
[45] Date of Patent: Oct. 25, 1994

[54] YELLOW DYE-FORMING COUPLER AND SILVER HALIDE COLOR PHOTOGRAPHIC MATERIAL CONTAINING SAME

[75] Inventors: Yoshio Shimura; Hidetoshi Kobayashi; Yasuhiro Yoshioka, all of Minami-ashigara, Japan

[73] Assignee: Fuji Photo Film Co., Ltd., Kanagawa, Japan

[21] Appl. No.: 17,447

[22] Filed: Feb. 12, 1993

Related U.S. Application Data

[63] Continuation of Ser. No. 670,277, Mar. 15, 1991, abandoned.

[30] Foreign Application Priority Data

Mar. 15, 1990 [JP] Japan .................. 2-64718

[51] Int. Cl.$^5$ .................. C07D 233/78; C07C 233/14; C07C 311/08
[52] U.S. Cl. .................. 548/317.5; 560/13; 564/158; 548/227; 548/263.4; 548/267.6; 548/138; 548/257; 548/251; 548/163; 549/488; 544/132; 544/324
[58] Field of Search .................. 548/317.5; 560/13; 564/158

[56] References Cited

U.S. PATENT DOCUMENTS

| | | | |
|---|---|---|---|
| Re. 27,848 | 12/1973 | Weissberger | 548/311 |
| 3,644,498 | 2/1972 | Loria | 560/13 |
| 4,146,396 | 3/1979 | Yokota et al. | 548/311 |
| 4,268,591 | 5/1981 | Tschopp | 430/17 |
| 4,289,847 | 9/1981 | Ishikawa et al. | 430/557 |
| 4,404,274 | 9/1983 | Arai et al. | 430/389 |
| 5,145,997 | 9/1992 | Schwartz et al. | 564/158 |

FOREIGN PATENT DOCUMENTS

2213461 11/1972 Fed. Rep. of Germany .
0161543 12/1981 Japan .
0164343 12/1981 Japan .

OTHER PUBLICATIONS

Chemical Abstracts, vol. 115, No. 3, Abstracts 22252 and 22253 (1991).

*Primary Examiner*—Joseph Paul Brust
*Assistant Examiner*—Mary Susan H. Gabilan
*Attorney, Agent, or Firm*—Birch, Stewart, Kolasch & Birch

[57] ABSTRACT

There is disclosed an acylacetamide-type yellow coupler having an acyl group represented by formula (I) and a silver halide color photographic material containing same.

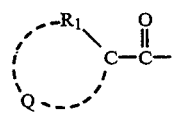

Formula (I)

wherein $R_1$ represents a monovalent group, Q represents a group of non-metallic atoms required to form together with the C a substituted or unsubstituted 3- to 5-membered cyclic hydrocarbon group or a substituted or unsubstituted 3- to 5-membered heterocyclic group having in the group at least one hetero atom selected from a group consisting of N, O, S, and P, provided that $R_1$ is not a hydrogen atom and does not bond to Q to form a ring.

39 Claims, 2 Drawing Sheets

YELLOW DYE-FORMING COUPLER AND SILVER HALIDE COLOR PHOTOGRAPHIC MATERIAL CONTAINING SAME

This application is a continuation of application Ser. No. 07/670,277 filed on Mar. 15, 1991, now abandoned.

FIELD OF THE INVENTION

The present invention relates to novel acylacetamide-type yellow dye-forming couplers and silver halide color photographic materials containing the same.

BACKGROUND OF THE INVENTION

In a silver halide color photographic material, a color image is formed when the material is exposed to light and then is subjected to color development so that an oxidized aromatic primary amine color developer and a dye-forming coupler (hereinafter referred to as coupler) may interact.

Generally, in such a process, the color reproduction method employed is a subtractive color process wherein to reproduce blue, green and red, a yellow color image, a magenta color image, and a cyan color image respectively complementary thereto are formed. To form a yellow color image, generally acylacetamide couplers and malondianilide couplers are used as a yellow dye-forming coupler (hereinafter referred to as yellow coupler); to form a magenta color image, generally, for example, 5-pyrazolone couplers and pyrazolotriazole couplers are used as a magenta coupler; and to form a cyan color image, generally phenol couplers and naphtol couplers are used as a cyan coupler.

Yellow dyes, magenta dyes, and cyan dyes obtained from these couplers are generally formed in silver halide emulsion layers or layers adjacent thereto having color sensitivities to radiations respectively complementary to the radiations that are absorbed by them.

As yellow couplers, particularly for forming images, acylacetamide couplers, represented by benzoylacetanilide couplers and pivaloylacetanilide couplers, are generally used. Since the former are generally high in coupling activity with the oxidized products of aromatic primary amine developers at the time of development and the yellow dyes formed are high in the molar extinction coefficient, they are used mainly in photographing color photographic materials that require a high sensitivity, particularly color negative films. On the other hand, the latter are excellent in the spectral absorption characteristics and fastness of the yellow dye and are mainly used in color papers and color reversal films.

However, although benzoylacetanilide-type couplers are high in coupling reactivity with the oxidized products of aromatic primary amine developers at the time of color development and they are great in the molar extinction coefficient of the yellow azomethine dye formed, they have a defect that they are poor in spectral absorption characteristics for the yellow image. Likewise, while pivaloylacetanilide-type couplers are excellent in the spectral absorption characteristics for the yellow image formed, they have defects in that their coupling reactivity with the oxidized products of aromatic primary amine developers at the time of color development is low and the molar extinction coefficient of the yellow azomethine dyes formed is small.

A high coupling reactivity of a coupler and a high molar extinction coefficient of a dye formed therewith make possible a high sensitivity, a high gamma value and a high color density, and bring about what is called a high color-forming property. Additionally, excellent spectral absorption characteristics in a yellow color image implies absorption characteristics such that, for example, the sharpness of the spectral absorption-curve on the long wavelength side is good and undesirable absorption in the green region is minimal.

Therefore, it is desired to develop yellow couplers having the advantages of both benzoylacetanilide-type and pivaloylacetanilide-type couplers, i.e., a high color-forming property (high coupling reactivity of the coupler and the high molar absorption coefficient of the dye) and spectral absorption characteristics which are excellent in the color image.

As acyl groups of acylacetamide-type couplers, for example, a pivaloyl group, a 7,7-dimethylnorbornane-1-carbonyl group, and a 1-methylcyclohexane-1-carbonyl group are disclosed in U.S. Pat. No. Re. 27,848 and, for example, a cyclopropane-1-carbonyl group and a cyclohexane-1-carbonyl group are disclosed in JP-A ("JP-A" means unexamined published Japanese patent application) No. 26133/1972. However, these couplers are poor in some points; for example, their coupling reactivity is poor, the molar extinction coefficient of the dyes is small, or the spectral absorption characteristics of the color images is poor.

A higher sensitivity, higher image quality, and higher toughness have been earnestly desired in recently developed photographic materials. Therefore, the development of couplers excellent in color-forming property and spectral absorption characteristics of the color image has been strongly pursued. However, prior yellow couplers including those disclosed in the above two patents, have had difficulty in satisfying all these requirements.

SUMMARY OF THE INVENTION

Therefore, the first object of the present invention is to provide a yellow coupler excellent in color-forming property and a silver halide color photographic material containing the same.

The second object of the present invention is to provide a yellow coupler excellent in the spectral absorption characteristics for the yellow color image produced by color development and a silver halide color photographic material containing the same.

Other and further objects, features, and advantages of the invention will appear more evident from the following description taken in connection with the accompanying drawing.

DETAILED DESCRIPTION OF THE INVENTION

Figure 1:
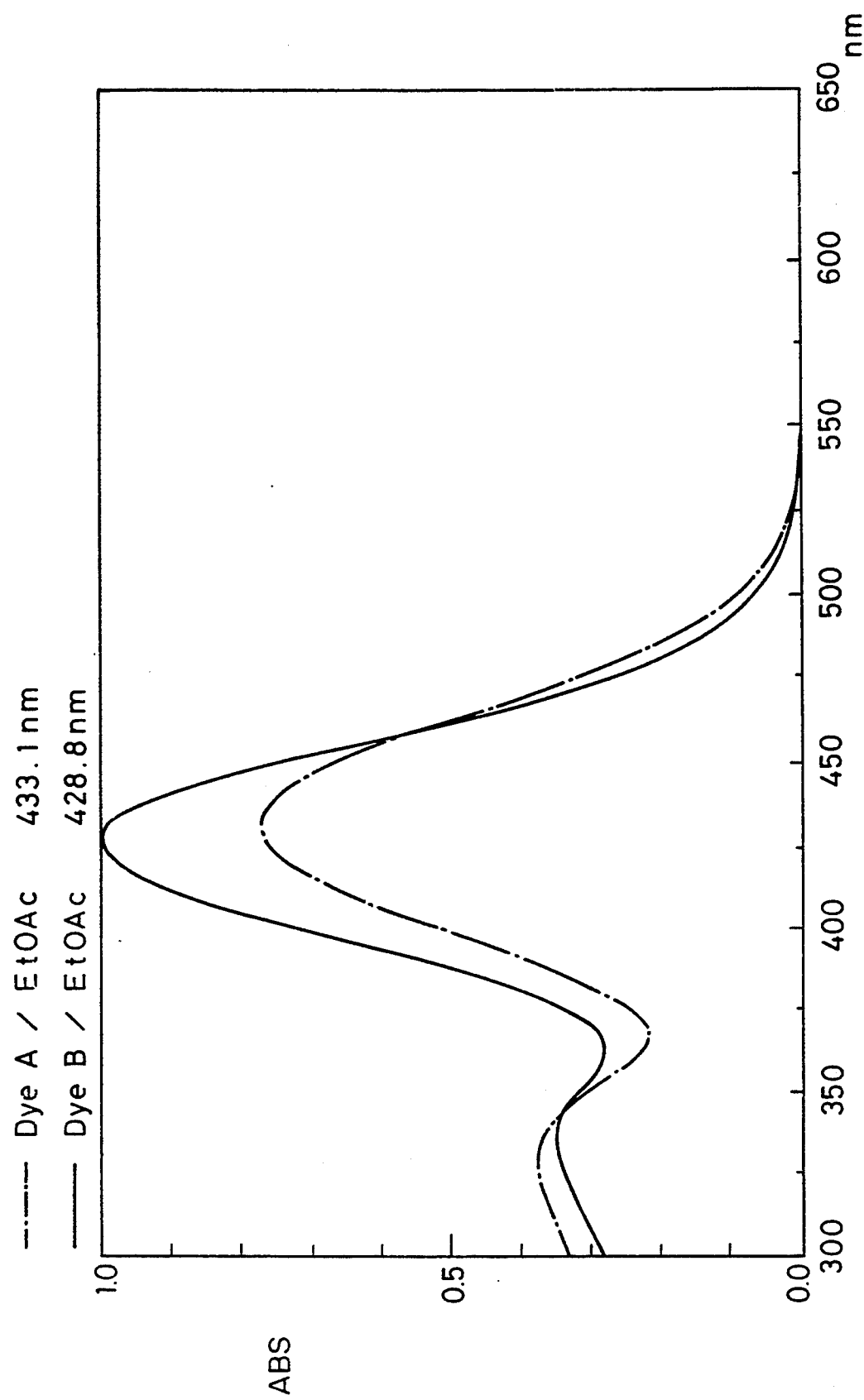
FIG. 1 is a diagram of the absorption spectra of dyes, wherein the absorbence is plotted along the ordinate and the absorption wave length (nm) is plotted along the abscissa.

The above objects are attained by providing the following yellow coupler (1) and silver halide color photographic material (2):

(1) An acylacetamide-type yellow dye-forming coupler wherein the acyl group is represented by the following formula (I):

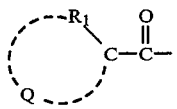

Formula (I)

wherein $R_1$ represents a monovalent group, Q represents a group of non-metallic atoms required to form together with the C a 3- to 5-membered cyclic hydrocarbon group or a 3- to 5-membered heterocyclic group having in the group at least one hereto atom selected from a group consisting of N, O, S, and P, provided that $R_1$ is not a hydrogen atom and does not bond to Q to form a ring.

(2) A silver halide color photographic material having on a base at least one silver halide emulsion layer containing yellow dye-forming couplers, wherein at least one of said yellow dye-forming couplers is a yellow dye-forming coupler described in item (1).

The acylacetamide-type yellow couplers of the present invention will now be described in more detail.

The acylacetamide-type yellow couplers of the present invention are preferably represented by the following formula (II):

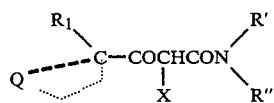

Formula (II)

In formula (II), $R_1$ and Q are the same as $R_1$ and Q in formula (I), respectively, x represents a hydrogen atom or a group capable of being released upon a coupling reaction thereof with the oxidized product of an aromatic primary amine developing agent (hereinafter referred to as coupling split-off group), and R' and R" each independently represent a hydrogen atom, an alkyl group, an aryl group or a heterocyclic group, wherein R' and R" may be combined together to form a ring with N.

Further, the acylacetamide-type yellow couplers of the present invention are preferably represented by the following formula (Y):

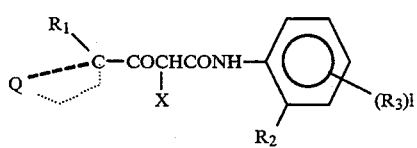

Formula (Y)

In formula (Y), $R_1$ represents a monovalent substituent other than hydrogen; Q represents a group of non-metallic atoms required to form together with the C, a substituted or unsubstituted 3- to 5-membered cyclic hydrocarbon group or a substituted or unsubstituted 3- to 5-membered heterocyclic group having in the group at least one hetero atom selected from a group consisting of N, O, S, and P; $R_2$ represents a hydrogen atom, a halogen atom (e.g., F, Cl, Br, and I, which is applied hereinafter to the description of formula (Y)), an alkoxy group, an aryloxy group, an alkyl group, an amino group or, cyclopentyl, cyclohexyl, allyl, 3-cyclohexenyl, oleyl, benzyl, trifluoromethyl, hydroxymethylmethoxyethyl, ethoxycarbonylmethyl or phenoxyethyl; $R_3$ represents a group capable of substitution onto a benzene ring; X has the same meaning as in formula (II); l is an integer of 0 to 4, and when l is 2 or more, the $R_3$ groups may be the same or different.

When any of the substituents in formula (Y) is an alkyl group or contains an alkyl group, unless otherwise specified the alkyl group is a straight-chain or branched chain or cyclic alkyl group that may be substituted and may contain an unsaturated bond such as methyl, isopropyl, t-butyl, t-pentyl, 2-ethylhexyl, 1,1,3,3-tetramethylbutyl, dodecyl, and hexadecyl. The substituents may also be selected from the group consisting of cyclopentyl, cyclohexyl, allyl, 3-cyclohexenyl, oleyl, benzyl, trifluoromethyl, hydroxymethylmethoxyethyl, ethoxycarbonylmethyl, and phenoxyethyl. Moreover, unless otherwise specified the alkyl group contains 1 to 30 carbon atoms (exclusive of any substituents).

When any of the substituent in formula (Y) is an aryl group or contains an aryl group, unless otherwise specified the aryl group is a monocyclic or condensed ring aryl group containing 3 to 8 ring members selected from the group consisting of carbon, oxygen, nitrogen and sulfur. The aryl groups may be further substituted and include aryl groups such as phenyl, 1-naphthyl, p-tolyl, o-tolyl, p-chlorophenyl, 4-methoxyphenyl, 8-quinolyl, 4-hexadecyloxyphenyl, pentafluorophenyl, p-hydroxyphenyl, p-cyanophenyl, 3-pentadecylphenyl, 2,4-di-t-pentylphenyl, p-methanesulfonamidophenyl, and 3,4-dichlorophenyl.

When the substituent in formula (Y) is a heterocyclic group or contains a heterocyclic ring, unless otherwise specified the heterocyclic ring group is a 3- to 8-membered monocyclic or condensed ring heterocyclic group that contains at least one hetero atom selected from the group consisting of O, N, S, P, Se, and Te, and contains from 2 to 36 carbon atoms and may be substituted such as 2-furyl, 2-pyridyl, 4-pyridyl, 1-pyrazolyl, 1-imidazolyl, 1-benzotriazolyl, 2-benzotriazolyl, succinimido, phthalimido, and 1-benzyl-2,4-imidazolidinedione-3-yl.

Substituents preferably used in formula (Y) will now be described below.

$R_1$ in formula (Y) preferably represents a halogen atom, a cyano group, a monovalent aliphatic-type group that may be substituted and has a total number of carbon atoms (hereinafter, abbreviated as C-number) of 1 to 30 such as an alkyl group and an alkoxy group, or a monovalent aryl-type group that may be substituted and has a total C-number of 6 to 30 such as an aryl group and an aryloxy group, and examples of substituents therefor are a halogen atom, an alkyl group (straight, branched or cyclic), an alkoxy group, a nitro group, an amino group, a carbonamido group, a sulfonamido group, and an acyl group.

Preferably Q in formula (Y) represents a group of non-metallic atoms which forms together with the C (carbon atom), a substituted or unsubstituted 3- to 5-membered hydrocarbon ring having a total C-number of 3 to 30, or a 3 substituted or unsubstituted, 3- to 5-membered heterocyclic ring moiety having a total C-number of 2 to 30 and having in the ring at least one hereto atom selected from the group consisting of N, O, S, and P, and preferably containing from 1 to 3 hetero atom ring members. The ring formed by Q together with the C may have an unsaturated bond in the ring. As examples of the ring formed by Q together with the C are a cyclopropane ring, a cyclobutane ring, a cyclopentane ring, a cyclopropene ring, a cyclobutene ring, a cyclopentene ring, an oxetane ring, an oxolane ring, a 1,3-dioxolane ring, a thiethane ring, a thiolane ring, and a pyrrolidine ring. Examples of substituent for the rings include a halogen atom, a hydroxyl group, an alkyl group, an aryl group, an acyl group, an alkoxy group, an aryloxy group, a cyano group, an alkoxycarbonyl group, an alkylthio group, and an arylthio group.

$R_2$ in formula (Y) preferably represents a halogen atom, an alkoxy group that may be substituted and has a total C-number of 1 to 30, an aryloxy group that may be substituted and has a total C-number of 6 to 30, an alkyl group that may be substituted and has a total C-number of 1 to 30, or an amino group that may be substituted and has a total C-number of 0 to 30 and the substituent is, for example, a halogen atom, an alkyl group, an alkoxy group, or an aryloxy group.

Preferably, $R_3$ in formula (Y) is a halogen atom, an alkyl group (as defined above), an aryl group (as defined above), an alkoxy group, an aryloxy group, an alkoxycarbonyl group, an aryloxycarbonyl group, a carbonamido group, a sulfonamido group, a carbamoyl group, a sulfamoyl group, an alkylsulfonyl group, a arylsulfonyl group, a ureido group, a sulfamoylamino group, an alkoxycarbonylamino group, an alkoxysulfonyl group, a nitro group, a heterocyclic group (as defined above), a cyano group, an acyl group, an acyloxy group, an alkylsulfonyloxy group, and an arylsulfonyloxy group, and examples of the coupling split-off group are a heterocyclic group (as defined above) bonded to the coupling active site through the nitrogen atom, an aryloxy group, an arylthio group, an acyloxy group, an alkylsulfonyloxy group, an arylsulfonyloxy group, a heterocyclic oxy group (wherein heterocyclic is as defined above), and a halogen atom.

$R_3$ in formula (Y) preferably represents a halogen atom, an alkyl group that may be substituted and has a total C-number of 1 to 30, more preferably 1 to 18, an aryl group that may be substituted and has a total C-number of 6 to 30, more preferably 6 to 24, an alkoxy group that may be substituted and has a total C-number of 1 to 30, more preferably 1 to 18, an aryloxy group that may be substituted and has a total C-number 6 to 30, more preferably 6 to 24, an alkoxycarbonyl group that may be substituted and has a total C-number of 2 to 30, more preferably 2 to 19, an aryloxycarbonyl group that may be substituted and has a total C-number of 7 to 30, more preferably 7 to 24, a carbonamido group that may be substituted and has a total C-number of 1 to 30, more preferably 1 to 20, a sulfonamido group that may be substituted and has a total C-number of 1 to 30, more preferably 1 to 24, a carbamoyl group that may be substituted and has a total C-number of 1 to 30, more preferably 1 to 20, a sulfamoyl group that may be substituted and has a total C-number of 0 to 30, more preferably 1 to 24, an alkylsulfonyl group that may be substituted and has a total C-number of 1 to 30, more preferably 1 to 20, an arylsulfonyl group that may be substituted and has a total C-number of 6 to 30, more preferably 6 to 24, a ureido group that may be substituted and has a total C-number of 1 to 30, more preferably 1 to 20, a sulfamoylamino group that may be substituted and has a total C-number of 0 to 30, preferably 0 to 20, an alkoxycarbonylamino group that may be substituted and has a total C-number of 2 to 30, preferably 2 to 20, a heterocyclic group (as defined above) that may be substituted and has a total C-number of 1 to 30, preferably 1 to 20, an acyl group that may be substituted and has a total C-number of 1 to 30, preferably 1 to 20, an alkylsulfonyloxy group that may be substituted and has a total C-number of 1 to 30, preferably 1 to 20, or an arylsulfonyloxy group that may be substituted and has a total C-number of 6 to 30, preferably 6 to 24; and examples of the substituents for these $R_3$ moieties include a halogen atom, an alkyl group, an aryl group, a heterocyclic group (as defined above), an alkoxy group, an aryloxy group, a heterocyclic oxy group (wherein heterocyclic is as defined above), an alkylthio group, an arylthio group, a heterocyclic thio group (wherein heterocyclic is as defined above), an alkylsulfonyl group, an arylsulfonyl group, an acyl group, a carbonamido group, a sulfonamido group, a carbamoyl group, a sulfamoyl group, an alkoxycarbonylamino group, a sulfamoylamino group, a ureido group, a cyano group, a nitro group, an acyloxy group, an alkoxycarbonyl group, an aryloxycarbonyl group, an alkylsulfonyloxy group, and an arylsulfonyloxy group.

In formula (Y), preferably l is an integer of 1 or 2 and the position of the substitution of $R_3$ is preferably the meta-position or ortho-position relative to

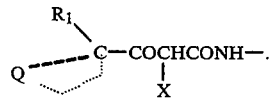

In formula (Y), preferably X represents a heterocyclic group (as defined above) bonded to the coupling active site through a nitrogen atom or an aryloxy group.

When X represents a heterocyclic group, X is most preferably a heterocyclic group (as defined above) comprising a 5- to 7-membered monocyclic group or condensed ring group that may be substituted. Exemplary of such groups are succinimido, maleinimido, phthalimido, diglycolimido, pyrrole, pyrazole, imidazole, 1,2,4-triazole, tetrazole, indole, indazole, benzimidazole, benztriazole, imidazolidin-2,4-dione, oxazolidin-2,4-dione, thiazolidin-2,4-dione, imidazolidin-2-one, oxazolidin-2-one, thiazolidin-2-one, benzimidazolin-2-one, benzoxazolidin-2-one, benzothiazolin-2-one, 2-pyrrolin-5-one, 2-imidazolin-5-one, indolin-2,3-dione, 2,6-dioxypurine, parabanic acid, 1,2,4-triazolidin-3,5-dione, 2-pyridone, 4-pyridone, 2-pyrimidone, 6-pyridazone-2-pyrazone, 2-amino-1,3,4-thiazolidine, 2-imino-1,3,4-thiazolidin-4-one and the like, any of which heterocyclic ring groups may be substituted. Examples of the substituent of these heterocyclic rings include a halogen atom, a hydroxyl group, a nitro group, a cyano group, a carboxyl group, a sulfo group, an alkyl group, an aryl group, an alkoxy group, an aryloxy group, an alkylthio group, an arylthio group, an alkylsulfonyl group, an arylsulfonyl group, an alkoxycarbonyl group, an aryloxycarbonyl group, an acyl group, an acyloxy group, an amino group, a carbonamido group, a sulfonamido group, a carbamoyl group, a sulfamoyl group, a ureido group, an alkoxycarbonylamino group, and a sulfamoylamino group. When X represents an aryloxy group, preferably X represents an aryloxy group having a total C-number of 6 to 30 which may be substituted by a substituent selected from the group consisting of the substituents mentioned above for the heterocyclic ring represented by X. Most preferably, the substituent of the aryloxy group is a halogen atom, a cyano group, a nitro group, a carboxyl group, a trifluoromethyl group, an alkoxycarbonyl group, a carbonamido group, a sulfonamido group, a carbamoyl group, a sulfamoyl group, an alkylsulfonyl group, an arylsulfonyl group, or a cyano group.

Particularly preferable substituents used in formula (Y) will now be described.

Particularly preferably $R_1$ is a halogen atom or an alkyl group (as defined above) and most preferably a methyl group.

Particularly preferably Q represents a group of non-metallic atoms required to form together with the C a 3- to 5- membered hydrocarbon ring, for example,

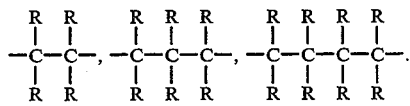

R represents a halogen atom, a hydrogen atom, or an alkyl group (as defined above). The groups R may be the same or different. Most preferably Q forms together with the C a 3-membered ring, that is, represented by

wherein R is as defined above.

Particularly preferably $R_2$ represents a chlorine atom, a fluorine atom, a substituted or unsubstituted alkyl group having a C-number of 1 to 6 (e.g., halogen substituted $C_{1-6}$ alkyl, methyl, trifluoromethyl, ethyl, isopropyl, and t-butyl) exclusive of its substituents, an alkoxy group having a C-number of 1 to 8 (e.g., methoxy, ethoxy, methoxyethoxy, and butoxy), or an aryloxy group having C-number of 6 to 24 (e.g., phenoxy, p-tolyloxy, and p-methoxyphenoxy); with a chlorine atom, a methoxy group, or a trifluoromethyl group most preferred.

Particularly preferably $R_3$ represents a halogen atom, an alkoxy group, an alkoxycarbonyl group, an aryloxycarbonyl group, a carbonamido group, a sulfonamido group, a carbamoyl group, or a sulfamoyl group, with an alkoxy group, an alkoxycarbonyl group, a carbonamido group, or a sulfonamido group most preferred.

Particularly preferably X is a group represented by the following formula (Y-1) or (Y-2): Formula (Y-1)

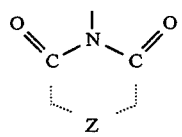

In formula (Y-1), Z represents

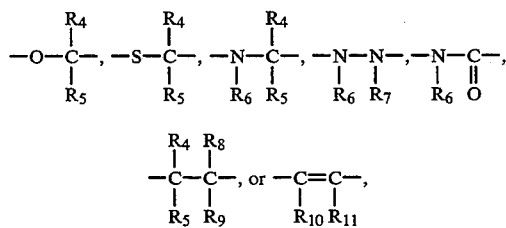

wherein $R_4$, $R_5$, $R_8$ and $R_9$, are the same or different, each represent a hydrogen atom, an alkyl group (as defined above), an aryl group (as defined above), an alkoxy group having C-number of 1 to 24, an aryloxy group having C-number of 6 to 24, an alkylthio group having C-number of 1 to 24, an arylthio group having C-number of 6 to 24, an alkylsulfonyl group having C-number of 1 to 24, an arylsulfonyl group having C-number of 6 to 24, or an amino group, any of which may be substituted (except hydrogen); $R_6$ and $R_7$ each represent a hydrogen atom, an alkyl group (as defined above), an aryl group (as defined above), an alkylsulfonyl group having C-number of 1 to 24, an arylsulfonyl group having C-number of 6 to 24, or an alkoxycarbonyl group having C-number of 1 to 24, any of which may be substituted (except hydrogen); $R_{10}$ and $R_{11}$ each represent a hydrogen atom, an alkyl group (as defined above), or an aryl group (as defined above), $R_{10}$ and $R_{11}$ may bond together to form a benzene ring, and $R_4$ and $R_5$, $R_5$ and $R_6$, $R_6$ and $R_7$, or $R_4$ and $R_8$ may bond together to form a 3 to 8 membered heterocyclic or hydrocarbon ring (e.g., cyclobutane, cyclohexane, cycloheptane, cyclohexene, pyrrolidine, and piperidine), any of which groups may be substituted (except hydrogen).

Among the heterocyclic groups represented by formula (Y-1), particularly preferable ones are heterocyclic groups wherein Z represent

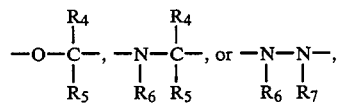

and $R_4$, $R_5$, $R_6$ and $R_7$, same or different are as defined above.

The total number of carbon atoms of the heterocyclic group represented by formula (Y-1) is 2 to 30, preferably 4 to 20, and more preferably 5 to 16.

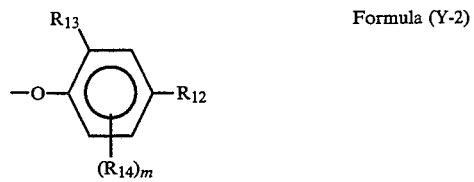

Formula (Y-2)

In formula (Y-2), at least one of $R_{12}$ and $R_{13}$ represents a group selected from a halogen atom, a cyano group, a nitro group, a trifluoromethyl, a carboxyl group, or one of the following groups, any of which may be substituted (except hydrogen), an alkoxycarbonyl group having C-number of 2 to 24, a carbonamido group having C-number of 1 to 247 a sulfonamido group having C-number of 1 to 24, a carbamoyl group having C-number of 1 to 24, a sulfamoyl group having C-number of 0 to 24, an alkylsulfonyl group having C-number of 1 to 24, an arylsulfonyl group having C-number of 6 to 24, and an acyl group having C-number of 1 to 24 and the other is a hydrogen atom, an alkyl group (as defined above), or an alkoxy group having C-number of 1 to 24; $R_{14}$ has the same meaning as that of $R_{12}$ or $R_{13}$; and m is an integer of 0 to 2. The total number of carbon atoms of the aryloxy group represented by formula (Y-2) is 6 to 30, preferably 6 to 24, and more preferably 6 to 15.

The coupler represented by formula (Y) may form a dimer or higher polymer formed by joining at the substituent $R_1$, X or through a bivalent or

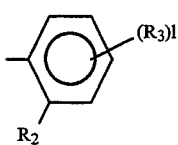
higher polyvalent group. In such cases, the carbon numbers thereof may fall outside the specified range defined for each substituent.
(1) Samples of the
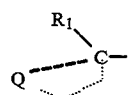
group formed by $R_1$ and Q with C are shown below.
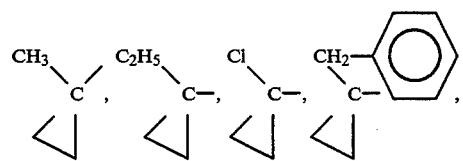
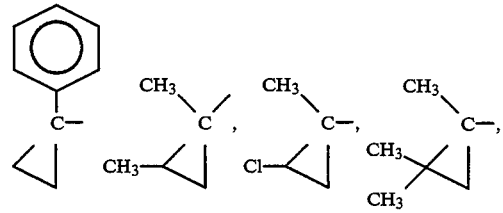
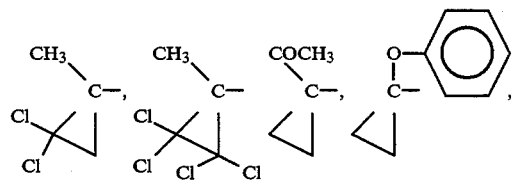
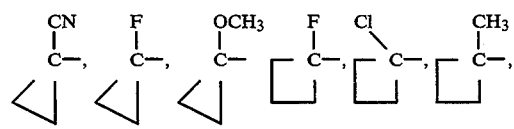
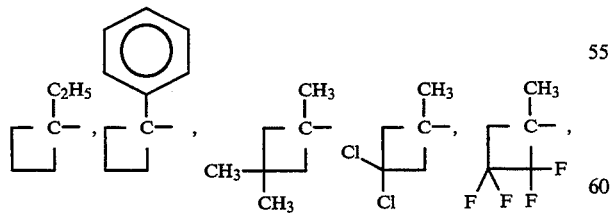
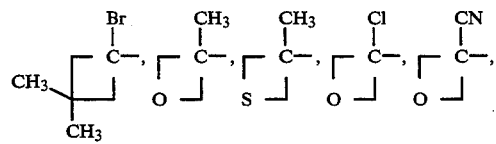
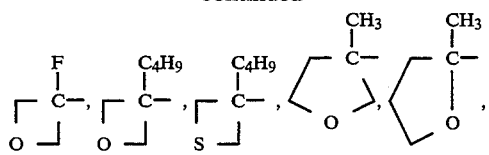
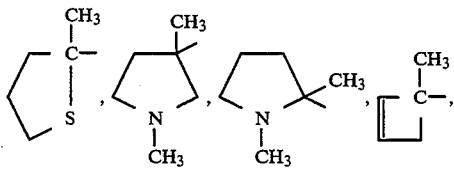
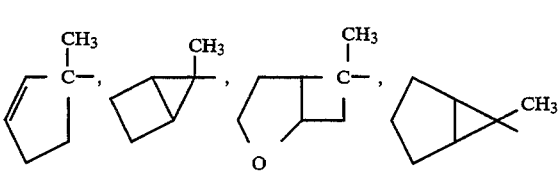
(2) Examples of $R_2$
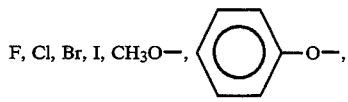
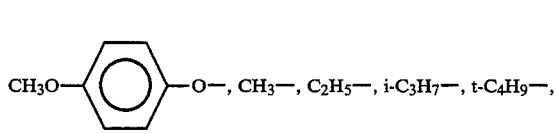
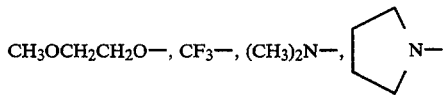
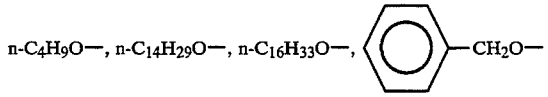
(3) Examples of $R_3$
F, Cl, Br, I, $CH_3O-$, $C_2H_5O-$, $n-C_{12}H_{25}O-$, $CH_3$, $t-C_4H_9-$,
$-COOCH_3$, $COOC_2H_5$, $-COOC_4H_9^{-n}$, $-COOC_{12}H_{25}^{-n}$,
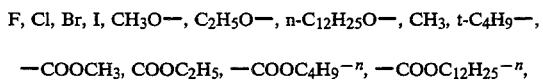
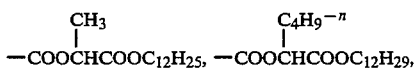
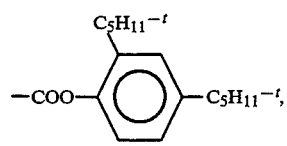
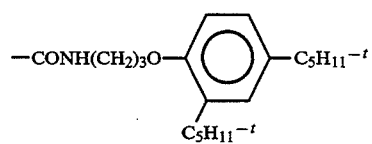

-continued
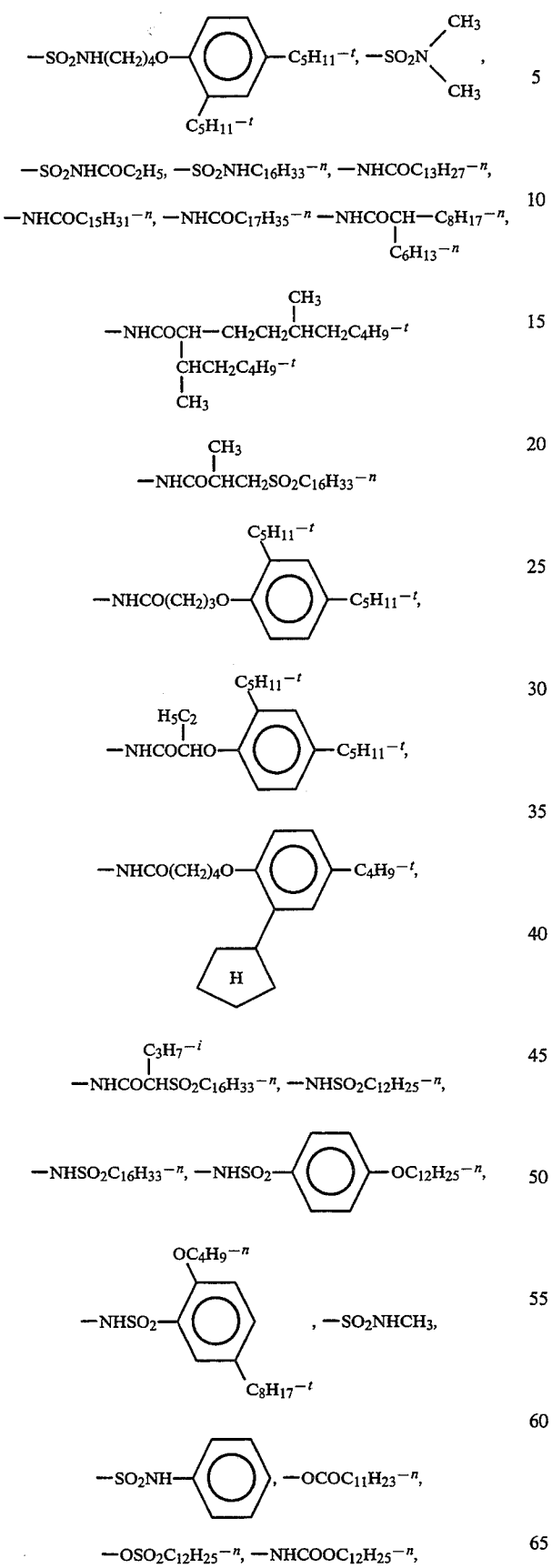
(4) Examples of X
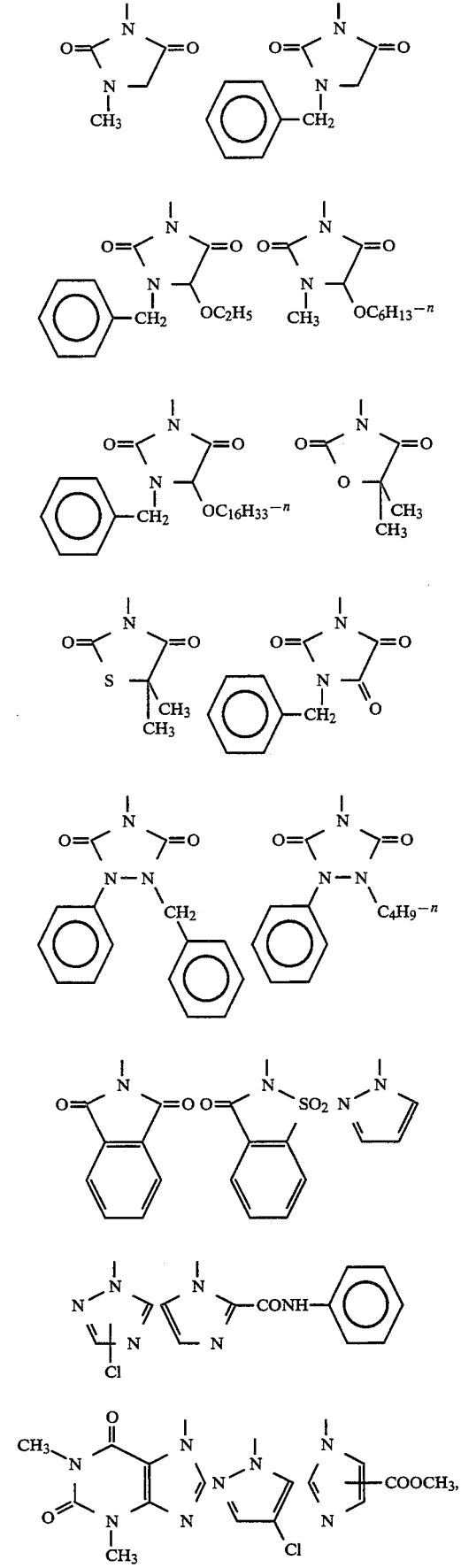

-continued
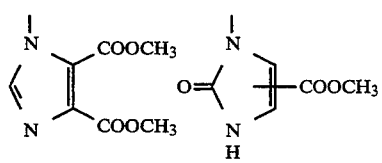
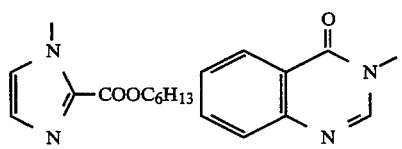
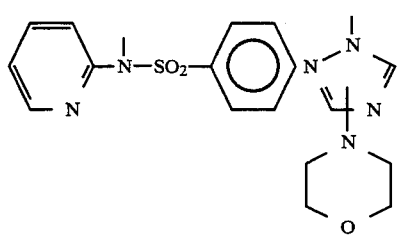
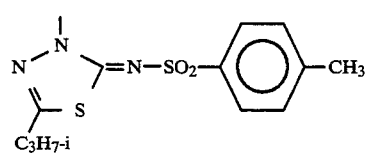
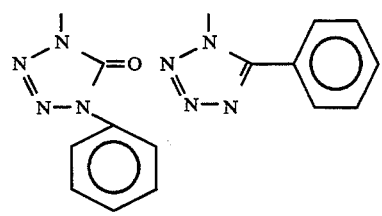
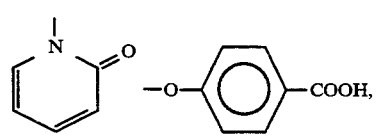
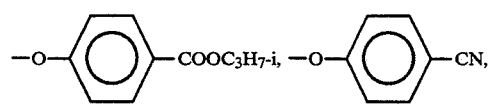
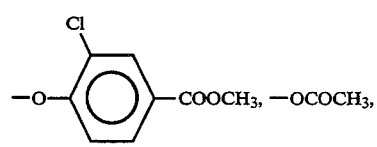
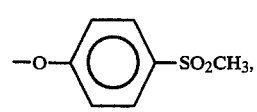
-continued
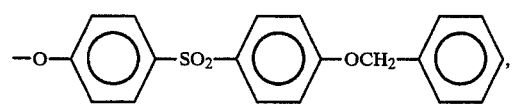
$-OSO_2CH_3$ 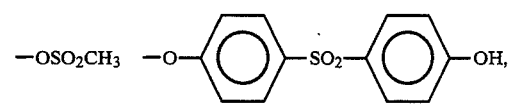
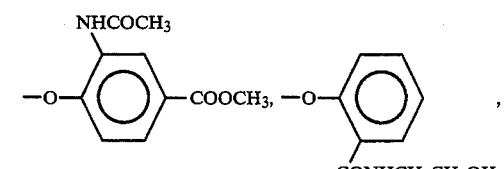
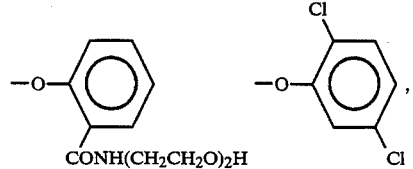
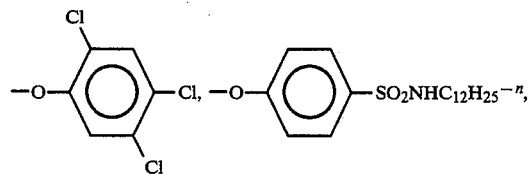
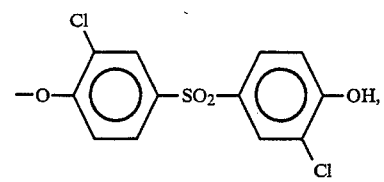
Exemplified yellow couplers represented by (Y) are shown below.

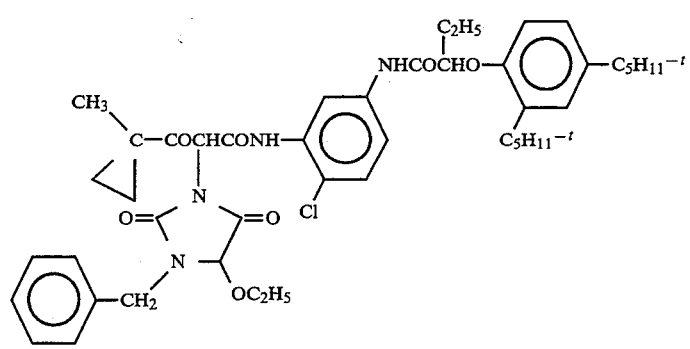 Y-1
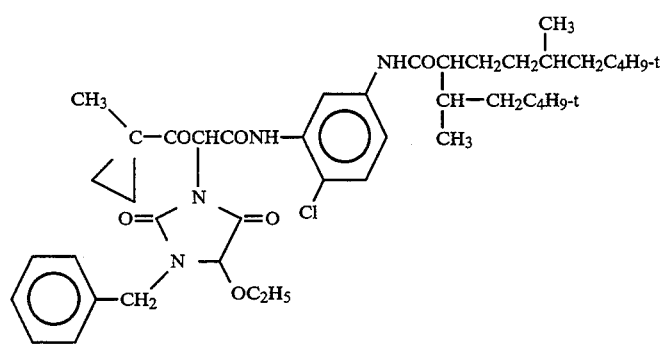 Y-2
Y-3
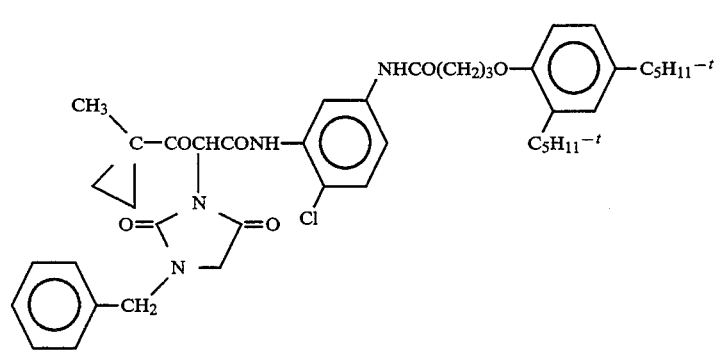 Y-4
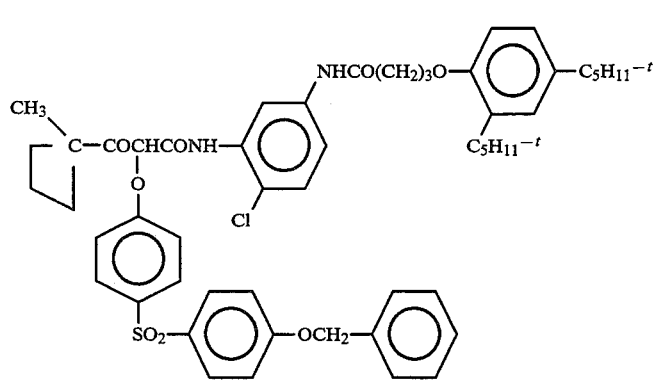 Y-5

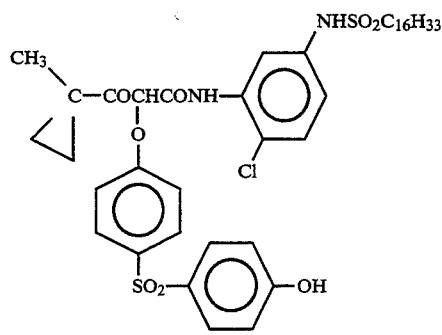
Y-6
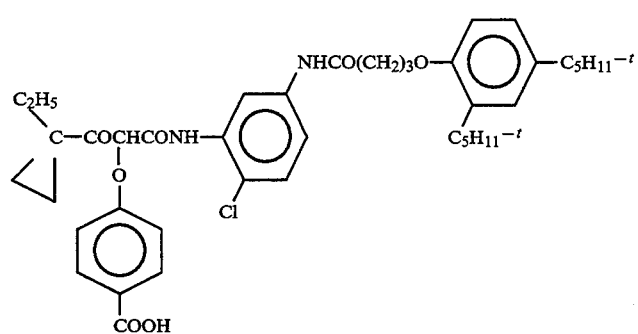
Y-7
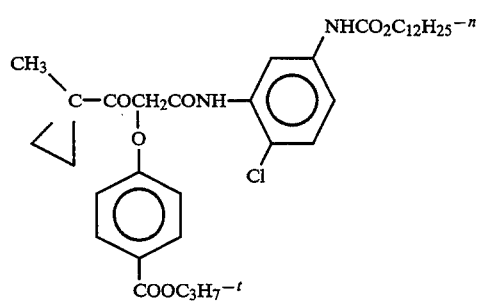
Y-8
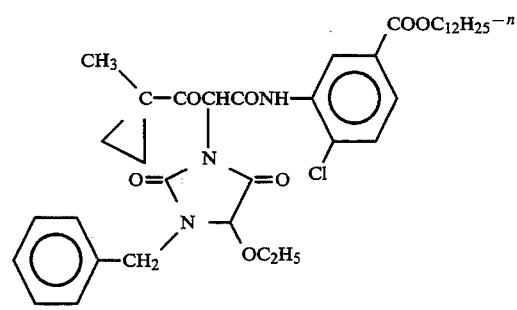
Y-9
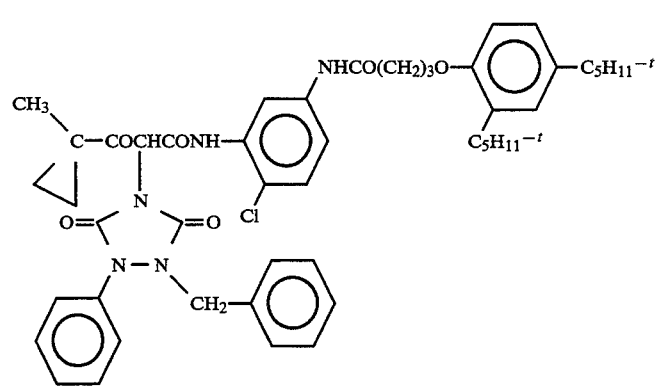
Y-10

-continued
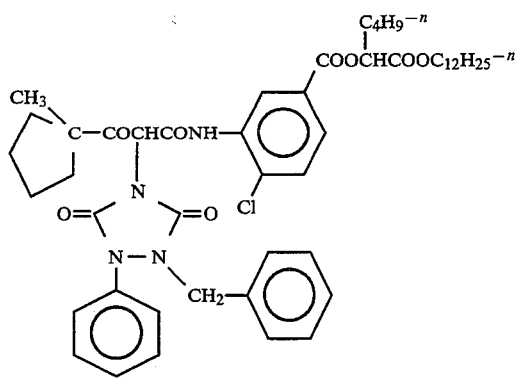
Y-11
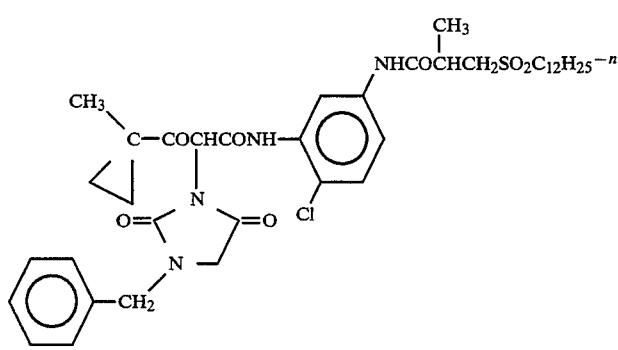
Y-12
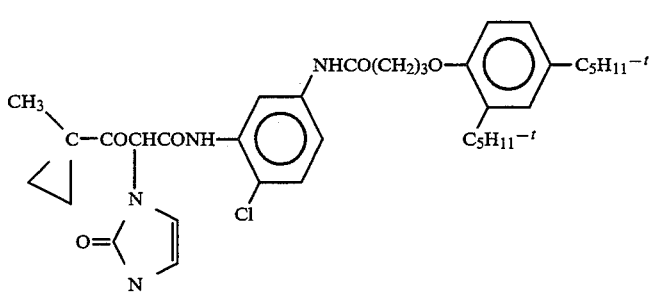
Y-13
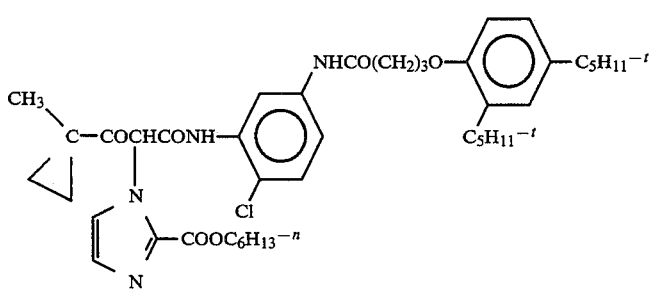
Y-14
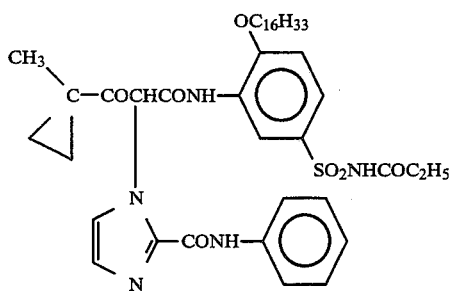
Y-15

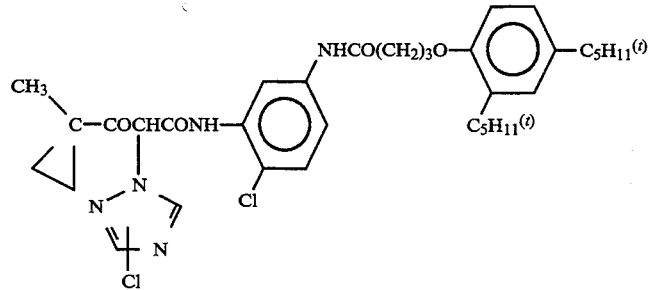 Y-16
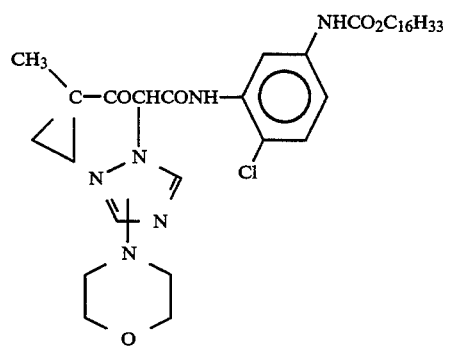 Y-17
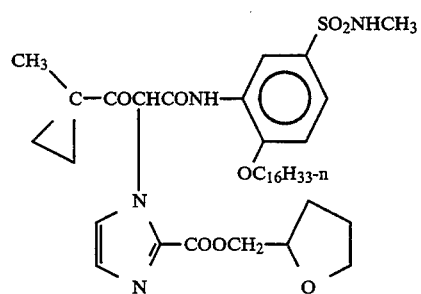 Y-18
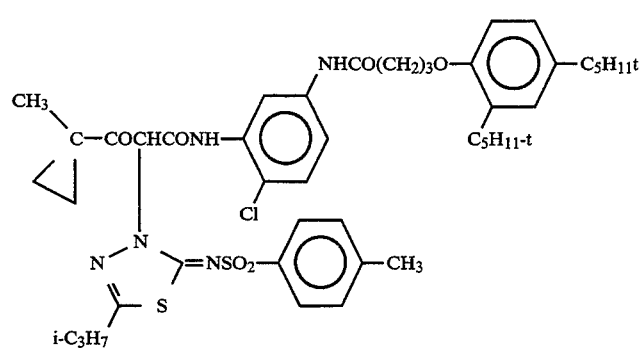 Y-19
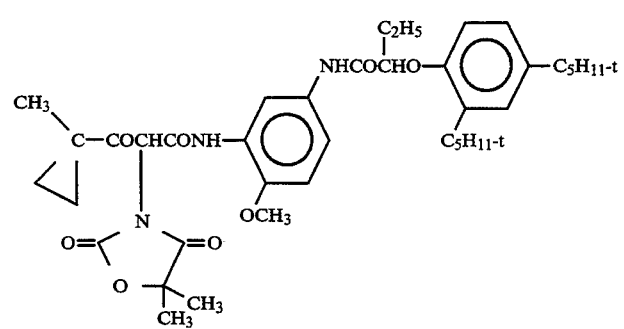 Y-20

-continued
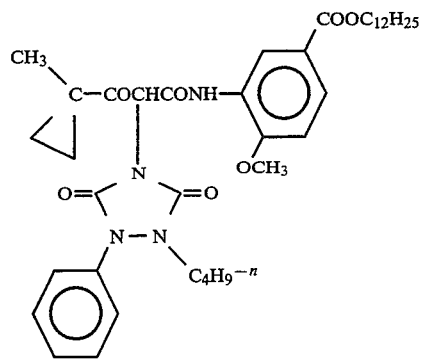
Y-21
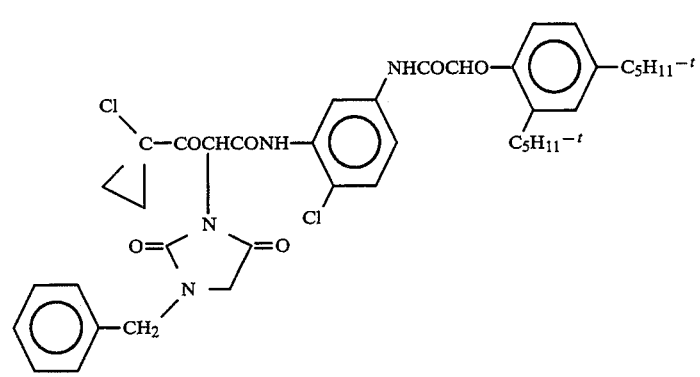
Y-22
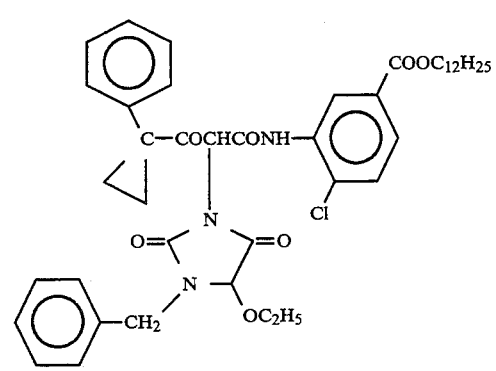
Y-23
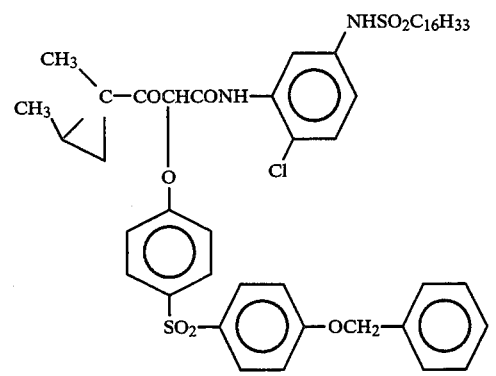
Y-24

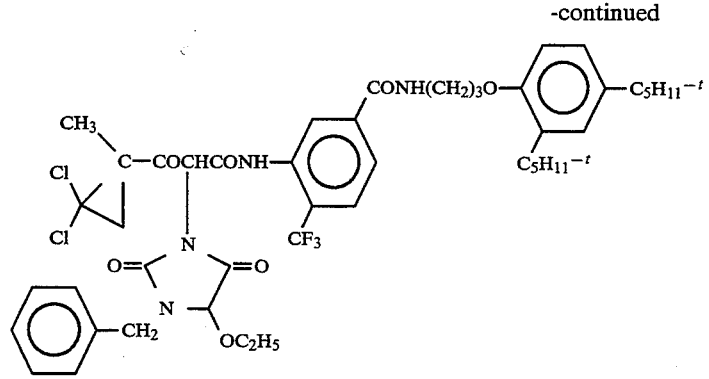 Y-25
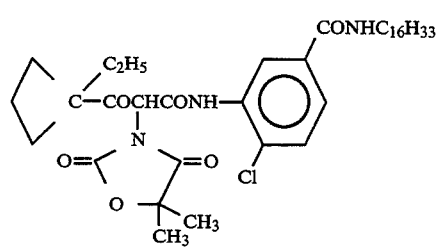 Y-26
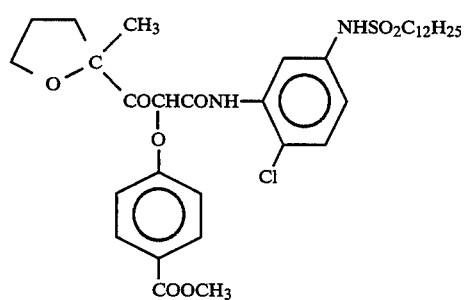 Y-27
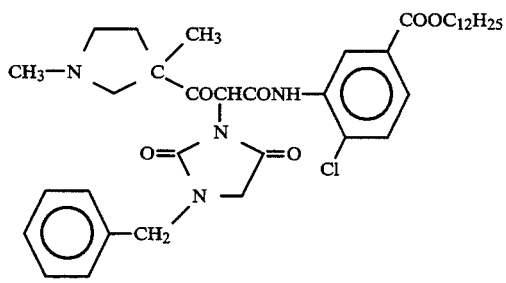 Y-28
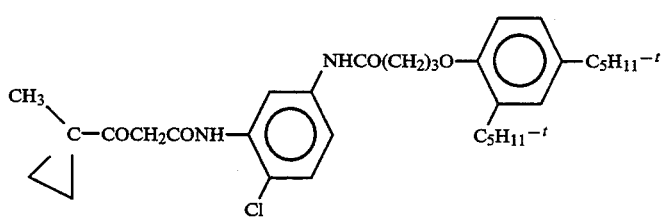 Y-29
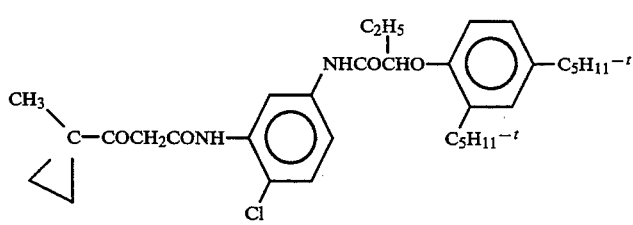 Y-30

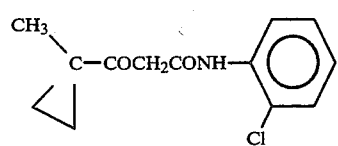 Y-31
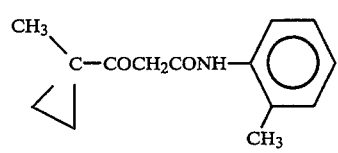 Y-32
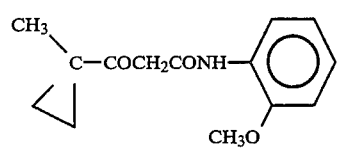 Y-33
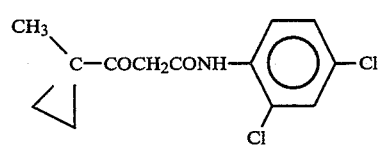 Y-34
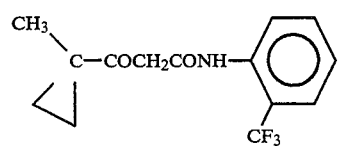 Y-35
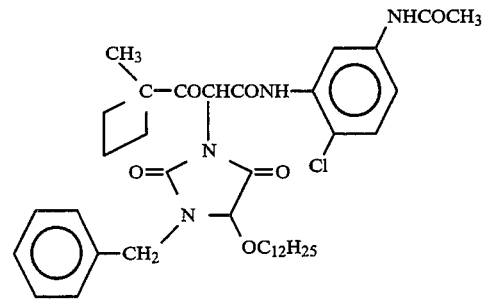 Y-36
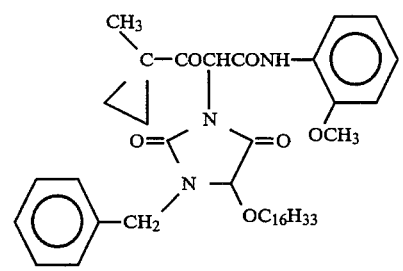 Y-37
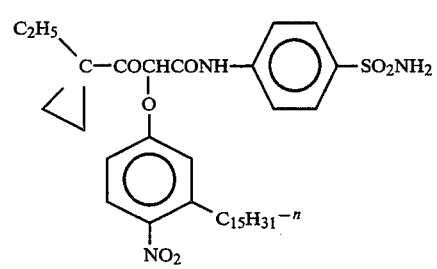 Y-38

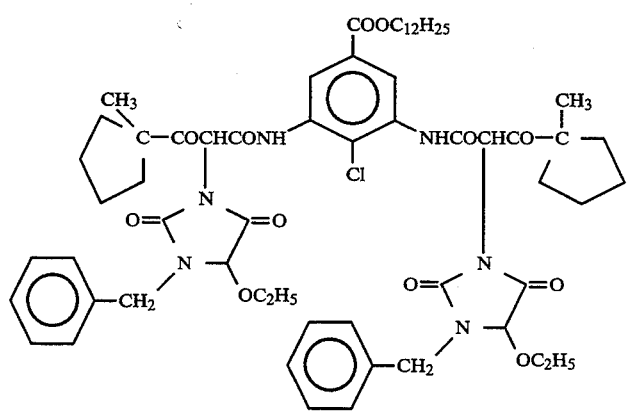
Y-39
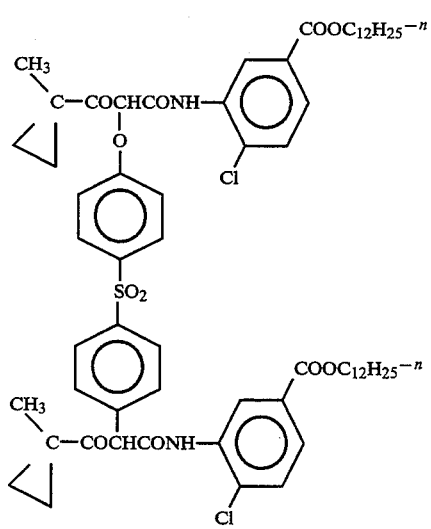
Y-40
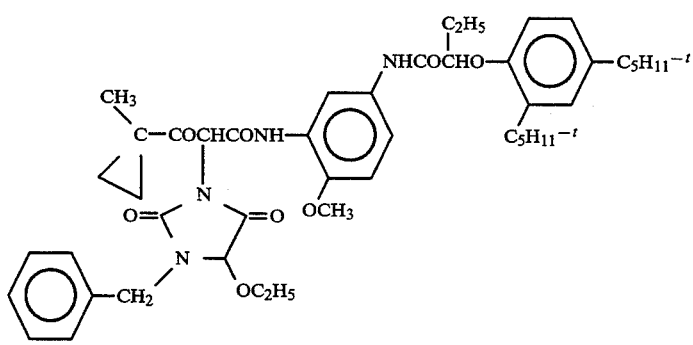
Y-41
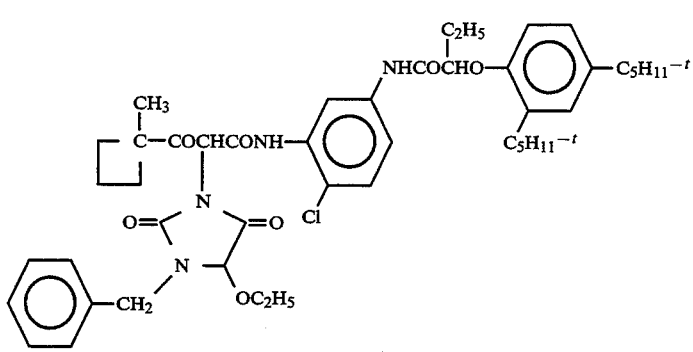
Y-42

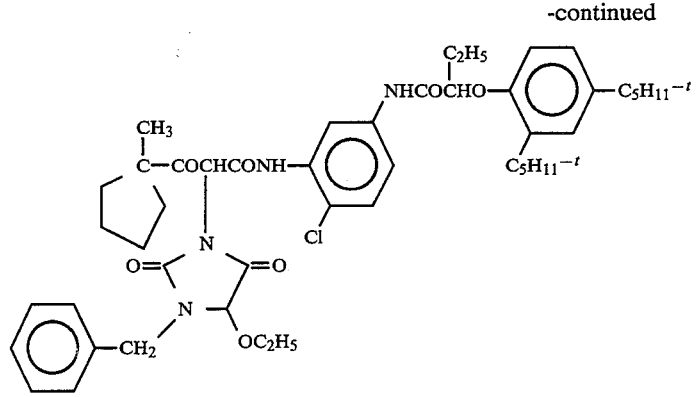
Y-43
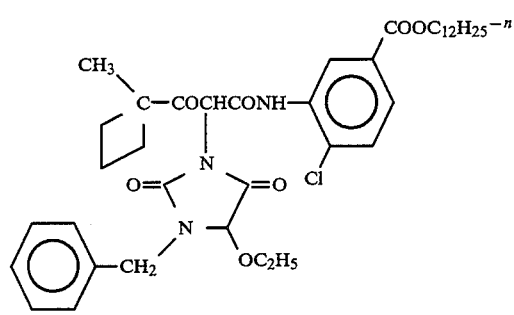
Y-44
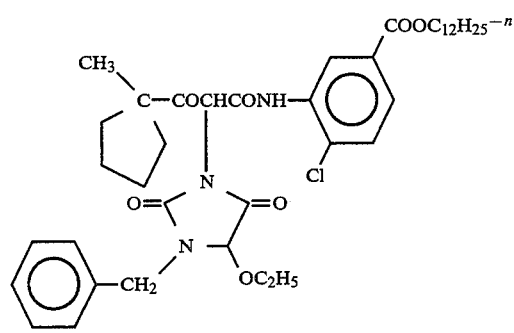
Y-45
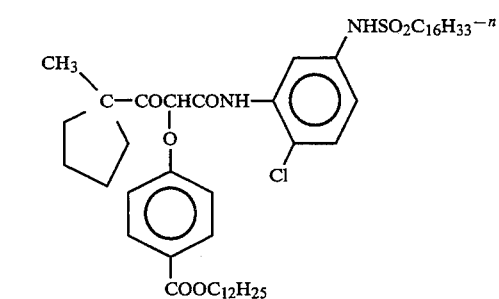
Y-46
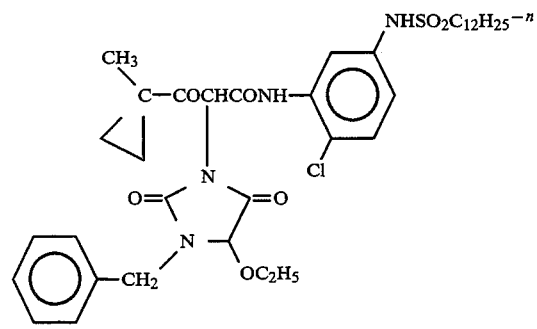
Y-47

-continued
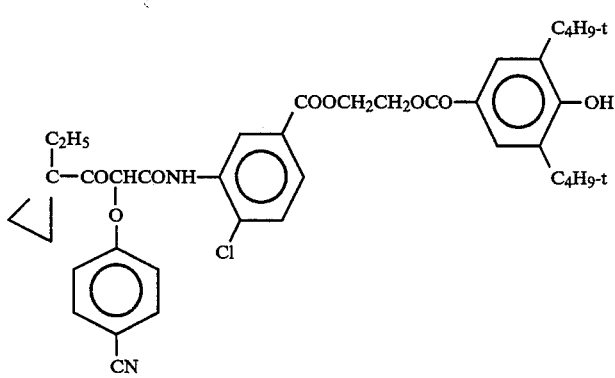
Y-48
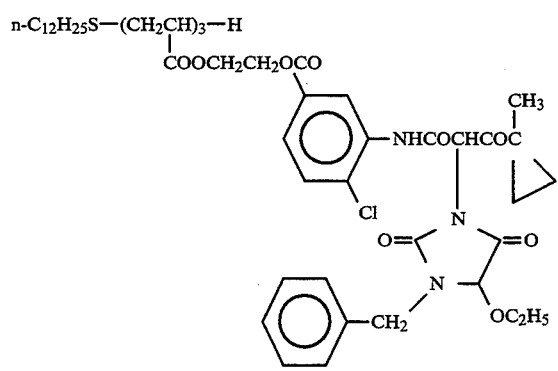
Y-49
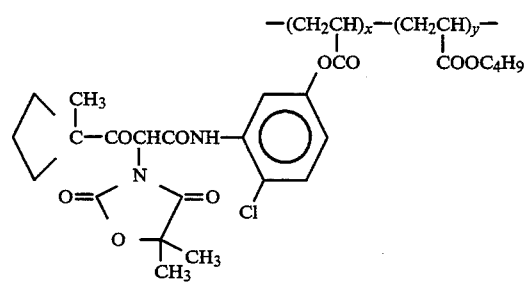
Y-50
x:y = 50:50(in weight ratio)
Number-average degree
of polymerization: 50,000
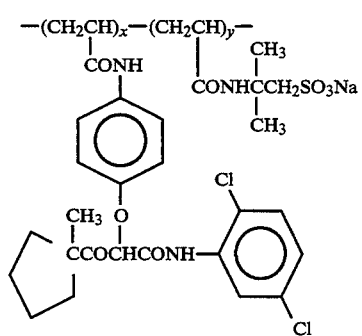
Y-51
x:y = 80:20(in weight ratio)
Number-average degree
of polymerization: 70,000

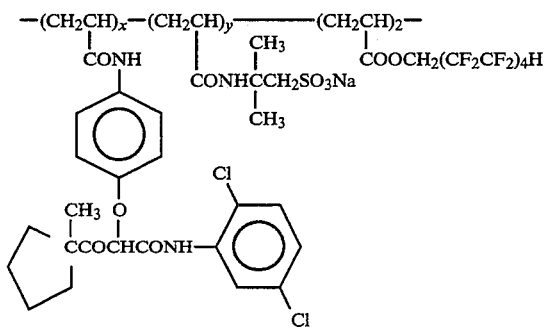
Y-52
x:y:z = 50:30:20
(in weight ratio)
Number-average degree
of polymerization: 70,000
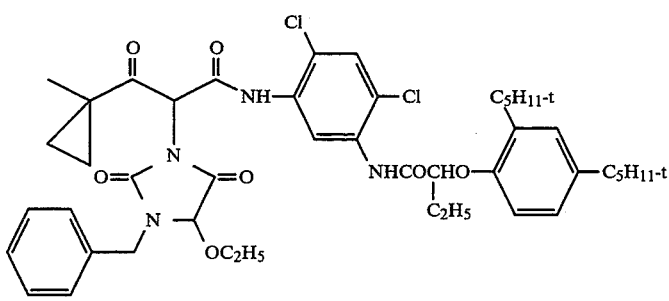
Y-53
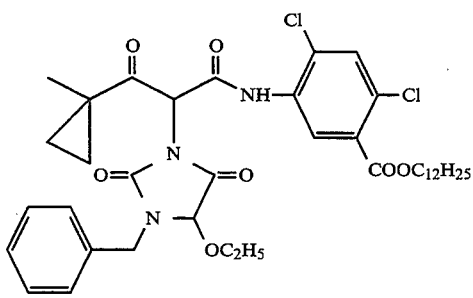
Y-54
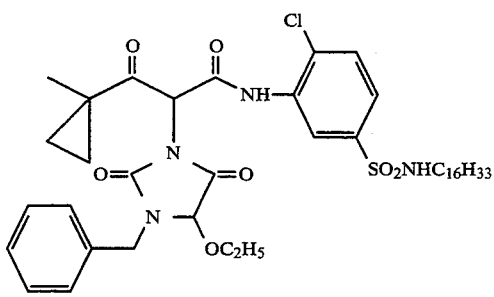
Y-55
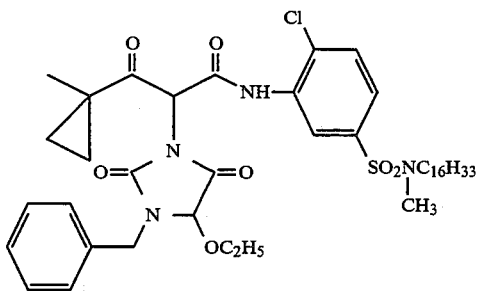
Y-56

-continued
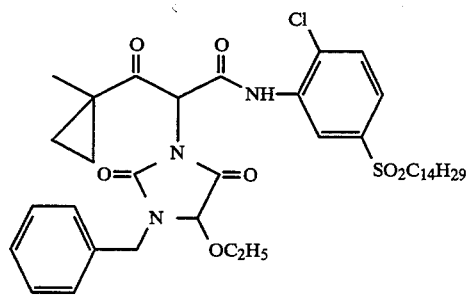
Y-57
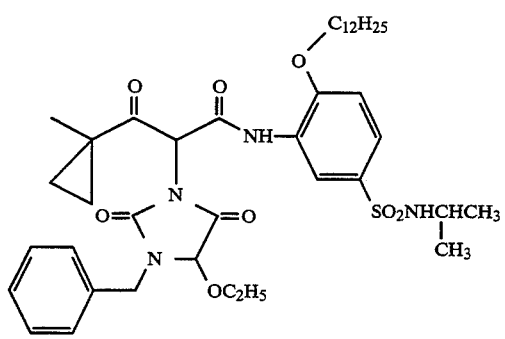
Y-58
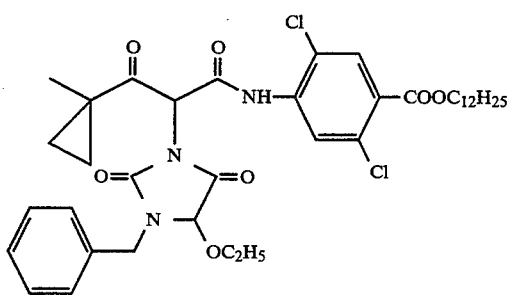
Y-59
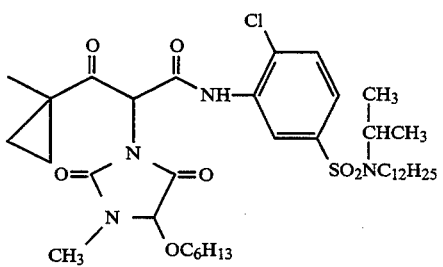
Y-60
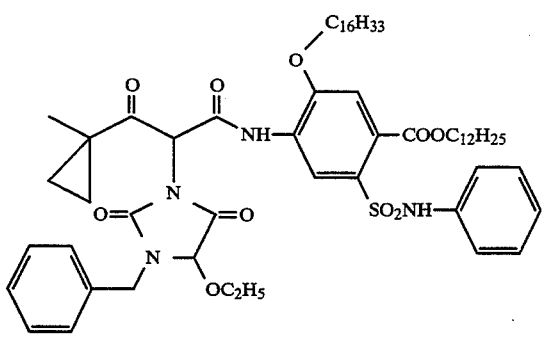
Y-61

-continued
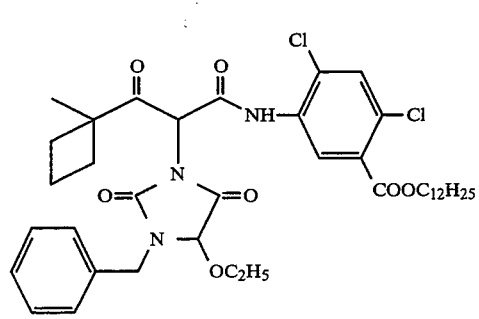
Y-62
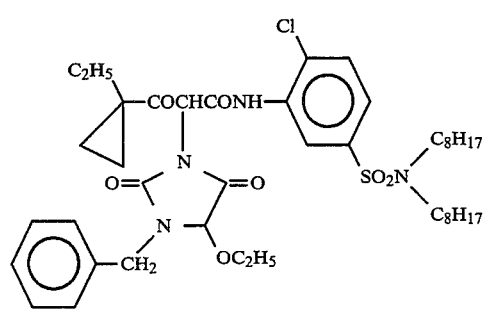
Y-63
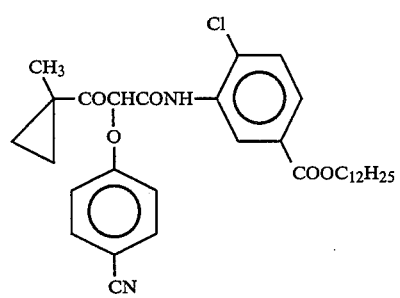
Y-64
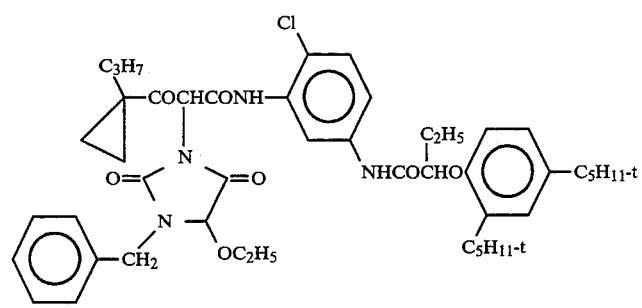
Y-65
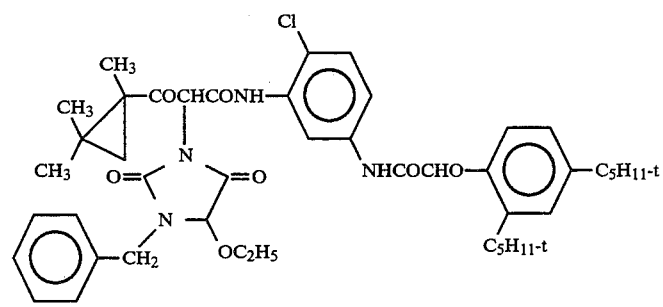
Y-66

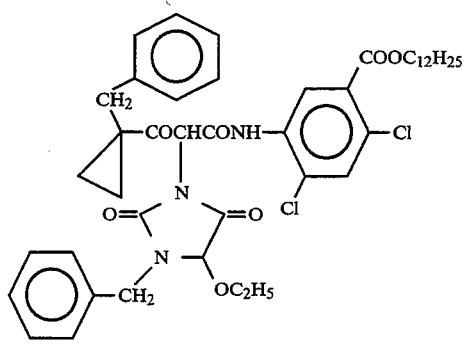
Y-67
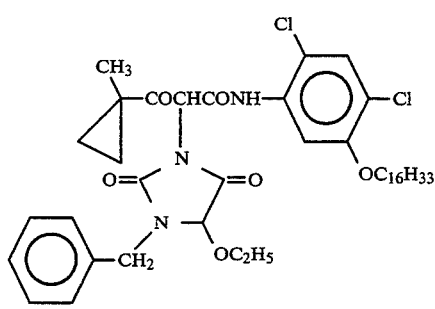
Y-68
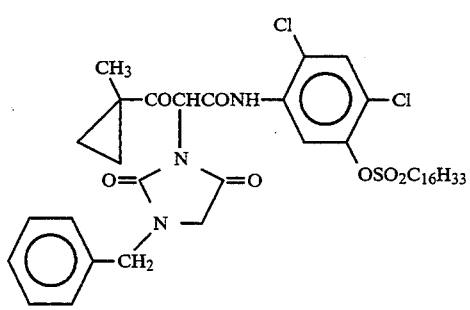
Y-69
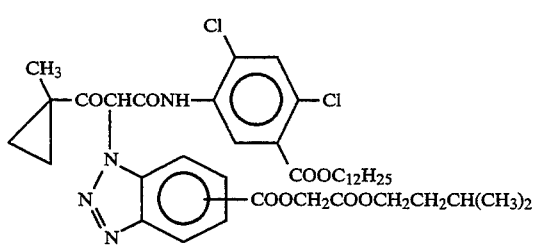
Y-70
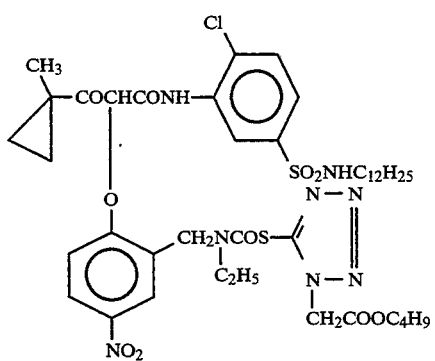
Y-71

-continued
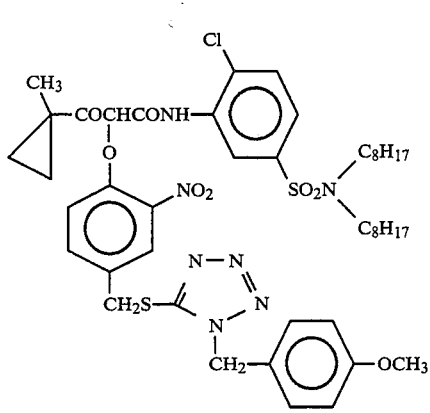
Y-72
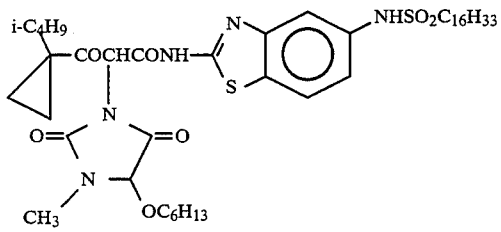
Y-73
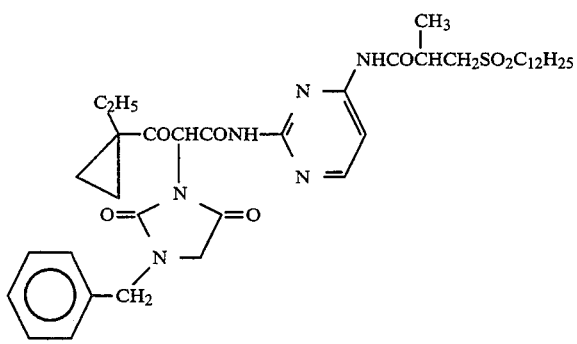
Y-74
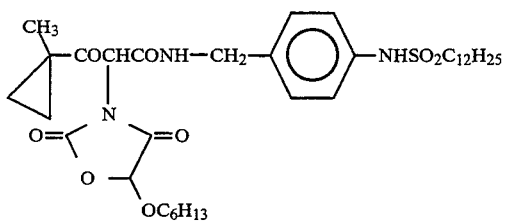
Y-75
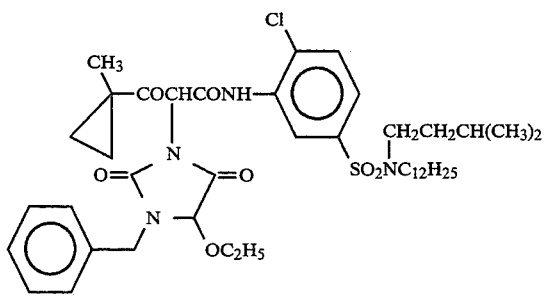
Y-76

Y-77

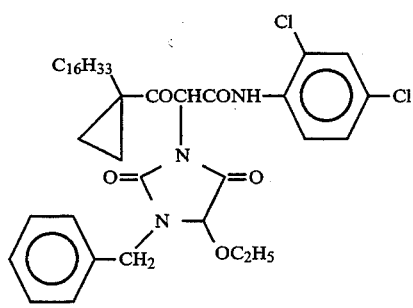

Y-78

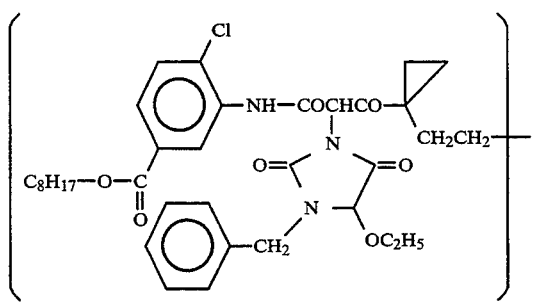

The present yellow couplers represented by formula (Y) can be synthesized through the following synthesis routes:

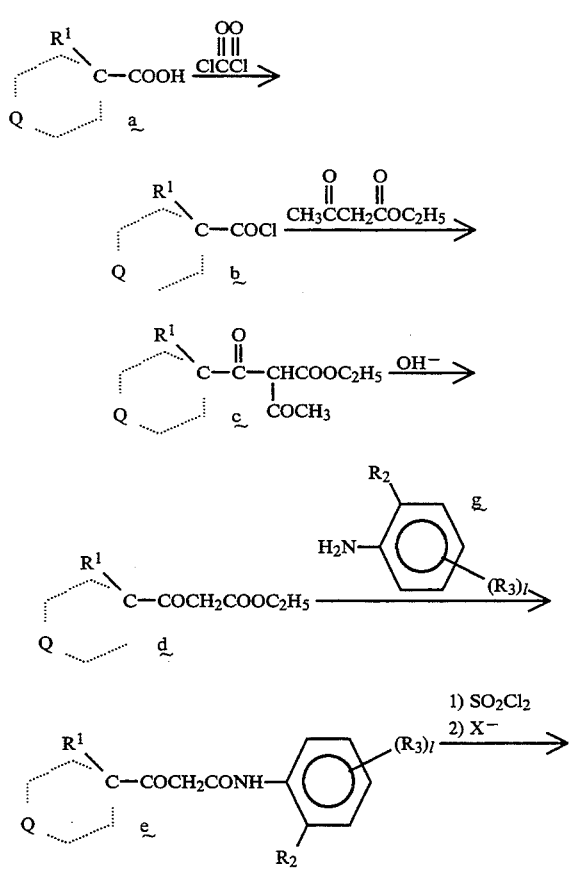

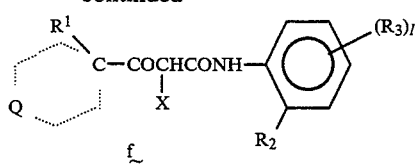

Compound a can be synthesized by any process described, for example, in J. Chem. Soc. (C), 1968, 2548; J. Am. Chem. Soc., 1934, 56, 2710; Synthesis, 1971, 258; J. Org. Chem., 1978, 43, 1729, and CA, 1960, 66, 18533y.

The synthesis of Compound b is carried out by a reaction using thionyl chloride, oxalyl chloride, etc., optionally in a solvent such as methylene chloride, chloroform, carbon tetrachloride, dichloroethane, toluene, N,N-dimethylformamide, and N,N-dimethylacetamide, generally at a reaction temperature of about $-20°$ to 150° C., and preferably at about $-10°$ to 80° C.

Compound c is synthesized by making ethyl acetoacetate into an anion using magnesium methoxide or the like and adding b thereto. The reaction is carried out optionally using a solvent such as tetrahydrofuran and ethyl ether, and the reaction temperature is generally about $-20°$ to 60° C., preferably about $-10°$ to 30° C. Compound d is synthesized by carrying out a reaction using Compound c and, as a base, an aqueous solution of ammonia, $NaHCO_3$, or NaOH, optionally in a solvent such as methanol, ethanol, and acetonitrile. The reaction temperature is generally about $-20°$ to 50°, preferably about $-10°$ to 30° C.

Compound e is synthesized by reacting compound d and compound g together without using a solvent. The reaction temperature is generally about 100° to 150° C., preferably about 100 to 120° C. When X is not H, after chlorination or bromination, the coupling split-off group X is introduced to synthesize compound f. Compound e is made into a chlorine-substituted product using, for example, a sulfuryl chloride or N-chlorosuccinimide in a solvent such as dichloroethane, carbon tetrachloride, chloroform, methylene chloride, and tetrahydrofuran, or it is made into a bromine-substituted product using, for example, bromine or N-bromosuccinimide in a solvent as above. In this case the reaction temperature is about −20° to 70° C., preferably about −10° to 50° C. Then, when the chlorine-substituted product or bromine-substituted product and the proton adduct H—X of the coupling split-off group are reacted in a solvent, such as methylene chloride, chloroform, tetrahydrofuran, acetone, acetonitrile, dioxane, N-methylpyrrolidone, N,N,-dimethylimidazolidin-2-one, N,N-dimethylformamide, and N,N-dimethylacetamide, at a reaction temperature of about −20° to 150° C., preferably about −10° to 100° C., Coupler $\underline{f}$ of the present invention can be obtained. At that time a base may be used, such as triethylamine, N-ethylmorpholine, tetramethylguanidine, potassium carbonate, sodium hydroxide, and sodium bicarbonate Synthesis Examples of couplers of the present invention are given below.

SYNTHESIS EXAMPLE 1

Synthesis of Exemplified Compound Y-30

38.1 g of oxalyl chloride was added dropwise to a mixture of 25 g of 1-methylcyclopropanecarboxylic acid, which was synthesized in accordance with the process described by Gotkis, D., et al., *J. Am. Chem. Soc.*, 1934, 56, 2710, 100 ml of methylene chloride, and 1 ml of N,N-dimethylformamide over 30 min at room temperature. After the completion of the addition, the reaction was continued for 2 hours at room temperature, and then the methylene chloride and the excess oxalyl chloride were removed under reduced pressure created by an aspirator, to produce an oil of 1-methylcyclopropanecarbonyl chloride.

100 ml of methanol was added dropwise to a mixture of 6 g of magnesium and 2 ml of carbon tetrachloride at room temperature over 30 min, and after the mixture was heated for 2 hours under reflux, 32.6 g of ethyl 3-oxobutanate was added dropwise thereto over 30 min under heating and reflux. After completion of the addition the heating was continued for 2 hours under reflux and then the methanol was distilled off completely under reduced pressure created by an aspirator. 100 ml of tetrahydrofuran was added to the reaction product, to disperse the reaction product, and the previously obtained 1-methylcyclopropanecarbonyl chloride as added dropwise to the dispersion at room temperature. After reacting for 30 min, the reaction liquid was extracted with 300 ml of ethyl acetate and dilute sulfuric acid, the organic layer was washed with water and then dried over anhydrous sodium sulfate, and the solvent was distilled off, to obtain 55.3 g of an oil of ethyl 2-(1-methylcyclopropanecarbonyl)-3-oxobutanate.

A solution of 55 g of ethyl 2-(1-methylcyclopropanecarbonyl)-3-oxobutanate in 160 ml of ethanol was stirred at room temperature and 60 ml of a 30 aqueous ammonia solution was added dropwise to the solution over 10 min. Thereafter the stirring was continued for 1 hour, then extraction with 300 ml of ethyl acetate and dilute hydrochloric acid was carried out, the organic layer was neutralized, washed with water, and dried over anhydrous sodium sulfate, and the solvent was distilled off, to obtain 43 g of an oil of ethyl (1-methylcyclopropanecarbonyl)acetate.

34 g of ethyl (1-methylcyclopropanecarbonyl)acetate and 44.5 g of N-(3-amino-4-chlorophenyl)-2-(2,4-di-t-phenylphenoxy)butaneamide were heated under reflux and reduced pressure created by an aspirator, with the internal temperature being 100° to 120° C. After the reaction was continued for 4 hours, the reaction liquid was refined by column chromatography using a mixed solvent of n-hexane and ethyl acetate, to produce 49 g of a viscous oil of the Exemplified Compound Y-30. The structure of the compound was identified by mass

SYNTHESIS EXAMPLE 2

Synthesis of Exemplified Compound Y-1

22.8 g of the Exemplified Compound Y-30 was dissolved in 300 ml of methylene chloride and was added dropwise to 5.4 g of sulfuryl chloride over 10 min with ice cooling. After the reaction had continued for 30 min, the reaction liquid was washed well with water, dried over anhydrous sodium sulfate, and then condensed, to obtain the chloride of the Exemplified Compound Y-30. The thus synthesized chloride of the Exemplified Compound Y-30 was dissolved in 50 ml of N,N-dimethylformaldehyde and was added dropwise to a solution of 50 ml of N,N-dimethylformaldehyde, 11.2 ml of triethylamine, and 18.7 g of 1-benzyl-5-ethoxyhydantoin over 30 min at room temperature.

Thereafter the reaction was allowed to continue for 4 hours at 40° C., and then the reaction liquid was extracted with 300 ml of ethyl acetate, thereafter washed with water and then washed with a 2% aqueous triethylamine solution. This was followed by neutralization with dilute hydrochloric acid. After the organic layer was dried over anhydrous sodium sulfate, the solvent was distilled off, and the resulting oil was crystallized from a mixed solvent of n-hexane and ethyl acetate. The deposited crystals were filtered, then washed with a mixed solvent of n-hexane and ethyl acetate, and dried, to obtain 22.8 g of crystals of the Exemplified Compound Y-1.

The structure of the compound was identified by mass spectrometry, NMR spectrometry, and elemental analysis. The melting point was 132° to 133° C.

The spectral absorption spectra and the molecular extinction coefficients of Dye A, obtained from the present Exemplified Compound Y-31, and Dye B, obtained from a pivaloylacetanilide-type coupler in ethyl acetate, were compared. Dye A showed excellent spectral absorption spectrum characteristics (better than Dye B), and it showed a molecular extinction coefficient which was about 30% higher than that of Dye B (FIG. 1).

|  | max (nm) | mol$^{-1}$ (cm−1) |
|---|---|---|
| Dye A | 428.8 | 19900 |

-continued

|  | max (nm) | mol$^{-1}$ (cm$-1$) |
|---|---|---|
| Dye B | 433.1 | 15400 |

Note:
max: Wavelength of maximum absorption
: Molecular extinction coefficient

Dye A

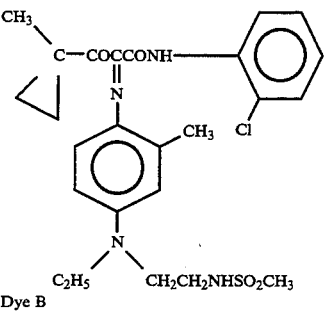

Dye B

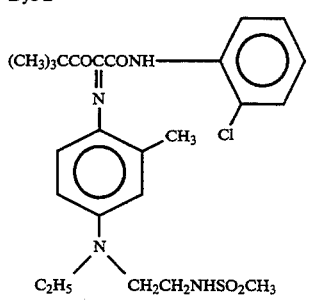

SYNTHESIS EXAMPLE 3

Synthesis of Exemplified Compound Y-43

N-[2-Chloro-5-(2-(2,4-di-t-pentylphenoxy)-butaneamido)phenyl]-2-(1-methylcyclopentanecarbonyl) acetamide was prepared in the same manner as in Synthesis Example 1, except that, as a raw material, 32 g of 1-methylcyclopentane-carbonic acid that had been synthesized by the method described in Organic Synthesis, Vol. 46, 72 using cyclohexyl alcohol as a starting material was used instead of 1-methylcyclopropane-carbonic acid in Synthesis Example 1 to obtain 50 g of an amorphous product. Then, 23.9 g of his N-[2-chloro-5-(2-(2,4-di-t-pentylphenoxy)butaneamido)phenyl]-2-(methylcyclopentane-carbonyl)acetanide was subjected to the same reaction treatment as in Synthesis Example 2 in which 30 g of exemplified compound 30 was used as a raw material, to obtain an oily product. The thus-obtained oily product was purified by a column chromatography using a mixture solvent of n-hexane and ethyl acetate to obtain 26.5 g of exemplified compound Y-43 in tacky oil. The structure of the compound was identified by mass spectrometry, NNR spectrometry, and elemental analysis.

The method of the present invention can be adopted to any type of processing process. For example, they can be adopted to the processing of a color paper, a color reverse paper, a color positive film, a color negative film, a color reverse film, or a color direct positive photographic material.

The silver halide emulsion of the color photographic material to be used in the present invention may be any type of halogen composition, including silver bromide, silver iodobromide, silver bromochloroiodide, silver chlorobromide or silver chloride.

Although the halogen compositions of the emulsion may be the same or different from grain to grain, if emulsions whose grains have the same halogen composition are used, it is easy to make the properties of the grains homogeneous. With respect to the halogen composition distribution in a silver halide emulsion grain there can be suitably selected and used for example, a grain having a so-called uniform-type structure, wherein the composition is uniform throughout the silver halide grain, a grain having a so-called layered-type structure, wherein the halogen composition of the core of the silver halide grain is different from that of the shell (which may comprise a single layer or layers) surrounding the core, or a grain having a structure with nonlayered parts different in halogen composition in the grain or on the surface of the grain (if the nonlayered parts are present on the surface of the grain, the structure has parts different in halogen composition joined onto the edges, the corners, or the planes of the grain). To secure high sensitivity, it is more advantageous to use one of the latter two types of grains, rather than using grains having a uniform-type structure. The use of the latter types of grains is also preferable in view of their pressure resistance. If the silver halide grains have the above-mentioned structure, the boundary section between parts different in halogen composition may be a clear boundary, or an unclear boundary, due to the formation of mixed crystals caused by differences in composition, or they may have positively varied continuous structures.

The composition of silver halide may be changed according to the purpose to which the photographic material is to be adopted. For example, a silver halide emulsion comprising mainly silver chlorobromide may be used for a print material, such as a color paper, while an emulsion comprising mainly silver iodobromide being used for a photographic material, such as a color negative film.

Further in a photographic material suitable for the rapid processing of an emulsion having a high silver chloride content, a so-called high-silver-chloride emulsion, may be used preferably. The content of silver chloride in the high-silver-chloride emulsion is preferably 90 mol % or over, more preferably 95 mol % or over.

In these high-silver-chloride emulsions, the structure is preferably such that the silver bromide localized phase in the layered form or nonlayered form is present in the silver halide grain and/or on the surface of the silver halide grain as mentioned above. The silver bromide content of the composition of the above-mentioned localized phase is preferably at least 10 mol %, and more preferably over 20 mol %. The localized phase may be present in the grain, or on the edges, or corners of the grain surfaces, or on the planes of the grains, and a preferable example is a localized phase epitaxially grown on each corner of the grain.

The average grain size of the silver halide grains (expressed in terms of the grain diameter for spherical or semi-spherical grains, the edge length for cubic grains, and the spherical diameter for tabular grains, which can be determined as the average of the projected area diameter) is preferably smaller than 2 μm and larger than 0.1 μm, most preferably smaller than 1.5 μm and larger than 0.15 μm. The distribution of grain size may be either narrow or wide, but it is preferable in the present invention to use the so-called monodisperse emulsion of silver halide having a value (deviation coefficient) obtained by dividing the standard deviation calculated from the size distribution curve by the average grain size of 20% or less, most preferably 15% or less. In order to realize the gradation desired for the photographic material, two or more monodisperse silver halide emulsions (preferably all emulsions having the above-mentioned deviation coefficient) different in grain size may be mixed in a single layer or coated as different layers that have substantially the same color sensitivity. Further, two or more polydisperse silver halide emulsions or a combination of monodisperse and polydisperse emulsions can be used.

Silver halide grains for use in the present invention may have a regular crystal structure, such as cubic, hexahedral, rhombic dodecahedral, tetradecahedral, or a mixture thereof, or an irregular crystal structure, such as spherical or thereof composite crystal structure. Further tabular grains can be employed.

The silver halide photographic emulsions that can be used in this invention may be prepared suitably by known means, for example, by the methods described in I. *Emulsion Preparation and Types*, in *Research Disclosure* (RD), No. 17643 (December 1978), pp. 22–23, and in ibid, No. 18716 (November 1979), p. 648; the methods described in P. Glafkides, *Chemie et Phisique Photographique*, Paul Montel (1967), in G. F. Duffin, *Photographic Emulsion Chemistry*, Focal Press (1966), and in V. L. Zelikman et al., *Making and Coating of Photographic Emulsion*, Focal Press (1964).

A monodisperse emulsion, such as described in U.S. Pat. Nos. 3,574,628 and 3,655,394, and in British Patent No. 1.413,748, is also preferable.

Tabular grains having an aspect ratio of 5 or greater can be used in the emulsion of this invention. Tabular grains can be easily prepared by the methods described in, for example, Gutoof, *Photographic Science and Engineering*, Vo. 14 pp 248–257 (1970) U.S. Pat. Nos. 4,434,226, 4,414,310, 4,433,048, and 4,439,520, and British Patent No. 2,112,157.

The crystal structure of the emulsion grains may be uniform, the outer halogen composition of the crystal structure may be different from the inner halogen composition, or the crystal structure may be layered. Silver halides whose compositions are different may be joined by the epitaxial joint, or a silver halide may be joined, for example, to a compound other than silver halides, such as silver rhodanide, lead oxide, etc.

Further, the silver halide may be a mixture of grains having various crystal shapes.

The silver halide emulsion may generally be physically ripened, chemically ripened, and spectrally sensitized. Additives that will be used in these steps are described in *Research Disclosure* no. 1763 and ibid. No. 18716, and involved sections are listed in the Table shown below.

Known photographic additives that can be used in this invention are also described in the above-mentioned two Research Disclosures, and the involved sections are listed in the same Table below.

| | Additive | RD 17643 | RD 18716 |
|---|---|---|---|
| 1 | Chemical sensitizer | p. 23 | p. 648 (right column) |
| 2 | Sensitivity-enhancing agents | — | " |
| 3 | Spectral sensitizers and Superstabilizers | pp. 23–24 | pp. 648 (right column –649 (right column) |
| 4 | Brightening agents | p. 24 | — |
| 5 | Antifogging agents and Stabilizers | pp. 24–25 | p. 649 (right column) |
| 6 | Light absorbers, | pp. 25–26 | pp. 649 (right column) |

-continued

| | Additive | RD 17643 | RD 18716 |
|---|---|---|---|
| | Filter dyes, and UV Absorbers | | –650 (left column) |
| 7 | Stain-preventing agents | p. 25 (right column) | p. 650 (left to right column) |
| 8 | Image dye stabilizers | p. 25 | — |
| 9 | Hardeners | p. 26 | p. 651 (left column) |
| 10 | Binders | p. 26 | " |
| 11 | Plasticizers and Lubricants | p. 27 | p. 650 (right column) |
| 12 | Coating aids and Surface-active agents | pp. 26–27 | " |
| 13 | Antistatic agents | p. 27 | " |

Further, in order to prevent the lowering of photographic performances due to formaldehyde gas, a compound described in, for example, U.S. Pat. Nos. 4,411,987 and 4,435,503 that is able to react with formaldehyde to immobilize it can be added to the photographic material.

Various color couplers can be used in this invention, and typical examples are described in the patents in the above-mentioned *Research Disclosure* No. 17643, VII-C to G.

As yellow couplers for combined use with the couplers of the present invention, those described, for example, in U.S. Pat. Nos. 3,933,501, 4,022,620, 4,326,024, 4,401,752, and 4,428,961, JP-B ("JP-B" means examined Japanese patent publication) No. 10739/1983, British Patent Nos. 1,425,020 and 1,476,760, U.S. Pat. Nos. 3,973,968, 4,314,023, and 4,511,649, and European Patent No. 249,473A are preferable.

As magenta couplers, the 5-pyrazolone type and pyrazoloazole type are preferable, those described in U.S. Pat. Nos. 4,310,619 and 4,315,897, European Patent No. 73,636, U.S. Pat. Nos. 3,061,432 and 3,725,067, *Research Disclosure* No. 24220 (June 1984), JP-A No. 33552/1985, *Research Disclosure* No. 24230 (June 1984), JP-A Nos. 43659/1985, 72238/1986, 35730/1985, 118034/1980, and 185951/1985, U.S. Pat. Nos. 4,500,630, 4,540,654, and 4,556,630, and International Patent Publication No. WO 88/04795 are particularly preferable.

The cyan couplers include phenol-type couplers and naphthol-type couplers, and those described in U.S. Pat. Nos. 4,052,212, 4,146,396, 4,228,233, 4,296,200, 2,369,929, 2,801,171, 2,772,162, 2,895,826, 3,772,002, 3,758,308, 4,334,011, and 4,327,173, West German Patent Application (OLS) No. 3,329,729, European Patent Nos. 121,365A and 249,453A, U.S. Pat. Nos. 3,446,622, 4,333,999, 4,775,616, 4,451,559, 4,427,767, 4,690,889, 4,254,212, and 4,296,199, and JP-A No. 42658/1986 are more preferable.

As a colored coupler to rectify the unnecessary absorption of color-forming dyes, those couplers described in paragraph VII-G of *Research Disclosure* No. 17643, U.S. Pat. No. 4,163,670, JP-B No. 39413/1982, U.S. Pat. Nos. 4,004,929, and 4,138,258, and British Patent No. 1,146,368 are preferable. Further, it is preferable to use couplers to rectify the unnecessary absorption of color-forming dyes by a fluorescent dye released upon the coupling as described in U.S. Pat. No. 4,774,181 and by couplers having a dye precursor, as a group capable of being released, that can react with the developing agent to form a dye as described in U.S. Pat. No. 4,777,120.

As a coupler which forms a dye having moderate diffusibility, those described in U.S. Pat. No. 4,366,237, British Patent No. 2,125,570, European Patent No. 96,570, and West German Patent Application (OLS) No. 3,234,533 are preferable.

Typical examples of a polymerized dye-forming coupler are described in U.S. Pat. Nos. 3,451,820, 4,080,211, 4,367,282, 4,409,320, and 4,576,910, and British Patent No. 2,102,173.

A coupler that releases a photographically useful residue accompanied with the coupling reaction can be used favorably in this invention. As a DIR coupler that releases a development retarder, those described in patents cited in paragraph VII-F of the above-mentioned *Research Disclosure* No. 17643, JP-A Nos. 151944/1982, 154234/1982, 184248/1985, 37346/1988, and 37350/1988, and U.S. Pat. Nos. 4,286,962 and 4,782,012 are preferable.

As a coupler which releases, imagewisely, a nucleating agent or a development accelerator upon developing, those described in British Patent Nos. 2,097,140 and 2,131,188, and JP-A Nos. 157638/1984 and 170840/1984 are preferable.

Other couplers that can be incorporated in the photographic material of this invention include competitive couplers described in U.S. Pat. No. 4,130,427, multi-equivalent couplers described in U.S. Pat. Nos. 4,283,472, 4,338,393, and 4,310,618, couplers which release a DIR redox compound, couplers which release a DIR coupler, and redox compounds which release a DIR coupler or a DIR redox as described in JP-A Nos. 185950/1985 and 24252/1987, couplers which release a dye to regain a color after releasing as described in European Patent Nos. 173,302A and 313,308A, couplers which release a bleaching-accelerator as described in RD. Nos. 11449 and 24241, and JP-A No. 201247/1986, couplers which release a ligand as described in U.S. Pat. No. 4,553,477, couplers which release a leuco dye as described in JP-A No. 75747/1988, and couplers which release a fluorescent dye as described in U.S. Pat. No. 4,774,181.

The coupler to be used in this invention can be incorporated to photographic materials by various known dispersing processes.

Examples of a high-boiling organic solvent for use in an oil-in-water dispersing process are described, for example, in U.S. Pat. No. 2,332,027.

The steps and effects of the latex dispersion method and examples of latex are described, for exampie, in U.S. Pat. No. 4,199,363, West German Patent Application (OLS) Nos. 2,541,274 and 2,541,230, and a dispersion method using a polymer soluble in organic solvent is described in PCT International Publication No. WO 88/00723.

Specific examples of high-boiling organic solvent that are used in the above-mentioned oil-in water dispersing process include alkylester phthalate (e.g., dibutyl phthalate and dioctyl phthalate), phosphate ester (e.g., diphenyl phosphate, triphenyl phosphate, tricresyl phosphate, and dioctylbutyl phosphate), citrate ester (e.g., tributylacetyl citrate), benzoate ester (e.g., 2-ethylhexyl benzoate and 2-ethylhexyl-2, 4-dichloro benzoate), alkylamide (e.g., diethyllaurylamide), ester of aliphatic acid (e.g., dibutoxyethyl succinate, di-2-ethylhexyl succinate, 2-hexyldecyl tetradecanate, tributyl citrate, and diethyl azelate), chlorinated paraffin (paraffin having a chlorine content of 10 to 80 and esters of trimethinate (e.g., tributyl trimethinate), or organic solvents having a boiling point of about 30° to 150° C., for example, lower alkyl acetates such as ethyl acetate and butyl acetate, ethyl propionate, secondary butyl alcohol, methylisobutyl ketone, $\beta$-ethoxyethyl acetate and methyl cellosolve acetate may be used in combination.

The yellow coupler of the present invention may be used, generally, in the range of $1 \times 10^{-3}$ mol to 1 mol, preferably $1 \times 10^{-2}$ mol to $8 \times 10^{-1}$ mol, per mol of silver halide in the layer to be used. Further the coupler of the present invention may be used in combination with other yellow coupler.

Although the layer to which the yellow coupler of the present invention is added may be any silver halide layer or non-photosensitive layer, preferably it is used in a blue-sensitive silver halide emulsion layer or a layer adjacent to the blue-sensitive layer. When it is used in a blue-sensitive silver halide emulsion layer, preferably the amount of silver is 0.1 to 10 g/m$^2$. Further, when the yellow coupler of the present invention is used in a non-photosensitive layer, preferably it is used in an amount of 0.1 to 2 mmol/m$^2$.

The amount of color coupler to be used is, as a standard, in a range of 0.001 to 2 mol per mol of silver halide, preferably 0.01 to 1.5 mol for yellow coupler, 0.003 to 1.0 mol for magenta coupler, and 0.002 to 1.0 mol for cyan coupler, per mol of silver halide.

In the color photographic materials of this invention, it is preferable to add various preservatives or mildew proofing agent, such as 1,2-benzisothiazoline-3-one, n-butyl-p-hydroxy benzoate, phenol, 4-chloro-3, 5-dimethyl phenol, 2-phenoxyethanol, and 2-(4-thiazolyl)-benzimidazole, as described in JP-A Nos. 257747/1988, 272248/1987, and 80941/1989.

A photographic material of this invention is prepared by coating a flexible base, such as a plastic film (e.g., cellulose nitrate, cellulose acetate, and polyethylene telephthalate), a paper (of the type usually used), or a rigid base, such as glass plate. Details relating to the bases and coating methods are described in *Research Disclosure*, Vol. 176, Item 17643, paragraph XV (p.27) and paragraph XVIII (p. 28)(December 1978).

A photographic material that is prepared by using this invention may contain, as color antifoggant, for example, a hydroquinone derivative, or an ascorbic acid derivative.

In a photographic material of the present invention, various anti-fading agents (discoloration preventing agents) can be used. That is, as organic anti-fading additives for cyan, magenta and/or yellow images, there can typically be used hydroquinones, 6-hydroxychromans, 6-hydroxycoumarans, spirochromans, hindered phenols including p-alkoxyphenols and bisphenols, gallic acid derivatives, methylenedioxy-benzenes, aminophenols, hindered amines, and ether or ester derivatives obtained by silylating or alkylating the phenolic hydroxyl group of these compounds. Metal complexes such as (bissalicyl-aldoximate) nickel complex and (bis-N,N-dialkyldithiocarbamato) nickel complex can also be used.

Specific examples of the organic anti-fading agents are described in the following patent specifications:

Hydroquinones are described, for example, in U.S. Pat. Nos. 2,360,290, 2,418,613, 2,70,453, 2,701,197, 2,728,659, 2,732,300, 2,735,765, 3,982,944, and 4,430,425, British Patent No. 1,363,921, and U.S. Pat. Nos. 2,710,801 and 2,816,028, 6-hydroxychromans; 5- hydroxycoumarans and spirochromans are described, for example, in U.S. Pat. Nos. 3,432,300, 3,573,050, 3,574,627, 3,698,909, and 3,764,337, and JP-A No. 152225/1977; spiroindanes are described in U.S. Pat. No. 4,360,589; p-alkoxyphenols are described, for example, in U.S. Pat. No. 2,735,765, British Patent No. 2,066,975, JP-A No. 10539/1984, and JP-B No. 19765/1982; hindered phenols are described, for example, in U.S. Pat. No. 4,228,235, and JP-B No. 6623/1977; gallic acid derivatives, methylenedioxybenzenes, and aminophenols are described, for example, in U.S. Pat. Nos. 3,457,079 and 4,332,886, and JP-B No. 21144/1981 respectively; hindered amines are described, for example, in U.S. Pat. Nos. 3,336,135, and 4,286,593, British Patent Nos. 1,326,889, 1,354,313, and 1,410,846, JP-B No. 1420/1976, and JP-A Nos. 114036/1983, 53846/1984, and 78344/1984; and metal complexes are described, for example, in U.S. Pat. Nos. 4,050,938 and 4,241,155 and British Patent No. 2,027,731(A). To attain the present purposes, these compounds can be added to the photosensitive layers by coemulsifying them with the corresponding couplers, with the amount of each compound being generally 5 to 100 wt. % for the particular coupler. To prevent the cyan dye image from being deteriorated by heat, and in particular light, it is more effective to introduce an ultraviolet absorber into the cyan coupler-forming layer and the opposite layers adjacent to the cyan color-forming layers.

As the ultraviolet absorber, aryl-substituted benzotriazole compounds (e.g., those described in U.S. Pat. No. 3,533,794), 4-thiazolidone compounds (e.g., those described in U.S. Pat. Nos. 3,314,794 and 3,352,681), benzophenone compounds (e.g., those described in JP-A No. 2784/1971), cinnamic acid ester compounds (e.g., those described in U.S. Pat. Nos. 3,705,805 and 3,707,395), butadiene compounds (e.g., those described in U.S. Pat. No. 4,045,229), or benzoxazole compounds (e.g., those described in U.S. Pat. No. 3,700,455) can be used. Ultraviolet-absorptive couplers (e.g., α-naphthol type cyan dye forming couplers) and ultraviolet-absorptive polymers can, for example, be used also. These ultraviolet-absorbers may be mordanted in the special layer.

Of these, benzotriazole compounds substituted by an aryl group as described above are preferable.

As a binder or a protective colloid that can be used in the emulsion layers of the photographic material of the present invention, gelatin is advantageously used, but other hydrophilic colloids can be used alone or in combination with gelatin.

In the present invention, gelatin may be lime-treated gelatin or acid-processed gelatin. Details of the manufacture of gelatin is described by Arther Veis in The *Macromolecular Chemistry of Gelatin* (published by Academic Press, 1964).

The color-developing solution to be used in the developing process of the photographic material of the present invention is preferably an aqueous alkaline solution whose major component is an aromatic primary amine-type color developing agent. As the color developing agent, aminophenol-type compounds are useful, and p-phenylenediamine-type compounds are preferably used, typical examples thereof being 3-methyl-4-amino-N,N-diethylaniline, 3-methyl-4-amino-N-ethyl-N-β-hydroxylaniline, 3-methyl-4-amino-N-ethyl-N-β-methanesulfonamidoethylaniline, and 3-methyl-4-amino-N-ethyl-N-β-methoxyethylaniline and their sulfates, hydrochlorides or p-toluenesulfonates. These compounds may be used in combination according to the desired purpose.

Generally the color-developing solution contains pH buffers such as carbonates, borates, or phosphates of alkali metals; antifoggants or development retarders, such as mercapto compounds, benzothiazoles, benzimidazoles, iodides or bromides; and if required, preservatives such as hydroxylamine, diethylhydroxylamine, sulfites, hydrazines, phenylsemicarbazides, triethanolamine, catecholsulfonic acids, and triethylenediamine (1,4-diazabicyclo[2,2,2]octane); organic solvents such as ethylene glycol and diethylene glycol; development accelerators such as benzyl alcohol, polyethylene glycol, quaternary ammonium salts, and amines; dye-forming couplers; competing couplers; fogging agents such as sodium boron hydride; auxiliary developing agents such as 1-phenyl-3-pyrazolidone; thickening agents; and chelate agents, such as aminopolycarboxylic acids, aminopolyphosphonic acids, alkylphosphonic acids, and phosphonocarboxylic acids such as, for example ethylenediaminetetraacetic acid, nitrilotriacetic acid, ethylenetriaminetetraacetic acid, cyclohexanediaminetetraacetic acid, hydroxyethylimidinoacetic acid, 1-hydroxyethylidene-1,1-diphosphonic acid, nitrilo-N,N,N-trimethylenephosphonic acid, ethylenediamine-N,N,N',N'-tetramethylenephosphonic acid, and ethylenediamine-di-(o-hydroxyphenylacetic acid), and their salts.

For reversal processing, a color development is generally carried out after a black-and-white development. For the black-and-white developing solution, known black-and-white-developing agents such as dihydroxybenzenes (e.g., hydroquinone), 3-pyrazolidones (e.g., 1-phenyl-3-pyrazolidone), and aminophenols (e.g., N-methyl-p-aminophenol) may be used alone or in combination with others.

Generally the color-developing solution has a pH of 9 to 12. Although the replenishing amount of the developing solution varies depending on the color photographic material to be processed, generally the replenishing amount is 3 l or below per $m^2$ of the photographic material, and the replenishing amount can be lowered to 500 ml or below if the bromide ion concentration of the replenishing solution is lowered. If it is required to lower the replenishing amount, it is preferable that the area of the processing tank in contact with air is minimized to prevent the solution from evaporating or being oxidized by air. The replenishing amount can also be lowered by suppressing the accumulation of bromide ions in the developing solution.

The photographic emulsion layers are generally subjected to a bleaching process after color development.

The bleaching process can be carried out together with a fixing process (bleach-fixing process), or it can be carried out separately form a fixing process. Further, to quicken the process, bleach-fixing may be carried out after the bleaching process. In accordance with the purpose, the process may be carried out using a bleach-fixing bath having two successive tanks, or a fixing process may be carried out before the bleach-fixing process, or a bleaching process may be carried out after the bleach-fixing process. As the bleaching agent, use can be made of, for example, compounds of polyvalent metals, such as iron (III), cobalt (III), chromium (VI), and copper (II), peracids, quinones, and nitro compounds. As typical bleaching agents, use can be made of ferricyanides; dichromates; organic complex salts of iron (II) or cobalt (III), such as complex salts of aminopolycarboxylic acids, for example ethylenediaminetetraacetic acid, diethylenetriaminetetraacetic acid, cyclohexanediaminetetraacetic acid, methyliminodiacetic acid, 1,3-diaminopropanetetraacetic acid, and glycol ether diamine tetraacetic acid, citric acid, tartaric acid, and malic acid; persulfates; bromates; permanganates; and nitrobenzenes. Of these, aminopolycarboxylic acid iron (III) complex salts, including ethylenediaminetetraacetic acid iron (III) complex salts, including ethylenediaminetetraacetic acid iron (III) complex salts, and persulfates are preferable in view of rapid processing and the prevention of environmental pollution. Further, aminopolycarboxylic acid iron (III) complex salts are particularly useful in a bleaching solution as well as a bleach-fix solution. The pH of the bleaching solution or the bleach-fix solution using these aminopolycarboxylic acid iron (III) complex salts is generally 5.5 to 8, but if it is required to quicken the process, the process can be effected at a lower pH.

In the bleaching solution, the bleach-fix solution, and the baths preceding them a bleach-accelerating solution may be used if necessary. Examples of useful bleach-accelerating agents are compounds having a mercapto group or a disulfide linkage, described in U.S. Pat. No. 3,893,858, West German Patent No. 1,290,812, JP-A No. 95630/1978, and *Research Disclosure* No. 17129 (June 1978); thiazolidine derivatives, described in JP-A No. 140129/1975; thiourea derivatives, described in U.S. Pat. No. 3,706,561; iodide salts, described in JP-A No. 16235/1988; polyoxyethylene compounds, described in West German Patent No. 2,748,430; polyamine compounds, described in JP-B No. 8836/1960; and iodide ions. Of these, compounds having a mercapto group or a disulfide group are preferable in view of higher acceleration effect, and in particular, compounds described in U.S. Pat. No. 3,893,858, West German Patent No. 1,290,812, and JP-A No. 95630/1978 are preferable. Compounds described in U.S. Pat. No. 4,552,834 are preferable. These bleach-accelerating agents may be added into the photographic material. When the color photographic materials for photographing are to be bleach-fixed, these bleach-accelerating agents are particularly effective.

As fixing agent can be mentioned thiosulfates, thiocyanates, thioether-type compounds, thioureas, and large amounts of iodide salts, though the use of thiosulfates is common, and particularly ammonium thiosulfate can be used most widely. It is preferable to use, as a preservative for the bleach fix solution, sulfites, bisulfites, and carbonyl bisulfite adducts.

It is common for the silver halide color photographic material of the present invention to undergo, after a desilvering process such as fixing or bleach-fix, a washing step and/or a stabilizing step. The amount of washing water may be set within a wide range depending on the characteristics (e.g., due to the materials used, such as couplers), the application of the photographic material, the washing temperature, the number of washing tanks (the number of steps), the type of replenishing system, including, for example, the counter-current system and the direct flow system, and other various conditions. Of these, the relationship between the number of water-washing tanks and the amount of washing water in the multi-stage counter-current system can be found according to the method described in *Journal of the Society of Motion Picture and Television Engineers,* Vol. 64, pages 248 to 253 (May 1955).

According to the multi-stage-counter-current system described in the literature mentioned above, although the amount of washing water can be considerably reduced, bacteria propagate with an increase of retention time of the washing water in the tanks, leading to a problem with the resulting suspend matter adhering to the photographic material. In processing the present color photographic material, as a measure to solve this problem, the method of reducing calcium and magnesium described in JP-A No. 288838/1987 can be used quite effectively. Also chlorine-type bactericides such as sodium chlorinated isocyanurate, cyabendazoles, isothiazolone compounds described in JP-A No. 8542/1982, benzotriazoles, and other bactericides described by Hiroshi Horiguchi in *Bokin Bobaizai no Kagaku* (1986) published by Sankyo-Shuppan, *Biseibutsu no Mekkin, Sakkin, Bobaigijutsu* (1982), edited by Eiseigijutsu-kai, published by Kogyogijutsu-kai, and in *Bokin Bobaizai Jiten* (1986), edited by Nihon Bokin Bobai-Gakkai, can be used.

The pH of the washing water used in processing the present photographic material is 4 to 9, preferably 5 to 8. The washing water temperature and the washing time to be set may very depending, for example, on the characteristics and the application of the photographic material, and they are generally selected in the range of 15° to 45° C. for 20 sec. to 10 min., and preferably in the range of 25° to 40° C. for 30 sec. to 5 min. Further, the photographic material of the present invention can be processed directly with a stabilizing solution instead of the above washing. In such a stabilizing process, any of known processes, for example, a multi-step counter-current stabilizing process or its low-replenishing-amount process, described in JP-A Nos. 8543/1982, 14834/1983, and 220345/1985, and an ion-exchanging process can be used.

In some cases, the above washing process is further followed by a stabilizing process, and as an example thereof can be mentioned a stabilizing bath that is used as a final bath for color photographic materials for photography, which contains formalin and a surface-active agent. In this stabilizing bath, each kind of the chelating agents and bactericides may be added.

Any over-flowed solution resulting from a replenishing of washing solution and/or stabilizing solution may be reused in other steps, such as a desilvering step.

The silver halide color photographic material of the present invention may contain therein a color-developing agent for the purpose of simplifying and quickening the process. If they contain such a color-developing agent, it is preferable to use a precursor for the color-developing agent. For example, indoaniline-type compounds described in U.S. Pat. No. 3,342,597, Schiff base-type compounds described in U.S. Pat. No. 3,342,599 and *Research Disclosure* Nos. 14850 and 15159, aldol compounds described in *research Disclosure* No. 13924, metal salt complexes described in U.S. Pat. No. 3,719,492, and urethane-type compounds described in JP-A No. 135628/1978 can be used.

For the purpose of accelerating the color development, the present silver halide color photographic material may contain, if necessary, various 1-phenyl-3-pyrazolidones. Typical compounds are described in JP-A No. 64339/1981, 144547/1982, and 115438/1983.

The various processing solutions used for the present invention are used at 10° to 50° C. Although generally a temperature of 33° to 38° C. is standard, a higher temperature can be used to accelerate the process to reduce the processing time, or a lower temperature can be used to improve the image quality or the stability of the processing solutions. Also, to save the silver of the photographic material, a process using hydrogen peroxide intensification or cobalt intensification described in West German Patent No. 2,226,770 and U.S. Pat. No. 3,674,499 may be carried out.

As a preservative for the processing solution, sulfites, hydroxylamine can be used. Further, an organic preservative can be substituted for these preservatives.

Herein the term "organic preservative" refers to organic compounds that generally, when added to the processing solution for the color photographic material, reduce the speed of deterioration of the aromatic primary amine color-developing agent. That is, organic preservatives include organic compounds having a function to prevent the color-developing agent from being oxidized, for example, with air, and in particular, hydroxylamine derivatives (excluding hydroxylamine, hereinafter the same being applied), hydroxamic acids, hydrazines, hydrazides, phenols, α-hydroxyketones, α-aminoketones, saccharides, monoamines, diamines, polyamines, quaternary ammonium salts, nitroxyradicals, alcohols, oximes, diamide compounds, and condensed cyclic amines are effective organic preservatives. These are disclosed, for example, JP-B No. 30496/1973, in JP-A Nos. 143020/1977, 4235/1988, 30845/1988, 21647/1988, 44655/1988, 53551/1988, 43140/1988, 56654/1988, 58346/1988, 43138/1988, 146041/1988, 44657/1988, and 44656/1988, U.S. Pat. Nos. 3,615,503 and 2,494,903, JP-A Nos. 97953/1989, 186939/1989, 186940/1989, 187557/1989, 306244/1990.

As the other preservative, various metals described, for example, in JP-A Nos. 44148/1982 and 53749/1982, salicylic acids described, for example, in JP-A No. 180588/1984, amines described, for example, in JP-A Nos. 239447/1988, 128340/1988, 186939/1989, 187557/1989, alkanolamines described, for example, in JP-A No. 3532/1979, polyethyleneimines described, for example, in JP-A No. 94349/1981, aromatic polyhydroxyl compounds described, for example, in U.S. Pat. No. 3,746,544 may be included, if needed. It is particularly preferable the addition of alkanolamines such as triethanolamine, dialkylhydroxylamines such as N,N-diethylhydroxylamine and N,N-di(sulfoethyl)hydroxylamine, hydrazine derivatives such as N,N-bis(carboxymethyl)hydrazine, or aromatic polyhydroxyl compounds.

The use of alkanolamines in combination with the dialkylhydroixylamine and/or hydrazine derivatives is preferable in view of stability improvement of the color developer resulting its stability improvement during the continuous processing.

Next, the present invention will be described in more detail in accordance with examples, but the invention is not limited to these Examples.

EXAMPLE 1

8.25 g of YC-1, a coupler for comparison, was weighed, 3.3 g of trioctyl phosphate, as a high-boiling organic solvent, was added thereto, and 25 ml of ethyl acetate was added to dissolve them. The solution was added to 280 g of a 10 % aqueous gelatin solution, and 1.0 g of sodium dodecylbenzenesulfonate was added to emulsify and disperse it. 136 g of silver chlorobromide emulsion (65.4 g of silver per kg of emulsion; silver bromide: 70 mol %) was added to this emulsified dispersion, and then 230 g of a 10 % aqueous gelatin solution and 320 ml of water were added. Finally, 0.8 g of 1-oxy-3,5-dichloro-s-triazine acid sodium salt, as a hardener, was added thereto, and it was applied to a primed triacetylcellulose film base so that the coating amount of silver would be 865 g/m$^2$, thereby preparing Sample 101. In this case, as a protective layer, a gelatin layer in an amount of 1.55 g/m$^2$ was applied on top of the applied layer.

YC-2 to YC-6, couplers for comparison, and couplers of the present invention were applied in the same way as above so that the coated amount of the couplers might be equimolar, thereby preparing Samples 102 to 114.

To assess the thus prepared Samples, the Samples were given gradation exposure for sensitometry using a sensitometer (FWH model, manufactured by Fuji Photo Film Ltd., Co.; the color temperature of the light source: 3200° K.). Exposure was effected such that the exposure time was 0.1 sec and the exposure amount was 250 CMS.

The thus exposed Samples were processed by using the below-mentioned processing steps, the processing solutions having the below-mentioned processing solution compositions, using an automatic processor.

| Processing step | Temperature | Time |
| --- | --- | --- |
| Color-developing | 37° C. | 3 min. 30 sec. |
| Bleach-fixing | 33° C. | 1 min. 30 sec. |
| Water-washing | 24 to 34° C. | 3 min. |
| Drying | 70 to 80° C. | 1 min. |

The compositions of each processing solutions were as follows:

| Color developer | |
| --- | --- |
| Water | 800 ml |
| Diethylenetriaminepentaacetic acid | 1.0 g |
| Nitrilotriacetic acid | 2.0 g |
| Benzyl alcohol | 15 ml |
| Diethylene glycol | 10 ml |
| Sodium sulfite | 2.0 g |
| Potassium bromide | 1.0 g |
| Potassium carbonate | 30 g |
| N-ethyl-N-(β-methanesulfonamidoethyl)-3-methyl-4-aminoaniline sulfate | 4.5 g |
| Hydroxylamine sulfate | 3.0 g |
| Fluorescent brightening agent (WHITEX-4, made by Sumitomo Chemical Ind.) | 1.0 g |
| Water to make | 1000 ml |
| pH | 10.25 |
| Bleach-fixing solution | |
| Water | 400 ml |
| Ammonium thiosulfate (70%) | 150 ml |
| Sodium sulfite | 18 g |
| Iron (III) ammonium ethylenediamine-tetraacetate dihydrate | 55 g |
| Disodium ethylenediaminetetraacetate | 5 g |
| Water to make | 1000 ml |
| pH | 6.70 |

From the curve of the sensitometry in the blue region of each of the obtained samples, the maximum color Dmax and the gradient γ of the tangent line at the concentration of ½ of the Dmax were read.

The results are summarized in Table 1.

The structures of couplers for comparison in Examples 1 to 9 are shown below.

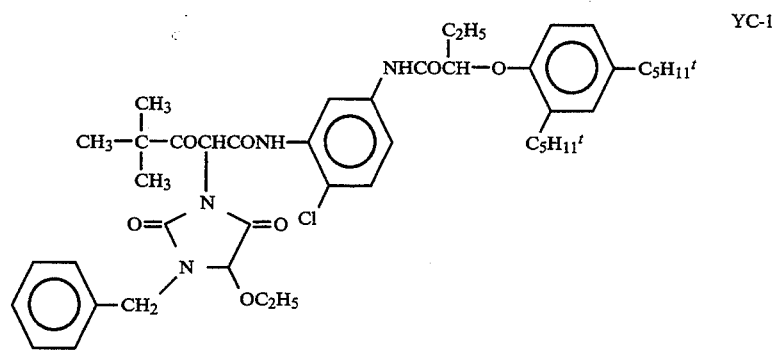
YC-1
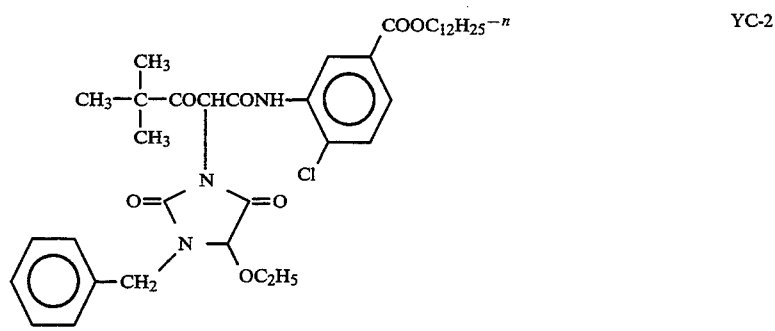
YC-2
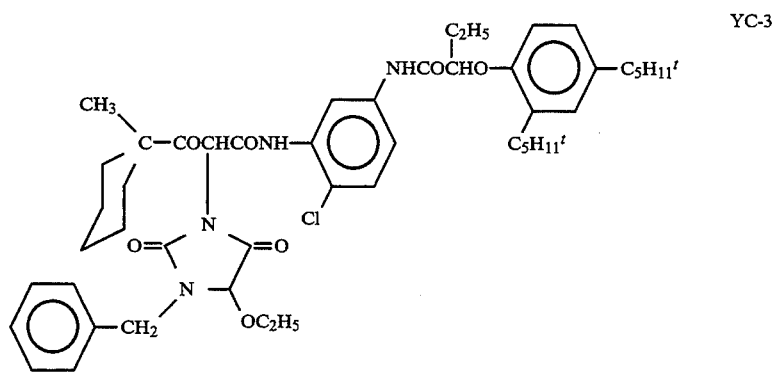
YC-3
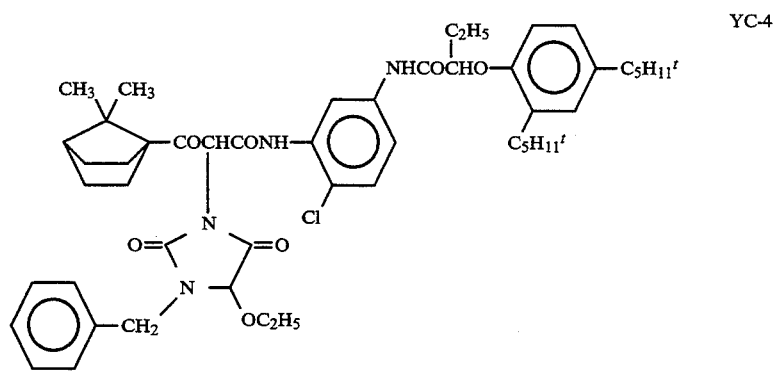
YC-4
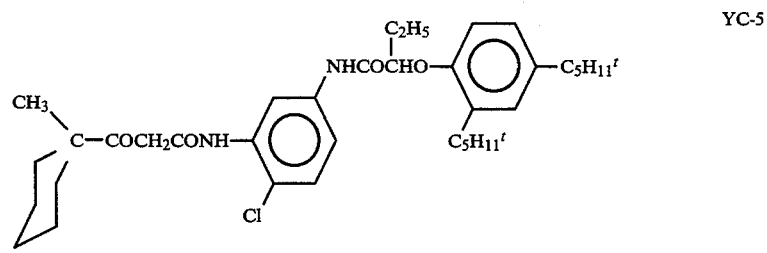
YC-5

-continued

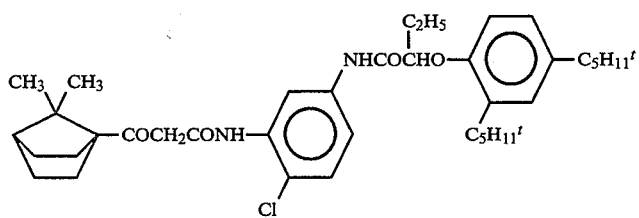
YC-6

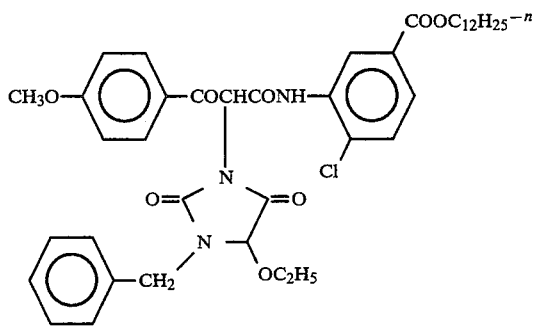
YC-7

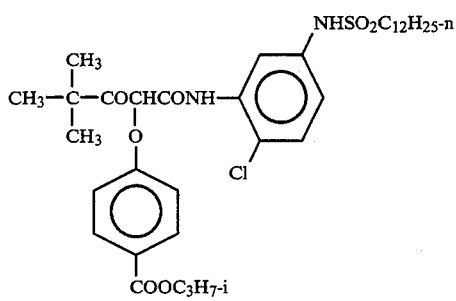
YC-8

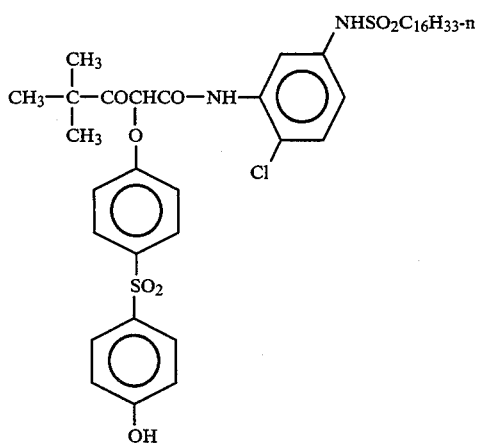
YC-9

TABLE 1

| Sample | Coupler | Dmax | γ | Remarks |
|---|---|---|---|---|
| 101 | YC-1 | 1.58 | 1.04 | Comparative Example |
| 102 | YC-2 | 1.63 | 1.41 | Comparative Example |
| 103 | YC-3 | 1.60 | 1.21 | Comparative Example |
| 104 | YC-4 | 1.43 | 0.92 | Comparative Example |
| 105 | YC-5 | 0.85 | 0.29 | Comparative Example |
| 106 | YC-6 | 0.67 | 0.18 | Comparative Example |
| 107 | Y-1 | 2.04 | 2.01 | This Invention |
| 108 | Y-9 | 2.10 | 2.10 | This Invention |
| 109 | Y-47 | 2.08 | 2.14 | This Invention |
| 110 | Y-8 | 2.06 | 1.97 | This Invention |
| 111 | Y-42 | 1.93 | 1.88 | This Invention |
| 112 | Y-43 | 1.84 | 1.82 | This Invention |
| 113 | Y-44 | 1.97 | 1.97 | This Invention |
| 114 | Y-45 | 1.88 | 1.93 | This Invention |

As is apparent from the results of Table 1, the Dmax of the couplers of the present invention is remarkably great in comparison with that of the comparative examples. Likewise, the γ value of the couplers of the present invention is high, showing that they are highly active couplers.

In particular, it can be said that couplers Y-1, Y-9, Y-47, and Y-8, which have the most preferable coupler structures of the present invention, are couplers which provided excellent performance.

Using some of the above samples that had been color-formed to the maximum density, the transmission absorption spectrum of the films was measured. The results are shown in Table 2.

TABLE 2

| Sample | Coupler | λmax (nm) | Δλ$_{0.5}$ | Δλ$_{0.1}$ | Remarks |
|---|---|---|---|---|---|
| 101 | YC-1 | 444 | 40.3 | 74.3 | Comparative Example |
| 102 | YC-2 | 444 | 39.3 | 72.5 | Comparative Example |
| 103 | YC-3 | 445 | 40.9 | 75.1 | Comparative Example |
| 104 | YC-4 | 446 | 42.1 | 76.3 | Comparative Example |
| 107 | Y-1 | 440 | 37.7 | 73.2 | This Invention (Compared with YC-1) |
| 108 | Y-9 | 440 | 36.7 | 71.0 | This Invention (Compared with YC-2) |
| 109 | Y-47 | 441 | 37.7 | 73.6 | This Invention |

In Table 2, λmax shows the wavelength that gives the maximum absorbance. Δλ$_{0.5}$ and Δλ$_{0.1}$ are respectively differences between the wavelength on the longer wavelength side where the densities of ½ and 1/10 of the maximum density are given and the wavelength giving the maximum density. The smaller these values are, the sharper the absorption on the longer wavelength side is, showing it is a preferable absorption wave form in view of the color reproduction.

The couplers of the present invention show absorption peaks on the shorter wavelength side in comparison with the corresponding comparative couplers (only the acyl part is replaced). The Δλ$_{0.5}$ and Δλ$_{0.1}$ show smaller values in comparison with those of the corresponding comparative couplers. It can be said that these characteristics are preferable characteristics in view of the color reproduction, in that undesired absorption of the magenta to the yellow part is reduced.

From the above, it can be said that the couplers of the present invention are epoch-making couplers high in activity, great in absorbance, and excellent in hue.

EXAMPLE 2

A multilayer photographic material was prepared by multi-coatings composed of the following layer compositions on both-sides of a polyethylene laminated paper base. Coating solutions were prepared as follows:

Preparation of the First Layer Coating Solution

To a mixture of 12.1 g of yellow coupler (YC-1), 4.4 g of image-dye stabilizer (Cpd-1) and 0.7 g of image-dye stabilizer (Cpd-7), 27.2 ml of ethyl acetate and 4.8 g of solvent (Solv-3) were added and dissolved. The resulting solution was dispersed and emulsified in 185 ml of 10% aqueous gelatin solution containing 8 ml of sodium doecylbenzenesulfonate. Separately another emulsion was prepared by adding two kinds of blue-sensitive sensitizing dyes, shown below, to a blend of silver chlorobromide emulsions (cubic grains, 3:7 (silver mol ratio) blend of grains having 0.85 μm and 0.70 μm of average grain size, and a 0.08 and a 0.10 deviation coefficient of grain size distribution, respectively, each in which 0.2 mol % of silver bromide was located at the surface of grains) in such amounts that each dye corresponded to $2.0 \times 10^{-4}$ mol to the large size emulsion and $2.5 \times 10^{-4}$ mol to the small size emulsion, per mol of silver, and then the emulsion was sulfur-sensitized. The thus-prepared emulsion arid the above-obtained emulsified dispersion were mixed together dissolved to give the composition shown below, thereby preparing the first-layer coating solution.

Coating solutions for the second to seventh layers were also prepared in the same manner as the first-layer coating solution. As a gelatin hardener for the respective layers, 1-hydroxy-3,5-dichloro-s-triazine sodium salt was used.

As spectral-sensitizing dyes for the respective layers, the following compounds were used:

Blue-Sensitive Emulsion Layer:

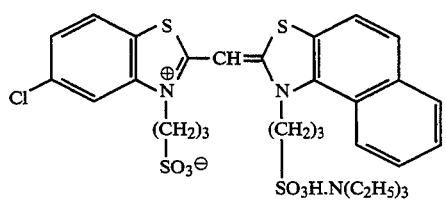

and

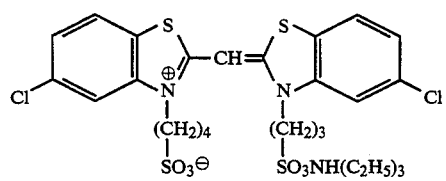

(each $2.0 \times 10^{-4}$ mol to the large size emulsion and $2.5 \times 10^{-4}$ mol to the small size emulsion, per reel of silver halide).

Green-Sensitive Emulsion Layer:

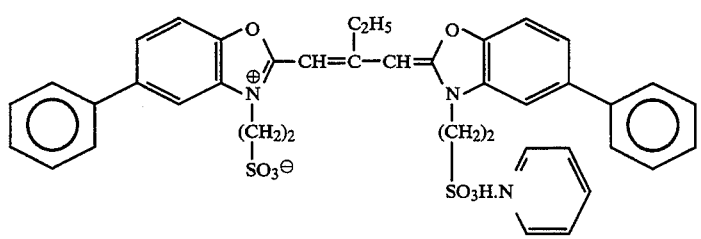

($4.0 \times 10^{-4}$ mol to the large size emulsion and $5.6 \times 10^{-4}$ mol to the small size emulsion, per mol of silver halide) and

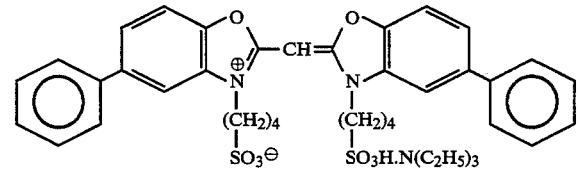

($7.0 \times 10^{-5}$ mol to the large size emulsion and $1.0 \times 10^{-5}$ mol to the small size emulsion, per mol of silver halide).

Red-Sensitive Emulsion Layer:

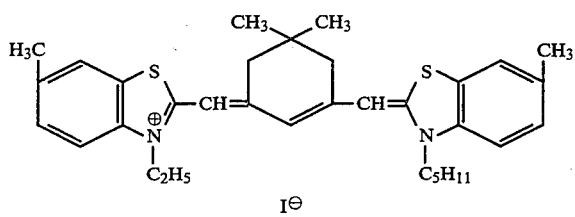

($0.9 \times 10^{-4}$ mol to the large size emulsion and $1.1 \times 10^{-4}$ mol to the small size emulsion, per mol of silver halide).

To the red-sensitive emulsion layer, the following compound was added in an amount of $2.6 \times 10^{-3}$ mol per mol of silver halide:

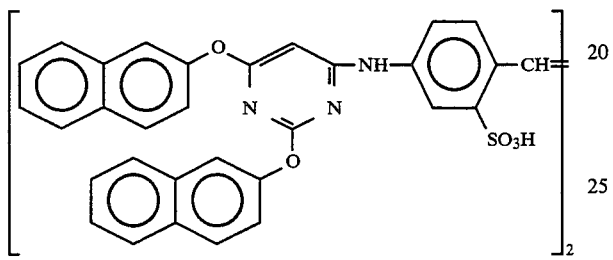

Further, 1-(5-methylureidophenyl)-5-mercaptotetrazole was added to the blue-sensitive emulsion layer, the green-sensitive emulsion layer, and red-sensitive emulsion layer in amounts of $8.5 \times 10^{-5}$ mol, $7.7 \times 10^{-4}$ mol, and $2.5 \times 10^{-4}$ mol, per mol of silver halide, respectively.

The dyes shown below were added to the emulsion layers for prevention of irradiation:

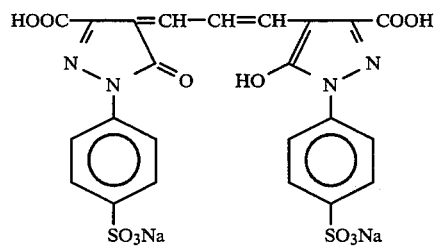

and

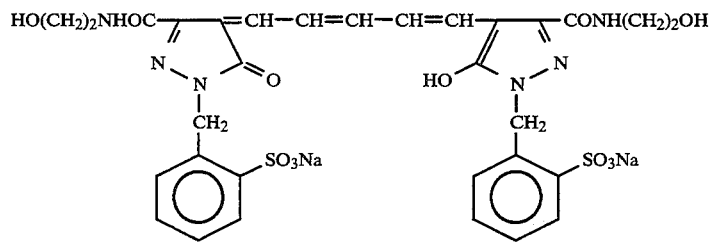

Composition of Layers

The composition of each layer is shown below. The figure represent coating amount (g/m$^2$). The coating amount of each silver halide emulsion is given in terms of silver.

| | |
|---|---|
| Supporting Base | |
| Paper laminated on both sides with polyethylene (a white pigment, TiO$_2$, and a bluish dye, ultramarine, were included in the first layer side of the polyethylene-laminated film.) | |
| First Layer (Blue-sensitive layer) | |
| The above-described silver chlorobromide emulsion | 0.30 |
| Gelatin | 1.86 |
| Yellow coupler (YC-1) | 0.52 |
| Image-dye stabilizer (Cpd-1) | 0.19 |
| Solvent (Solv-3) | 0.35 |
| Image-dye stabilizer (Cpd-7) | 0.06 |
| Second layer (Color-mix preventing layer) | |
| Gelatin | 0.99 |
| Color-mix inhibitor (Cpd-5) | 0.08 |
| Solvent (Solv-1) | 0.16 |
| Solvent (Solv-4) | 0.08 |
| Third layer (Green-sensitive emulsion layer): | |
| Silver chlorobromide emulsions (cubic grains, 1:3 (Ag mol ratio) blend of grains having 0.55 μm and 0.39 μm of average grain size, and a 0.10 and a 0.08 deviation coefficient of grain size distribution, respectively, each in which 0.8 mol % of AgBr was located at the surface of grains | 0.12 |
| Gelatin | 1.24 |
| Magenta coupler (ExM) | 0.20 |
| Image-dye stabilizer (Cpd-2) | 0.03 |
| Image-dye stabilizer (Cpd-3) | 0.15 |
| Image-dye stabilizer (Cpd-4) | 0.02 |
| Image-dye stabilizer (Cpd-9) | 0.02 |
| Solvent (Solv-2) | 0.40 |
| Fourth layer (Ultraviolet ray absorbing layer): | |
| Gelatin | 1.58 |
| Ultraviolet absorber (UV-1) | 0.47 |
| Color-mix inhibitor (Cpd-5) | 0.05 |
| Solvent (Solv-5) | 0.24 |
| Fifth layer (Red-sensitive emulsion layer): | |
| Silver chloride emulsions (cubic grains, 1:4 (Ag mol ratio) blend of grains having 0.58 μm and 0.45 μm of average grain size, and a 0.09 and a 0.11 deviation coefficient of grain size distribution, respectively, each in which 0.6 mol % of AgBr was located at the surface of grains) | 0.23 |
| Gelatin | 1.34 |
| Cyan coupler (ExC) | 0.32 |
| Image-dye stabilizer (Cpd-6) | 0.17 |
| Image-dye stabilizer (Cpd-7) | 0.40 |
| Image-dye stabilizer (Cpd-8) | 0.04 |
| Solvent (Solv-6) | 0.15 |

| Sixth layer (Ultraviolet ray absorbing layer): | |
|---|---|
| Gelatin | 0.53 |
| Ultraviolet absorber (UV-1) | 0.16 |
| Color-mix inhibitor (Cpd-5) | 0.02 |
| Solvent (Solv-5) | 0.08 |

Seventh layer (Protective layer):

| | |
|---|---|
| Gelatin | 1.33 |
| Acryl-modified copolymer of polyvinyl alcohol (modification degree: 17%) | 0.17 |
| Liquid paraffin | 0.03 |

Compounds used are as follows:

(ExY) Yellow coupler

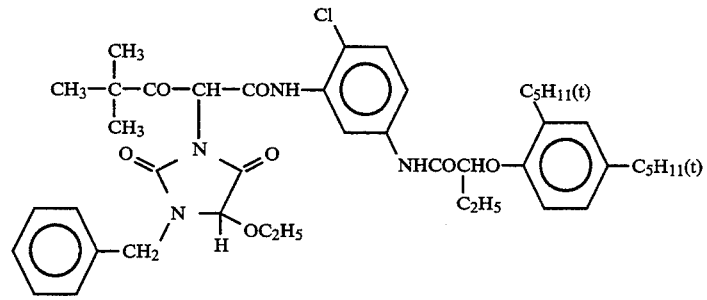

(ExM) Magenta coupler
Mixture (1:1 in molar ratio) of

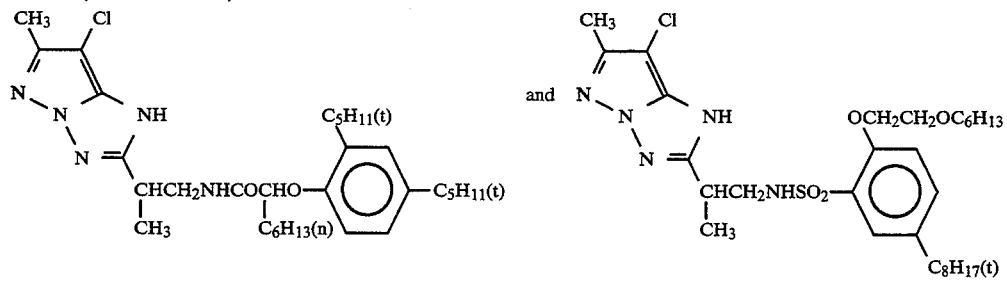

(ExC) Cyan coupler
Mixture (2:4:4 in weight ratio) of R = $C_2H_5$ and $C_4H_9$ of

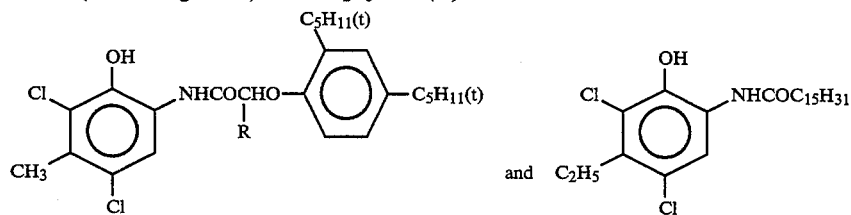

(Cpd-1) Image-dye stabilizer

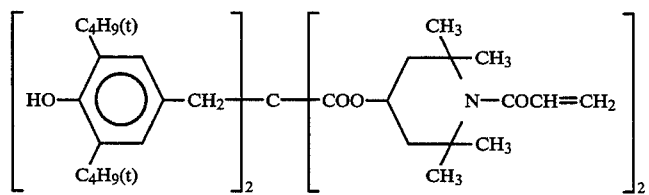

(Cpd-2) Image-dye stabilizer

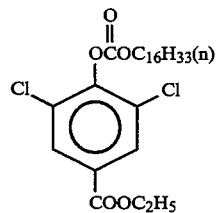

(Cpd-3) Image-dye stabilizer

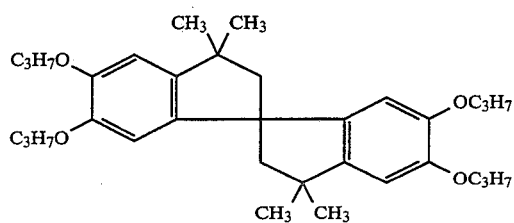
(Cpd-4) Image-dye stabilizer
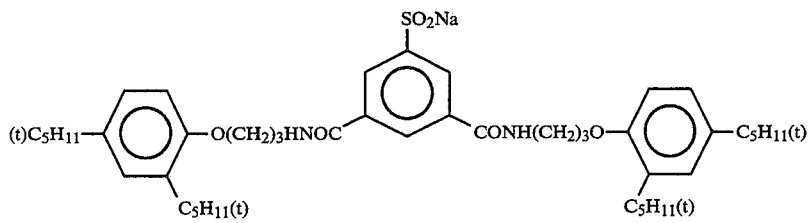
(Cpd-5) Color-mix inhibiter
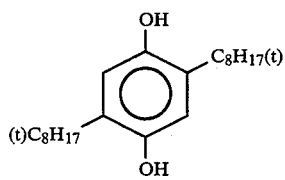
(Cpd-6) Image-dye stabilizer
Mixture (2:4:4 in weight ratio) of
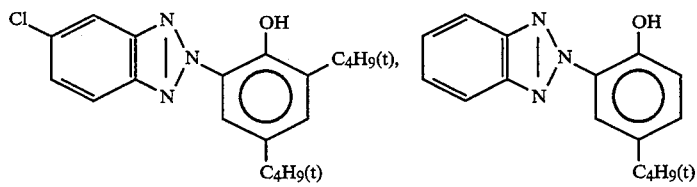
and
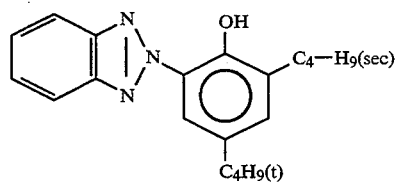
(Cpd-7) Image-dye stabilizer
$\mathrm{+CH_2-CH\!\!\!\!)_{\overline{n}}}$
  |
  $\mathrm{CONHC_4H_9(n)}$
Average molecular weight: 60,000
(Cpd-8) Image-dye stabilizer
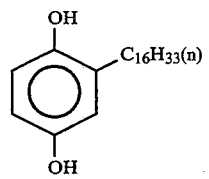
(Cpd-9) Image-dye stabilizer

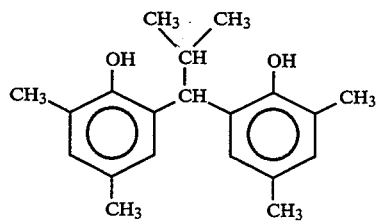

(UV-1) Ultraviolet ray absorber
Mixture (4:2:4 in weight ratio) of

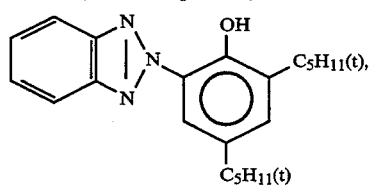 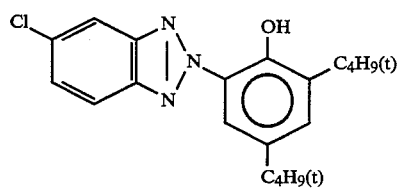

and

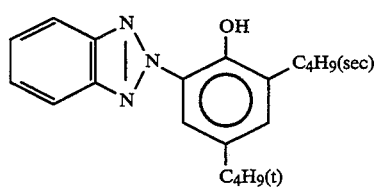

(Solv-1) Solvent

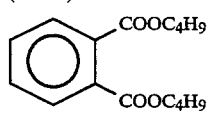

(Solv-2) Solvent
Mixture (2:1 in volume ratio) of

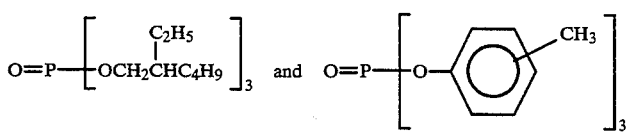

(Solv-3) Solvent
O=P$+$O—C$_9$H$_{19}$(iso)]$_3$ (Solv-4) Solvent

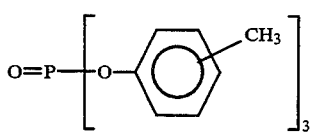

(Solv-5) Solvent
COOC$_8$H$_{17}$
|
(CH$_2$)$_8$
|
COOC$_8$H$_{17}$ (Solv-6) Solvent

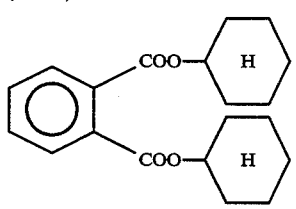

The thus-obtained sample was designated as Sample 1. Samples 202 to 212 were prepared in the same manner as Sample 1. except that yellow coupler was changed to comparative couplers YC-2 to YC-4 and couplers of the present invention, respectively.

The processing method of these samples will be described below.

Each of samples was subjected to a gradation exposure through three color separated filters for sensitometry using a sensitometer (FWH model made by Fuji Photo Film Co., Ltd., the color temperature of light source was 3200 K). At that time, the exposure was coducted in such a manner that the exposure was 250 CMS with the exposure time being 0.1 sec.

After exposure to light, each sample was subjected to a continouos processing (running test) of the processing process shown below using a paper-processer, until a volume of color-developer twice that of a tank had been replenished.

| Processing Process | Temperature (° C.) | Time (sec.) | Replenisher (ml)* | Tank volume (l) |
|---|---|---|---|---|
| Color developing | 35 | 45 | 161 | 17 |
| Bleach-fixing | 30–35 | 45 | 214 | 17 |
| Rinsing (1) | 30–35 | 20 | — | 10 |
| Rinsing (2) | 30–35 | 20 | — | 10 |
| Rinsing (3) | 30–35 | 20 | — | 10 |
| Drying | 70–80 | 60 | | |

Note:
*Replenishing amount per m² of photographic material. (Rinsing processes were carried out in 3-tanks counter-current flow system from tank of rinsing (3) toward tank of rinsing (1).)

The compositions of each processing solution were as follows:

|  | Tank Solution | Replenisher |
|---|---|---|
| Color developer | | |
| Water | 800 ml | 800 ml |
| Ethylenediamine-N, N, N, N-tetramethylenephosphonic acid | 1.5 g | 2.0 g |
| Triethanolamine | 8.0 g | 12.0 g |
| Sodium chloride | 1.4 g | — |
| Potassium carbonate | 25 g | 25 g |
| N-ethyl-N-(β-methanesulfonamidoethyl)-3-methyl-4-aminoaniline sulfonate | 5.0 g | 7.0 g |
| N,N-Bis(carboxymethyl)hydrazine | 5.5 g | 7.0 g |
| Fluorescent brightening agent (WHITEX-4, made by Sumitomo Chemical Ind. Co.) | 1.0 g | 3.5 g |
| Water to make | 1000 ml | 1000 ml |
| ph (25° C.) | 10.05 | 10.45 |
| Bleach-fixing solution | | |
| (Both tank solution and replenisher) | | |
| Water | | 400 ml |
| Ammonium thiosulfate (70%) | | 100 ml |
| Sodium sulfite | | 17 g |
| Iron (III) ammonium ethylenediamine- | | 55 g |
| Disodium ethylenediaminetetraacetate | | 5 g |
| Ammonium bromide | | 40 g |
| Water to make | | 1000 ml |
| pH (25° C.) | | 6.0 |
| Rinsing solution | | |
| (Both tank solution and replenisher) | | |
| Ion-exchanged water (Calcium and magnesium each are contained in an amount of 3 ppm or below) | | |

The evaluation was carried out at the maximum color density Dmax. The drop of the Dmax at the time when sodium sulfite, as a competing compound was added to the color developer in an amount of 0.5 g of per liter was designated as ΔDmax. The results are shown in Table 3.

TABLE 3

| Sample | Coupler | Dmax | ΔDmax | Remarks |
|---|---|---|---|---|
| 201 | YC-1 | 1.88 | −0.36 | Comparative Example |
| 202 | YC-2 | 1.94 | −0.23 | Comparative Example |
| 203 | YC-3 | 1.91 | −0.30 | Comparative Example |
| 204 | YC-4 | 1.72 | −0.48 | Comparative Example |
| 205 | Y-1 | 2.20 | −0.12 | This Invention |
| 206 | Y-9 | 2.28 | −0.09 | This Invention |
| 207 | Y-47 | 2.25 | −0.10 | This Invention |
| 208 | Y-8 | 2.24 | −0.10 | This Invention |
| 209 | Y-42 | 2.13 | −0.12 | This Invention |
| 210 | Y-43 | 2.09 | −0.14 | This Invention |
| 211 | Y-44 | 2.10 | −0.14 | This Invention |
| 212 | Y-45 | 2.07 | −0.16 | This Invention |

As is apparent from Table 3, it can be said that the couplers of the present invention are high in Dmax and color-forming properties in comparison with the comparative examples. When a competing compound is added, the drop of the density for the coupler of this invention is small, so that it can be said that the couplers of the present invention are highly active couplers. It can be said that such couplers are excellent couplers that can provide stable finish against the fluctuation of the composition of a processing solution.

In particular, Y-1, Y-9, Y-47, and Y-8, which fall in the range of the most preferable couplers of the present invention show a particularly excellent performance.

EXAMPLE 3

15.0 g of YC-1, a coupler for comparison, was weighed, 5.0 g of tricresyl phosphate as a high-boiling organic solvent was added thereto, and 15 ml of ethyl acetate was added to dissolve them. The solution was added to 200 g of a 10 wt. % of aqueous gelatin solution containing 1.5 g of sodium dodecylbenzenesulfonate to emulsify and disperse it.

All amount of thus-prepared emulsified emulsion was added to 310 g of silver iodobromide emulsion (emulsion containing 70.0 g/kg of silver and 10 mol % of silver iodide), and it was applied to a prime-coated triacetate cellulose film base so that the coating amount of silver would be 1.61 g/m². On this coating layer, a gelatin layer as a protective layer was provided so that the dried thickness of the layer would be 1.0 μm, thereby preparing sample 301. As a gelatin hardener 1,2-bis(vinylsulfonylacetoamido)ethane was used.

The thus-prepared samples were processed, after an exposure to light, according to the process shown below.

| | Processing process | |
|---|---|---|
| Process | Time | Temperature |
| Color developing | 3 min. 15 sec. | 38° C. |
| Bleaching | 1 min. | 38° C. |
| Bleach-fixing | 3 min. 15 sec. | 38° C. |
| Water-washing (1) | 40 sec. | 35° C. |
| Water-washing (2) | 1 min. | 35° C. |
| Stabilizing | 40 sec. | 38° C. |
| Drying | 1 min. 15 sec. | 55° C. |

The composition of each processing solution was as follows:

| | (g) |
|---|---|
| Color developer | |
| Diethylenetriaminepentaacetic acid | 1.0 |
| 1-hydroxyethylidene-1,1-diphosphonic acid | 3.0 |

-continued

| | (g) |
|---|---|
| Sodium sulfite | 4.0 |
| Potassium carbonate | 30.0 |
| Potassium bromide | 1.4 |
| Potassium iodide | 1.5 mg |
| Hydroxylamine sulfate | 2.4 |
| 4-(N-Ethyl-N-$\beta$-hydroxyethylamino)-2-methyl-4-aminoaniline sulfate | 4.5 |
| Water to make | 1.0 l |
| pH | 10.05 |
| Bleaching solution | |
| Iron (III) ammonium ethylenediamine-tetraacetate dihydrate | 120.0 |
| Disodium ethylenediaminetetraacetate | 10.0 |
| Ammonium bromide | 100.0 |
| Ammonium nitrate | 10.0 |
| Bleaching accelerator | 0.005 mol |

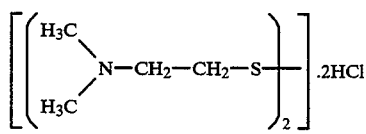

| | |
|---|---|
| Aqueous ammonia (27%) | 15.0 ml |
| Water to make | 1.0 l |
| pH | 6.3 |
| Bleach-fixing solution | |
| Iron (III) ammonium ethylenediamine-tetraacatate dihydrate | 50.0 |
| Disodium ethylenediaminetetraacetate | 5.0 |
| Sodium sulfite | 12.0 |
| Ammonium thiosulfate (70%) | 240.0 ml |
| Aqueous ammonia (27%) | 6.0 ml |
| Water to make | 1.0 l |
| pH | 7.2 |
| Washing solution | |
| Tap water was treated by passage through a hybrid-type column filled with a H-type strong acidic cation-exchange resin (Amberlite IR-120B, tradename, made by Rohm & Haas) and on OH-type strong alkaline anion-exchange resin (Amberlite IR-400, tradename made by the same as the above) so that each concentration of calcium and magnesium ions would be 3 mg/l or below, followed by addition of 20 mg/l of sodium dichloroisocyanurate and 0.15 g/l of sodium sulfate. The pH of this solution is in a range of 6.5 to 7.5. | |
| Stabilizing solution | |
| Formalin (37%) | 2.0 ml |
| Polyoxyethylene-p-mononylphenylether (average polimerization degree: 10) | 0.3 |
| Disodium ethylenediaminetetraacetate | 0.05 |
| Water to make | 1.0 l |
| pH | 5.0–8.0 |

Samples 302 to 309 were prepared by the same method of coating as the above, except that the coupler was changed to the other comparative couplers and couplers of the present invention, respectively, so as to be an equimolar coating amount.

Results are shown in Table 4.

TABLE 4

| Sample | Coupler | Dmax | Remarks |
|---|---|---|---|
| 301 | YC-7 | 2.83 | Comparative Example |
| 302 | YC-9 | 2.45 | Comparative Example |
| 303 | YC-2 | 2.39 | Comparative Example |
| 304 | YC-3 | 2.04 | Comparative Example |
| 305 | Y-9 | 3.12 | This invention |
| 306 | Y-12 | 3.07 | This invention |
| 307 | Y-47 | 3.09 | This invention |
| 308 | Y-44 | 3.01 | This invention |
| 309 | Y-45 | 2.96 | This invention |

As is apparent from the results in Table 4, in comparison with the couplers YC-9, YC-2, and YC-3 of the pivaloyl type, the couplers of the present invention give remarkably high high color densities. Further, it can be understood that the couplers of the present invention are excellent couplers that give color densities higher than that of coupler YC-7 of the benzoyl type that was conventionally considered high in color density.

EXAMPLE 4

Multilayer color photographic material sample 401 was prepared by multi-coating each layer having a composition as shown below on a prime-coated triacetate cellulose film base.

Composition of Photosensitive Layer

The figure corresponding to each component is indicated in the coating in an amount of $g/m^2$, but the coating amount of silver halide emulsion is indicated in terms of silver. As respects the sensitizing dyes, the coating amount is indicated in mol per mol of silver halide in the same layer.

| (Sample 401) | |
|---|---|
| First layer (Halation preventing layer) | |
| Black colloidal silver silver | silver 0.18 |
| Gelatin | 1.40 |
| Second layer (Intermediate layer) | |
| 2.5-Di-t-pentadecylhydroquinin | 0.81 |
| EX-1 | 0.07 |
| EX-3 | 0.02 |
| EX-12 | 0.002 |
| U-1 | 0.06 |
| U-2 | 0.08 |
| U-3 | 0.10 |
| HBS-1 | 0.10 |
| HBS-2 | 0.02 |
| Gelatin | 1.04 |
| Third layer (First red-sensitive emulsion layer) | |
| Emulsion A | silver 0.25 |
| Emulsion B | silver 0.25 |
| Sensitizing dye I | $6.9 \times 10^{-5}$ |
| Sensitizing dye II | $1.8 \times 10^{-5}$ |
| Sensitizing dye III | $3.1 \times 10^{-4}$ |
| EX-2 | 0.035 |
| EX-10 | 0.020 |
| U-1 | 0.070 |
| U-2 | 0.050 |
| U-3 | 0.070 |
| HBS-1 | 0.060 |
| Gelatin | 0.87 |
| Fourth layer (Second red-sensitive emulsion layer) | |
| Emulsion G | silver 1.0 |
| Sensitizing dye I | $5.1 \times 10^{-5}$ |
| Sensitizing dye II | $1.4 \times 10^{-5}$ |
| Sensitizing dye III | $2.3 \times 10^{-4}$ |
| EX-2 | 0.400 |
| EX-3 | 0.020 |
| EX-4 | 0.030 |
| EX-10 | 0.015 |
| U-1 | 0.070 |
| U-2 | 0.050 |
| U-3 | 0.070 |
| Gelatin | 1.30 |
| Fifth layer (Third red-sensitive emulsion layer) | |
| Emulsion D | silver 1.60 |
| Sensitizing dye I | $5.4 \times 10^{-5}$ |
| Sensitizing dye II | $1.4 \times 10^{-5}$ |
| Sensitizing dye III | $2.4 \times 10^{-4}$ |
| EX-3 | 0.010 |
| EX-4 | 0.080 |
| EX-2 | 0.097 |
| HBS-1 | 0.22 |
| HBS-2 | 0.10 |
| Gelatin | 1.63 |
| Sixth layer (Intermediate layer) | |

-continued

| (Sample 401) | |
|---|---|
| EX-5 | 0.040 |
| HBS-1 | 0.020 |
| Gelatin | 0.80 |
| Seventh layer (First green-sensitive emulsion layer) | |
| Emulsion A | silver 0.15 |
| Emulsion B | silver 0.15 |
| Sensitizing dye V | $3.0 \times 10^{-5}$ |
| Sensitizing dye VI | $1.0 \times 10^{-4}$ |
| Sensitizing dye VII | $3.8 \times 10^{-4}$ |
| EX-6 | 0.260 |
| EX-1 | 0.021 |
| EX-7 | 0.030 |
| EX-8 | 0.025 |
| HBS-1 | 0.100 |
| HBS-3 | 0.010 |
| Gelatin | 0.63 |
| Eighth layer (Second green-sensitive emulsion layer) | |
| Emulsion C | silver 0.45 |
| Sensitizing dye V | $2.1 \times 10^{-5}$ |
| Sensitizing dye VI | $7.0 \times 10^{-5}$ |
| Sensitizing dye VII | $2.6 \times 10^{-4}$ |
| EX-6 | 0.094 |
| Ex-8 | 0.018 |
| Ex-7 | 0.026 |
| HBS-1 | 0.160 |
| HBS-3 | 0.008 |
| Gelatin | 0.50 |
| Ninth layer (Third green-sensitive emulsion layer) | |
| Emulsion E | silver 1.2 |
| Sensitizing dye V | $3.5 \times 10^{-5}$ |
| Sensitizing dye VI | $8.0 \times 10^{-5}$ |
| Sensitizing dye VII | $3.0 \times 10^{-4}$ |
| EX-13 | 0.015 |
| Ex-11 | 0.100 |
| Ex-1 | 0.025 |
| HBS-1 | 0.25 |
| HBS-2 | 0.10 |
| Gelatin | 1.54 |
| Tenth layer (Yellow filter layer) | |
| Yellow colloidal silver | silver 0.05 |
| EX-5 | 0.08 |

| (Sample 401) | |
|---|---|
| HBS-1 | 0.03 |
| Gelatin | 0.95 |
| Eleventh layer (First blue-sensitive layer) | |
| Emulsion A | silver 0.08 |
| Emulsion B | silver 0.07 |
| Emulsion F | silver 0.07 |
| Sensitizing dye VIII | $3.5 \times 10^{-4}$ |
| EX-9 | 0.721 |
| EX-8 | 0.042 |
| HBS-1 | 0.28 |
| Gelatin | 1.10 |
| Twelfth-layer (Second blue-sensitive emulsion layer) | |
| Emulsion G | silver 0.45 |
| Sensitizing dye VIII | $2.1 \times 10^{-4}$ |
| EX-9 | 0.154 |
| Ex-10 | 0.007 |
| HBS-1 | 0.05 |
| Gelatin | 0.78 |
| Thirteenth layer (Third blue-sensitive emulsion layer) | |
| Emulsion H | silver 0.77 |
| Sensitizing dye VIII | $2.2 \times 10^{-4}$ |
| EX-9 | 0.20 |
| HBS-1 | 0.07 |
| Gelatin | 0.69 |
| Fourteenth layer (First protective layer) | |
| Emulsion I | silver 0.20 |
| U-4 | 0.11 |
| U-5 | 0.17 |
| HBS-1 | 0.05 |
| Gelatin | 1.00 |
| Fifteenth layer (Second protective layer) | |
| Poly(methyl methacrylate) particle (diameter: about 1.5 μm) | 0.54 |
| S-1 | 0.20 |
| Gelatin | 1.20 |

In each layer gelatin hardener H-1 and surface-active agent were added in addition to the above components.

| Emulsion | Average AgI Content (%) | Grain Size Average Diameter (μm) | Grain Size Deviation Coefficient (%) | Ratio of Diameter/ Thickness | Ratio of Silver Amount (AgI content %) |
|---|---|---|---|---|---|
| A | 4.0 | 0.45 | 27 | 1 | Core/Shell = 1/3(13/1) Double Structure Grains |
| B | 8.9 | 0.70 | 14 | 1 | Core/Shell = 3/7(25/2) Double Structure Grains |
| C | 10 | 0.75 | 30 | 2 | Core/Shell = 1/2(24/3) Double Structure Grains |
| D | 16 | 1.05 | 35 | 2 | Core/Shell = 1/2(40/0) Double Structure Grains |
| E | 10 | 1.05 | 35 | 3 | Core/Shell = 1/2(24/3) Double Structure Grains |
| F | 4.0 | 0.25 | 28 | 1 | Core/Shell = 1/3(13/1) Double Structure Grains |
| G | 11.0 | 0.75 | 25 | 2 | Core/Shell = 1/2(40/0) Double Structure Grains |
| H | 14.5 | 1.30 | 25 | 3 | Core/Shell = 37/63(34/3) Double Structure Grains |
| I | 1 | 0.07 | 15 | 1 | Uniform Grains |

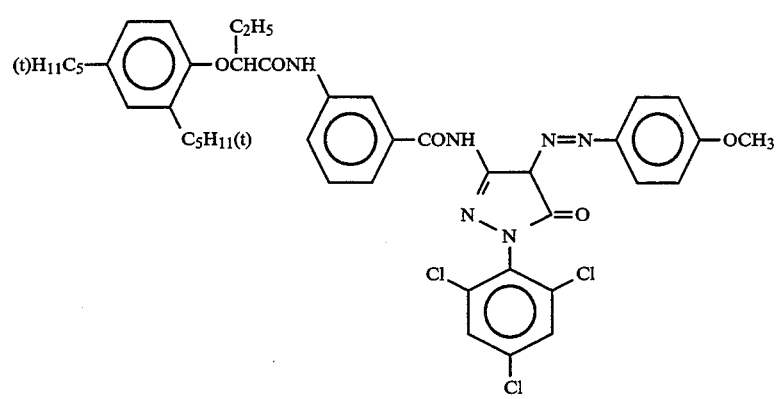

EX-1

-continued
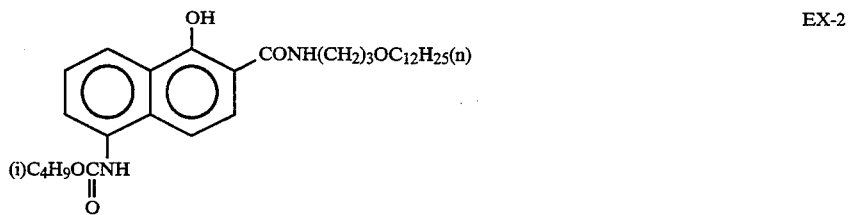
EX-2
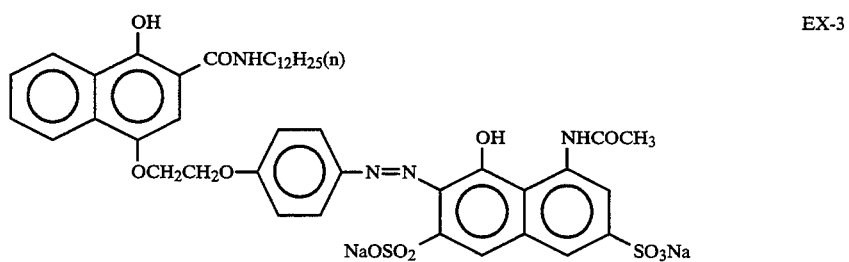
EX-3
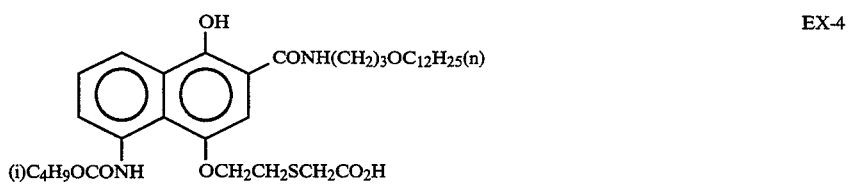
EX-4
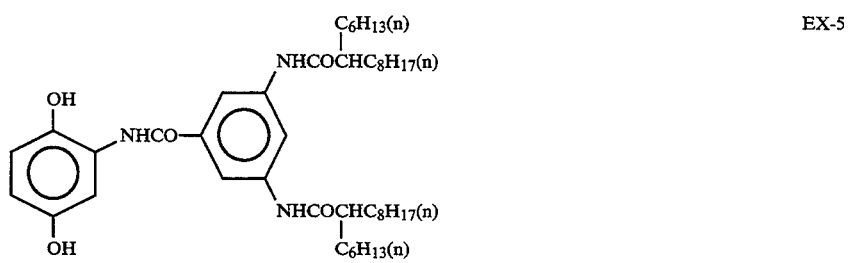
EX-5
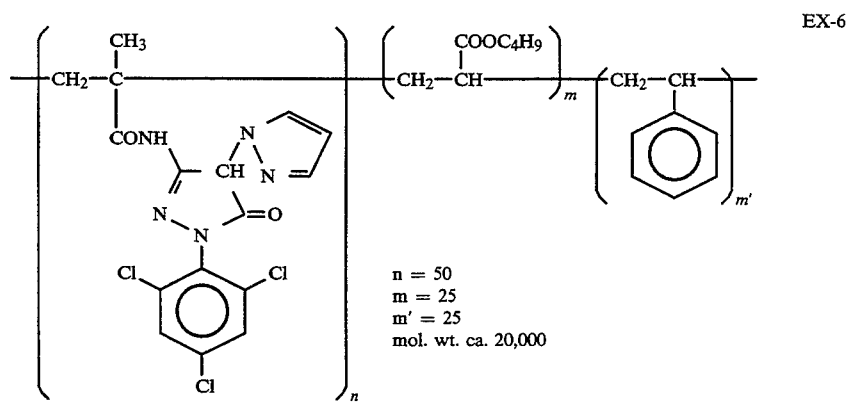
EX-6
n = 50
m = 25
m' = 25
mol. wt. ca. 20,000

-continued
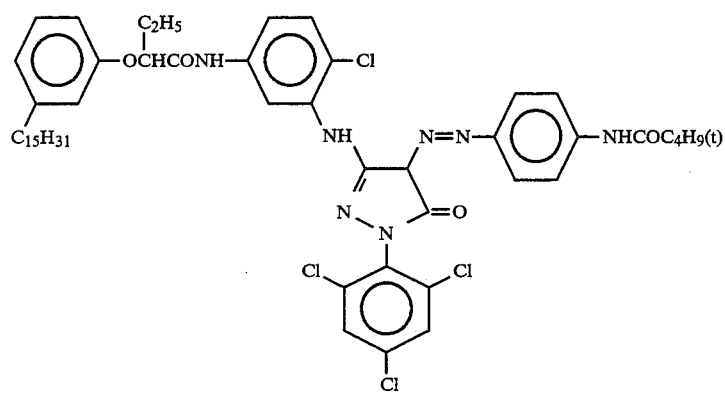
EX-7
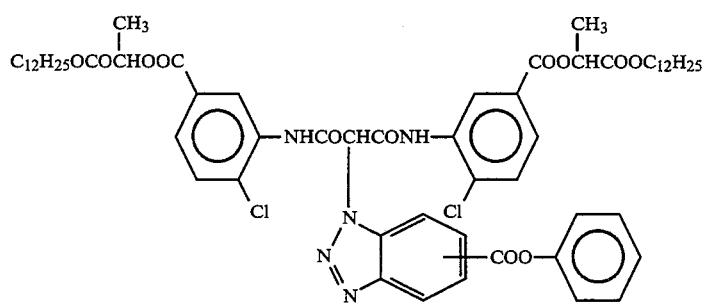
EX-8
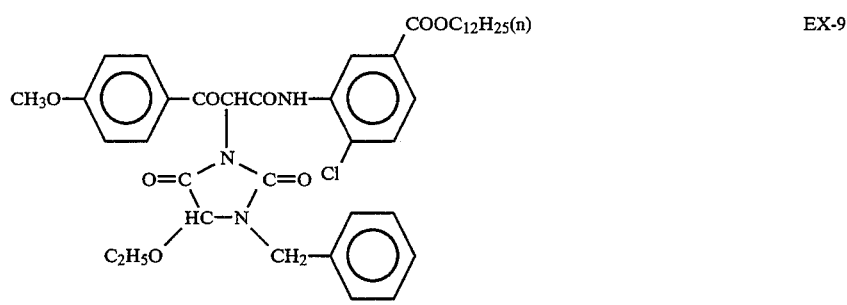
EX-9
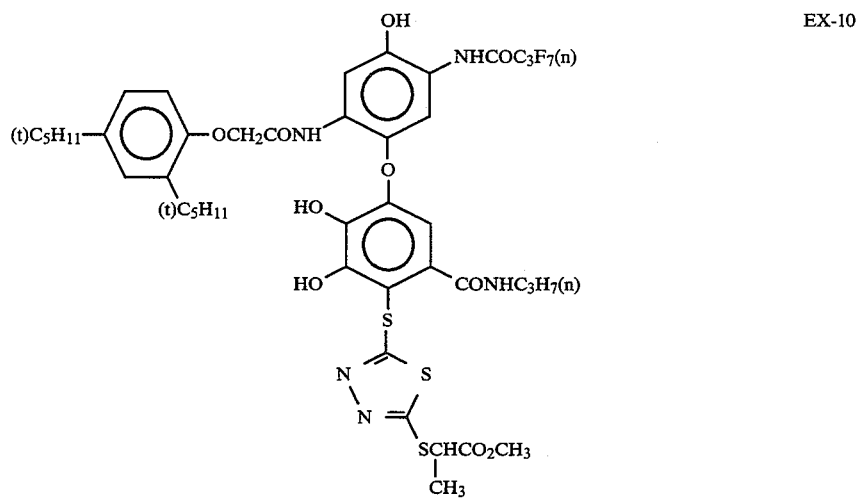
EX-10

-continued
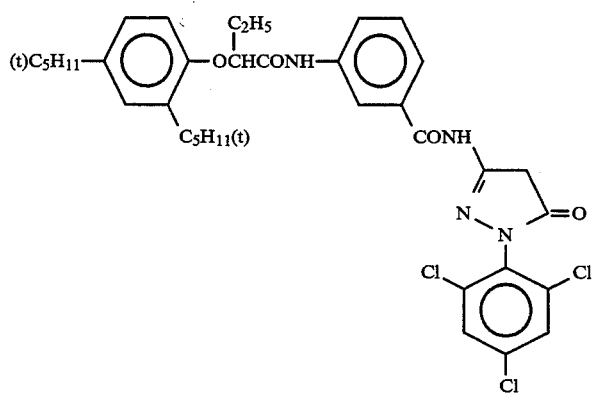
EX-11
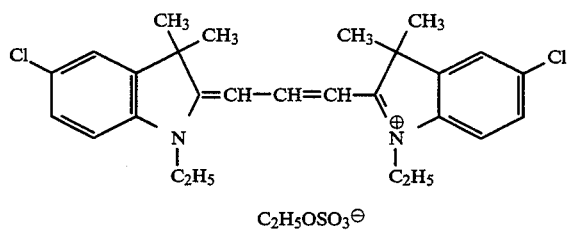
EX-12
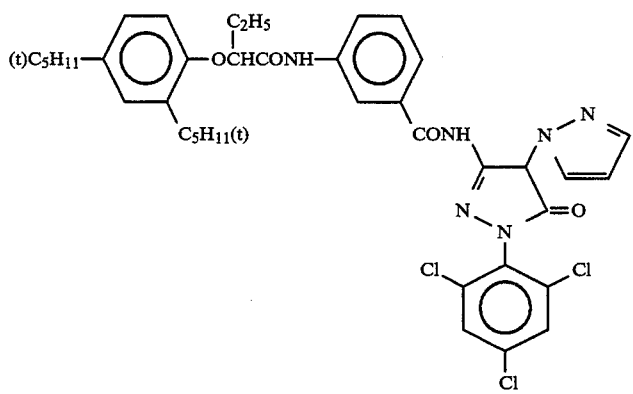
EX-13
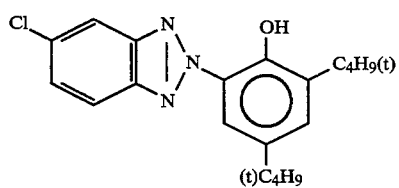
U-1
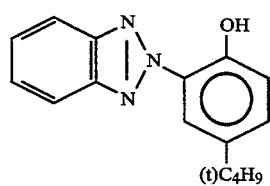
U-2
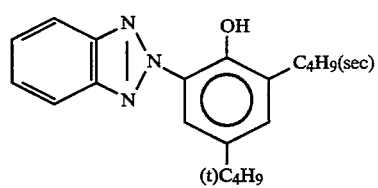
U-3

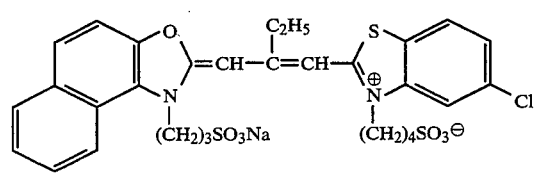
Sensitizing Dye I
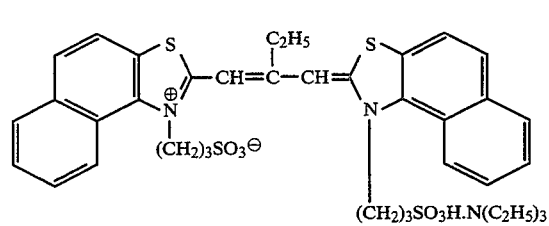
Sensitizing Dye II
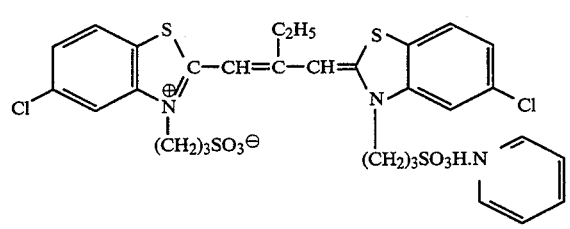
Sensitizing Dye III
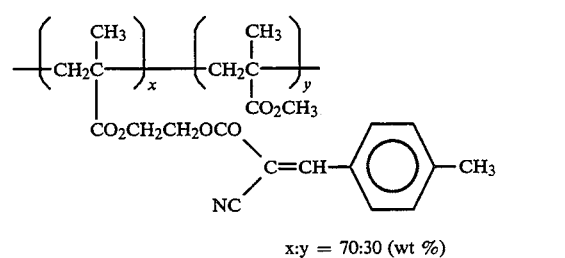
U-4
x:y = 70:30 (wt %)
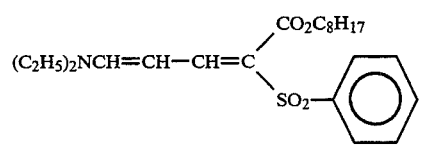
UV-5
Tricrezyl Phosphate  HBS-1
Di-n-Butyl Phthalate  HBS-2
HBS-3
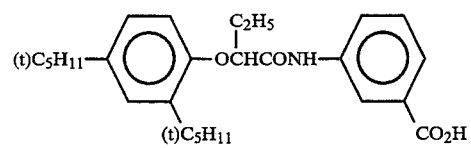
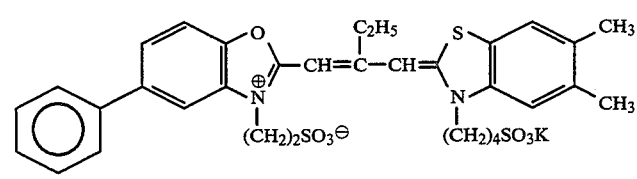
Sensitizing Dye V
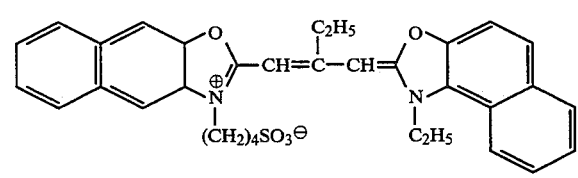
Sensitizing Dye VI

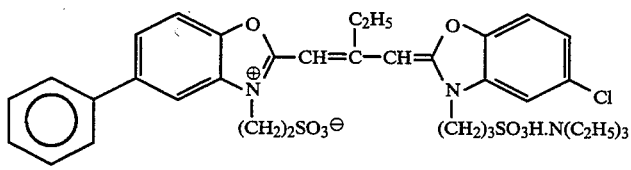

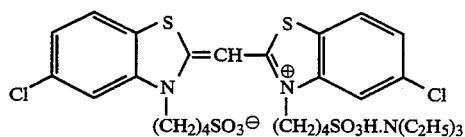

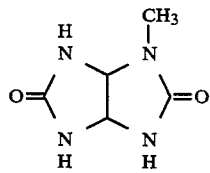

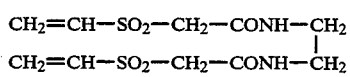

Sensitizing Dye VII

Sensitizing Dye VIII

S-1

H-1

Samples 402 to 404 were prepared in the same manner as sample 401, except that the yellow coupler- Ex-9 (YC-7) in the emulsion layers of the first blue-sensensitive layer, the second blue-sensitive layer, and the third blue-sensitive layer was changed to the coupler of the present invention, respectively, as shown in Table 5.

Further, Samples 405 to 407 were prepared in the same manner as Samples 402 to 404, respectively, except that the respective coating amount of silver halide emulsion in the first, the second, and the third blue-sensitive emulsion layer, each composition being not changed, was changed as shown in Table 5 in such a manner as to obtain the nearly similar gradation in each layer.

These samples were subjected to an exposure of white light through an wedge and then subjected to the same processing process as described in Example 3.

Yellow color densities of thus processed samples were measured and the results are shown in Table 5.

TABLE 5

| Sample No. | Coupler | Coating Amount | ΔFog*1 | $D_B$*2 | Remarks |
| --- | --- | --- | --- | --- | --- |
| 401 | YC-7 | 100% | ±0 | 1.80 | Comparative Example |
| 402 | Y-9 | 100% | ±0 | 1.95 | This Invention |
| 403 | Y-54 | 100% | +0.01 | 2.03 | This Invention |
| 404 | Y-76 | 100% | +0.02 | 2.08 | This Invention |
| 405 | Y-9 | 93% | ±0 | 1.80 | This Invention |
| 406 | Y-54 | 88% | ±0 | 1.79 | This Invention |
| 407 | Y-76 | 86% | +0.01 | 1.80 | This Invention |

Note:
*1Fogging density as compared with that of Sample 401 as standard
*2Yellow color density on the basis of the density fogging part which exposed to light so as to give a yellow color density of 1.80 compared with that of fogging part of Sample 401

As is apparent from results in Table 5, it can be understood that the coupler of the present invention gives high color density at the same coating amount and the coating amount of the present coupler which is required to obtain the similar density as Sample 401 can be small compared with the comparative coupler YC-7, as shown by Samples 405 to 407. This can not only bring an economical benefit but also make possible to thin the emulsion layer resulting that unpreferable light absorption in casein layer is reduced and the sharpness of image is improved.

A pattern for MTF measurement was printed on Samples 401 and 405 to 407 and MTF value at space frequency of 25 cycle/mm after development processing was measured using a red light. The results are shown in Table 6.

TABLE 6

| Sample No. | Coupler | Coating Amount | MTF Value of red light | Remarks |
| --- | --- | --- | --- | --- |
| 401 | Yc-7 | 100% | 0.42 | Comparative Example |
| 405 | Y-9 | 93% | 0.44 | This Invention |
| 406 | Y-54 | 88% | 0.45 | This Invention |
| 407 | Y-76 | 86% | 0.46 | This Invention |

As is apparent from the results in Table 6, it can be noticed that the coupler of the present invention gives higher MTF value than that of comparative coupler to improve sharpness.

Thus it is possible to say that the coupler of the present invention is an excellent coupler that can give higher color density to improve the sharpness of photographic material.

EXAMPLE 5

Preparation of Sample 501

Multilayer color photographic material sample 501 was prepared by multi-coating each layer having a composition as shown below on a prime-coated triacetate cellulose film base having a thickness of 127 μm. The figures provided indicate the coating amounts in g/m². The effects of added compounds are not restricted to the shown usage.

| First layer (Halation preventing layer) | |
| --- | --- |
| Black colloidal silver silver | 0.25 g |
| Gelatin | 1.9 g |
| UV-absorbent U-1 | 0.04 g |
| UV-absorbent U-2 | 0.1 g |
| UV-absorbent U-3 | 0.1 g |

| -continued | |
|---|---|
| UV-absorbent U-4 | 0.1 g |
| UV-absorbent U-6 | 0.1 g |
| High-boiling organic solvent Oil-1 | 0.1 g |
| Second layer (Intermediate layer) | |
| Gelatin | 0.40 g |
| Dye D-4 | 0.4 mg |
| Third layer (Intermediate layer) | |
| Fine particale silver iodobromide emulsion fogged the surface and the inner (average particle size: 0.06 μm, deviation coefficient: 18%, AgI content: 1 mol %) 0.05 g | silver 0.05 g |
| Gelatin | 0.4 g |
| Fourth layer (Low sensitivity red-sensitive emulsion layer) | |
| Emulsion A | silver 0.2 g |
| Emulsion B | silver 0.3 g |
| Gelatin | 0.8 g |
| Coupler C-1 | 0.15 g |
| Coupler C-2 | 0.05 g |
| Coupler C-9 | 0.05 g |
| Compound Cpd-D | 10 mg |
| High-boiling organic solvent Oil-2 | 0.1 g |
| Fifth layer (Medium sensitivity red-sensitive emulsion layer | |
| Emulsion B | silver 0.2 g |
| Emulsion C | silver 0.3 g |
| Gelatin | 0.8 g |
| Coupler C-1 | 0.2 g |
| Coupler C-2 | 0.05 g |
| Coupler C-3 | 0.2 g |
| High-boiling organic solvent Oil-2 | 0.1 g |
| Sixth layer (High sensitivity red-sensitive emulsion layer | |
| Emulsion D | silver 0.4 g |
| Gelatin | 1.1 g |
| Coupler C-1 | 0.7 g |
| Coupler C-2 | 0.3 g |
| Additive P-1 | 0.1 g |
| Seventh layer (Intermediate layer) | |
| Gelatin | 0.6 g |
| Additive M-1 | 0.3 g |
| Color-mix inhibiting agent Cpd-K | 2.6 mg |
| UV-absorbent U-1 | 0.1 g |
| UV-absorbent U-6 | 0.1 g |
| Dye D-1 | 0.02 g |
| Eighth layer (Intermediate layer) | |
| Silver iodobromide emulsion fogged the surface and the inner (average particle size: 0.06 μm, deviation coefficient: 16%, AgI content: 0.3 mol %) | silver 0.02 g |
| Gelatin | 1.0 g |
| Additive P-1 | 0.2 g |
| Color-mix inhibiting agent Cpd-J | 0.1 g |
| Color-mix inhibiting agent Cpd-A | 0.1 g |
| Ninth layer (Low sensitivity green-sensitive emulsion layer) | |
| Emulsion E | silver 0.3 g |
| Emulsion F | silver 0.1 g |
| Emulsion G | silver 0.1 g |
| Gelatin | 0.5 g |
| Coupler C-7 | 0.35 g |
| Compound Cpd-B | 0.03 g |
| Compound Cpd-E | 0.02 g |
| Compound Cpd-F | 0.02 g |
| Compound Cpd-G | 0.02 g |
| Compound Cpd-H | 0.02 g |
| Compound Cpd-D | 10 mg |
| High-boiling organic solvent Oil-1 | 0.1 g |
| High-boiling organic solvent Oil-2 | 0.1 g |
| Tenth layer (Medium sensitivity green-sensitive emulsion layer) | |
| Emulsion G | silver 0.3 g |
| Emulsion H | silver 0.1 g |
| Gelatin | 0.6 g |
| Coupler C-7 | 0.3 g |
| Compound Cpd-B | 0.03 g |
| Compound Cpd-E | 0.02 g |
| Compound Cpd-F | 0.02 g |
| Compound Cpd-G | 0.05 g |

| -continued | |
|---|---|
| Compound Cpd-H | 0.05 g |
| High-boiling orgaic solvent Oil-2 | 0.01 g |
| Eleventh layer (High sensitivity green-sensitive emulsion layer | |
| Emulsion I | silver 0.5 g |
| Gelatin | 1.0 g |
| Coupler C-4 | 0.4 g |
| Compound Cpd-B | 0.08 g |
| Compound Cpd-E | 0.02 g |
| Compound Cpd-F | 0.02 g |
| Compound Cpd-G | 0.02 g |
| Compound Cpd-H | 0.02 g |
| High-boiling organic solvent Oil-1 | 0.02 g |
| High-boiling organic solvent Oil-2 | 0.02 g |
| Twelfth layer (Intermediate layer) | |
| Gelatin | 0.6 g |
| Dye D-2 | 0.05 g |
| Dye D-1 | 0.1 g |
| Dye D-3 | 0.07 g |
| Thirteenth layer (Yellow filter layer) | |
| Yellow coloidal silver | silver 0.1 g |
| Gelatin | 1.1 g |
| Color-mix inhibiting agent Cpd-A | 0.01 g |
| High-boiling organic solvent Oil-1 | 0.01 g |
| Fourteenth layer (Intermediate layer) | |
| Gelatin | 0.6 g |
| Fifteenth layer (Low sensitivity blue-sensitive emulsion layer | |
| Emulsion J | silver 0.4 g |
| Emulsion K | silver 0.1 g |
| Emulsion L | silver 0.1 g |
| Gelatin | 0.8 g |
| Coupler C-5 | 0.4 g |
| Sixteenth layer (Medium sensitivity blue-sensitive emulsion layer) | |
| Emulsion L | silver 0.1 g |
| Emulsion M | silver 0.4 g |
| Gelatin | 0.9 g |
| Coupler C-5 | 0.20 g |
| Coupler C-6 | 0.25 g |
| Seventeenth layer (High sensitivity blue-sensitive emulsion layer) | |
| Emulsion N | silver 0.4 g |
| Gelatin | 1.2 g |
| Coupler C-6 | 0.7 g |
| Eighteenth layer (First protective layer) | |
| Gelatin | 0.7 g |
| UV-absorbent U-1 | 0.04 g |
| UV-absorbent U-2 | 0.01 g |
| UV-absorbent U-3 | 0.04 g |
| UV-absorbent U-4 | 0.03 g |
| UV-absorbent U-5 | 0.04 g |
| UV-absorbent U-6 | 0.05 g |
| High-boiling organic solvent Oil-1 | 0.02 g |
| Formalin scavenger Cpd-C | 0.2 g |
| Cpd-I | 0.4 g |
| Dye D-3 | 0.05 g |
| Ninteenth layer (Second protective layer) | |
| Colloidal silver | silver 0.1 mg |
| Fine particle silver iodobromide emulsion (average particle diameter: 0.06 μm, AgI content: 1 mol %) | silver 0.1 g |
| Gelatin | 0.4 g |
| Twentieth layer (Third protective layer) | |
| Gelatin | 0.4 g |
| Polymethylmethacrylate (average grain diameter: 1.5 μm) | 0.1 g |
| Copolymer of methylmethacrylate and acrylic acid (4:6) (average grain diameter: 1.5 μm) | 0.1 g |
| Silicone oil | 0.03 g |
| Surface-active agent W-1 | 3.0 mg |
| Surface-active agent W-2 | 0.03 g |

Additives F-1 to F-8 were added to all emulsion layers in addition to the above composition. Further, gelatin hardener H-1 and surface-active agents for emulsifying W-3 and W-4 were added to each layer in addition to the above composition.

Further, phenol, 1,2-benzisothiazoline-3-one, 2-phenoxyethanol, and fenetyl alcohol were added as antiseptics and antimildews.

Silver iodobromide emulsions used for Sample 501 were as follows:

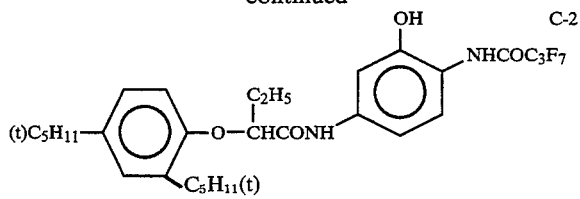

| Emulsion | Feature of grain | Average grain-diameter (μm) | Deviation coefficient (%) | AgI content (%) |
|---|---|---|---|---|
| A | Monodisperse tetradecahedral grain | 0.25 | 16 | 3.7 |
| B | Monodisperse cubic internal latent image-type grain | 0.30 | 10 | 3.3 |
| C | Monodisperse tetradecahedral grain | 0.30 | 18 | 5.0 |
| D | Polydisperse twin crystal grain | 0.60 | 25 | 2.0 |
| E | Monodisperse cubic grain | 0.17 | 17 | 4.0 |
| F | Monodisperse cubic grain | 0.20 | 16 | 4.0 |
| G | Monodisperse cubic internal latent image-type grain | 0.25 | 11 | 3.5 |
| H | Monodisperse cubic internal latent image-type grain | 0.30 | 9 | 3.5 |
| I | Polydisperse tabular grain, average aspect ratio: 3.8 | 0.80 | 28 | 1.5 |
| J | Monodisperse tetradecahedral grain | 0.30 | 18 | 4.0 |
| K | Monodisperse tetradecahedral grain | 0.37 | 17 | 4.0 |
| L | Monodisperse cubic internal latent image-type grain | 0.46 | 14 | 3.5 |
| M | Monodisperse cubic grain | 0.55 | 13 | 4.0 |
| N | Polydisperse tabular grain, average aspect ratio: 4.5 | 1.00 | 33 | 1.3 |

| | Spectral-sensitizing of Emulsions A to N | | |
|---|---|---|---|
| Emulsion | Spectral-sensitizing dye added | Amount of Added g per 1 mol of Silver Halide | Time when spectral-sensitizing dye added |
| A | S-1 | 0.025 | Immediately after chemical sensatization |
|   | S-2 | 0.25 | Immediately after chemical sensitization |
| B | S-1 | 0.01 | Immediately after grain formation ended |
|   | S-2 | 0.25 | Immediately after grain formation ended |
| C | S-1 | 0.02 | Immediately after chemical sensitization |
|   | S-2 | 0.25 | Immediately after chemical sensitization |
| D | S-1 | 0.01 | Immediately after chemical sensitization |
|   | S-2 | 0.10 | Immediately after chemical sensitization |
|   | S-7 | 0.01 | Immediately after chemical sensitization |
| E | S-3 | 0.5 | Immediately after chemical sensitization |
|   | S-4 | 0.1 | Immediately after chemical sensitization |
| F | S-3 | 0.3 | Immediately after chemical sensitization |
|   | S-4 | 0.1 | Immediately after chemical sensitization |
| G | S-3 | 0.25 | Immediately after grain formation ended |
|   | S-4 | 0.08 | Immediately after grain formation ended |
| H | S-3 | 0.2 | During grain formation |
|   | S-4 | 0.06 | During grain formation |
| I | S-3 | 0.3 | Immediately before chemical sensitization |
|   | S-4 | 0.07 | Immediately before chemical sensitization |
|   | S-8 | 0.1 | Immediately before chemical sensitization |
| J | S-5 | 0.2 | During grain formation |
|   | S-6 | 0.05 | During grain formation |
| K | S-5 | 0.2 | During grain formation |
|   | S-6 | 0.05 | During grain formation |
| L | S-5 | 0.22 | Immediately after grain formation ended |
|   | S-6 | 0.06 | Immediately after grain formation ended |
| M | S-5 | 0.15 | Immediately after chemical sensitization |
|   | S-6 | 0.04 | Immediately after chemical sensitization |
| N | S-5 | 0.22 | Immediately after grain formation ended |
|   | S-6 | 0.06 | Immediately after grain formation ended |

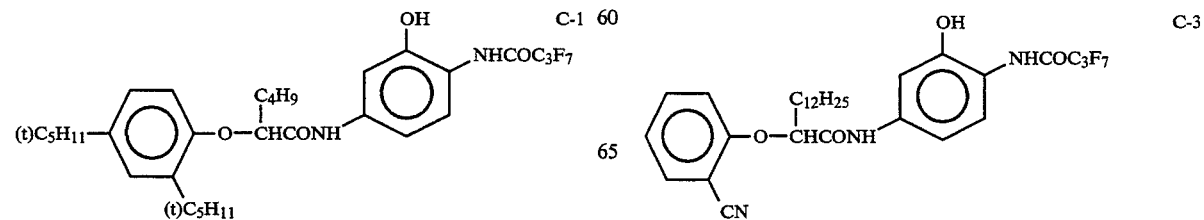

-continued
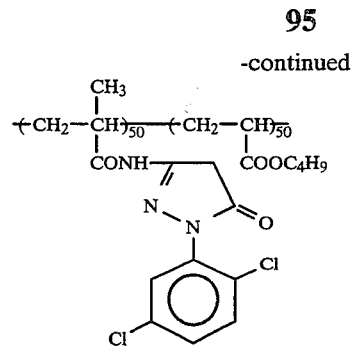
Figures represent Wt. %
Average Molecular Weight: ca, 25,000
C-5
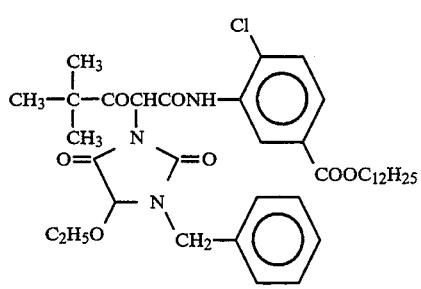
C-6
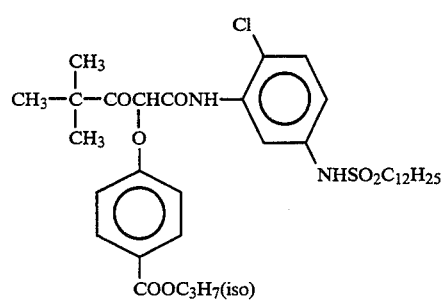
C-7
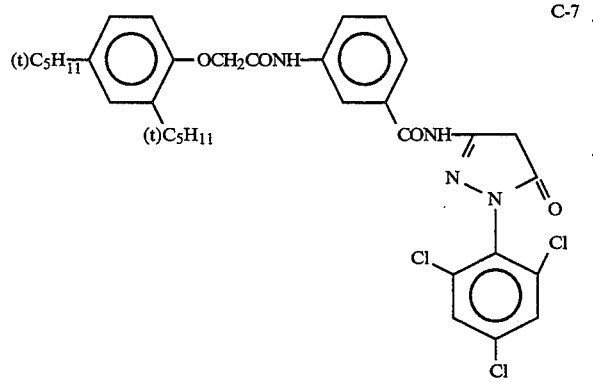
C-8
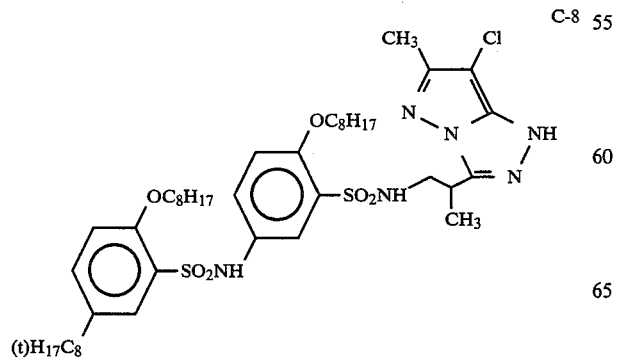
-continued
C-4
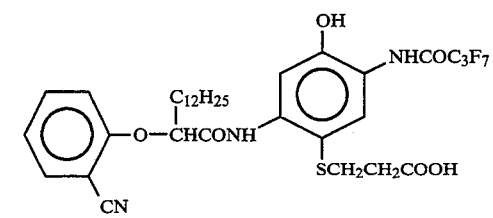
C-9
| | |
|---|---|
| Dibutyl phthalate | Oil-1 |
| Tricrezyl phosphate | Oil-2 |
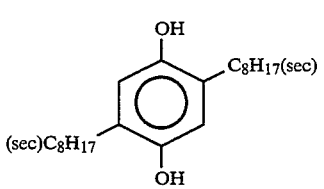 Oil-3
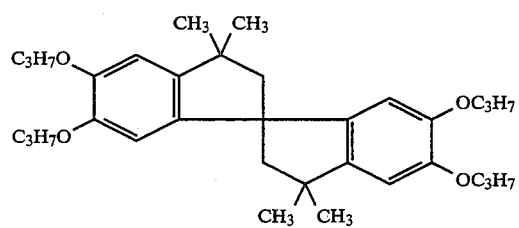 Cpd-A
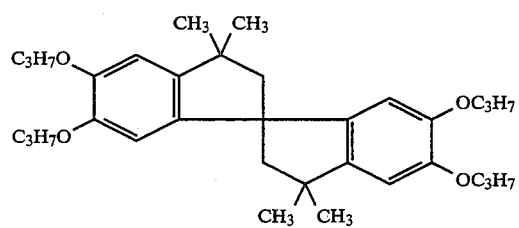 Cpd-B
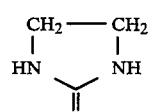 Cpd-C
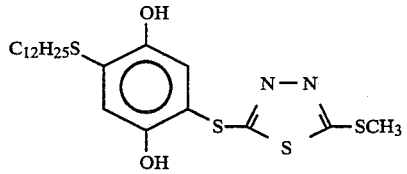 Cpd-D
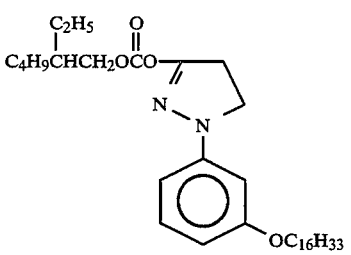 Cpd-E -continued
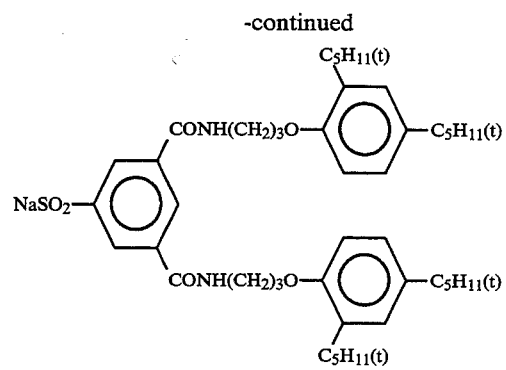 Cpd-F
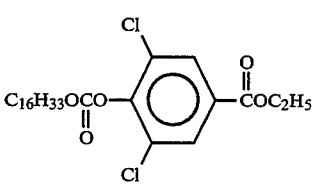 Cpd-G
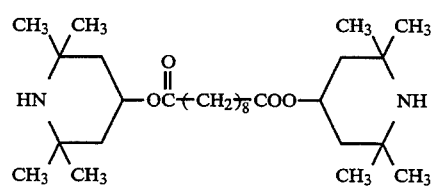 Cpd-H
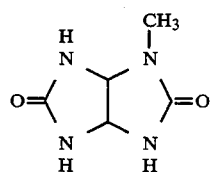 Cpd-I
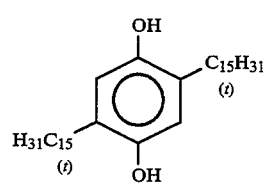 Cpd-J
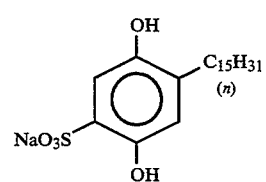 Cpd-K
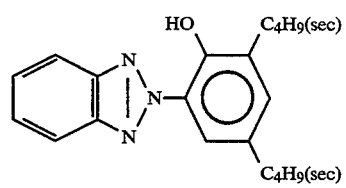 U-1
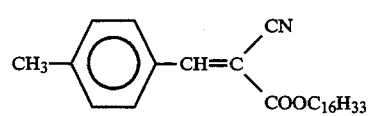 U-2
-continued
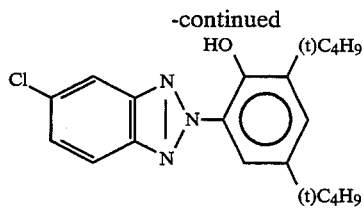 U-3
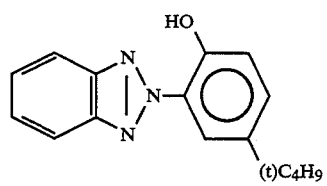 U-4
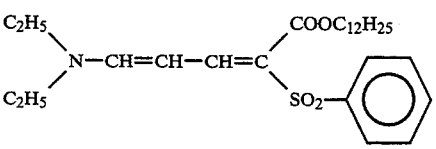 U-5
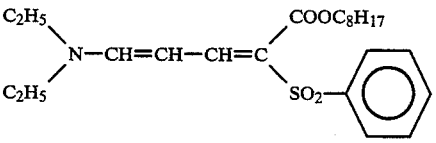 U-6
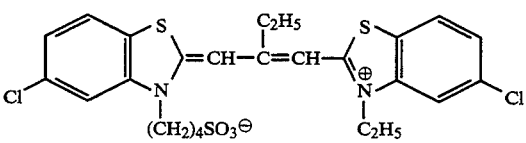 S-1
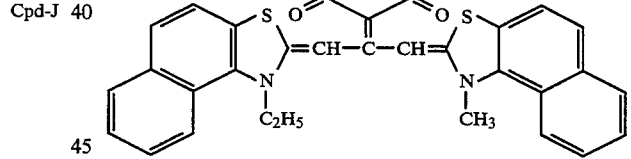 S-2
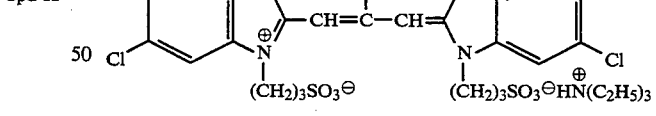 S-3
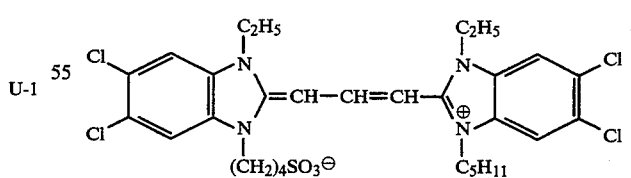 S-4
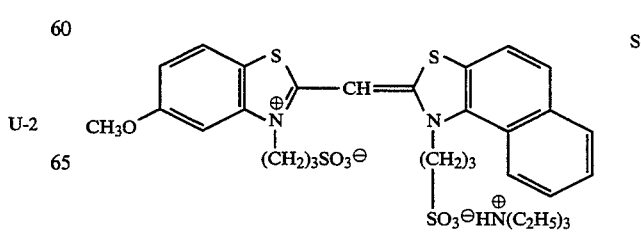 S-5

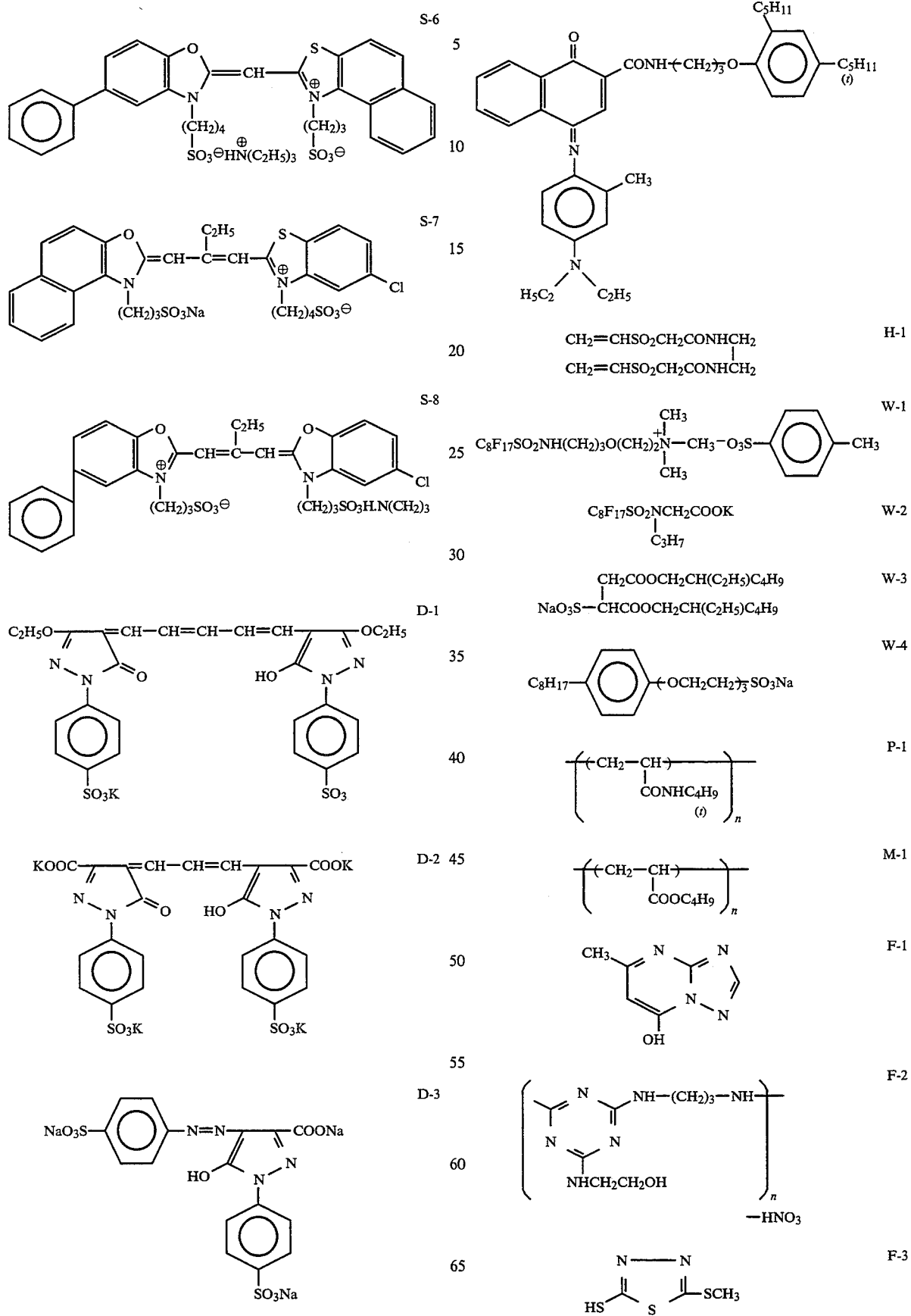

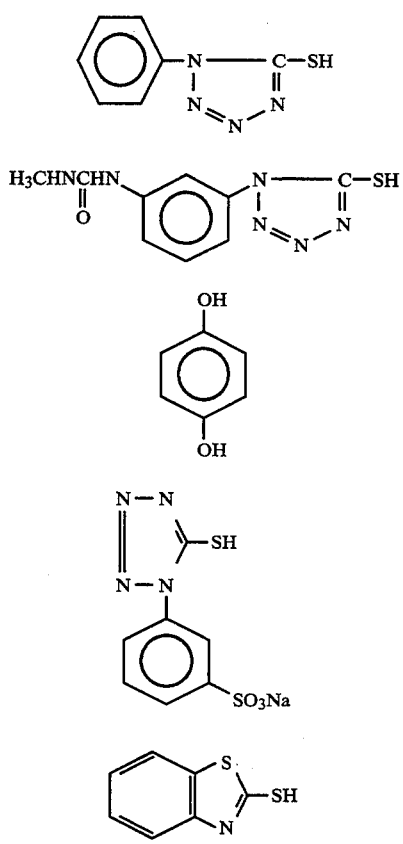

F-4

F-5

F-6

F-7

F-8

Other samples were prepared in the same manner as the above, except that yellow couplers in the blue-sensitive emulsion layers of low-sensitivity, medium-sensitivity, and high-sensitivity were changed to other comparative couplers and couplers of the present invention such that they would be present in an equimolar amount, respectively.

Thus-prepared samples were subjected to a gradation exposure to light and then to the processing shown below.

| Process | Processing process | |
|---|---|---|
| | Time (min.) | Temperature (°C.) |
| First developing | 6 | 38 |
| Water washing | 2 | 38 |
| Reversal developing | 2 | 38 |
| Color developing | 6 | 38 |
| Compensating | 2 | 38 |
| Bleaching | 6 | 38 |
| Fixing | 4 | 38 |
| Water washing | 4 | 38 |
| Stabilizing | 1 | Ordinary temp. |
| Drying | | |

The composition of each processing solution is as follows:

| First developing solution | |
|---|---|
| Water | 700 ml |
| Pentasodium nitrilo-N,N,N-trimethylene-phophonate | 2 g |
| Sodium sulfite | 20 g |
| Hydroquinonemonosulfonate | 30 g |
| Sodium carbonate monohydrate | 30 g |
| 1-Phenyl-4-methyl-4-hydroxymethyl- | 2 g |
| 3-pyrazolidone | |
| Potassium bromide | 2.5 g |
| Potassium thiocyanate | 1.2 g |
| Potassium iodide (0.1% solution) | 2 ml |
| Water to make | 1,000 ml |
| Reversal developing solution | |
| Water | 700 ml |
| Pentasodium nitrilo-N,N,N-trimethylene-phophonate | 2 g |
| Stannous chloride dehydrate | 1 g |
| p-Aminophenol | 0.1 g |
| Sodium hydroxide | 8 g |
| Glacial acetic acid | 15 ml |
| Water to make | 1,000 ml |
| Color developing solution | |
| Water | 700 ml |
| Pentasodium nitrilo-N,N,N-trimethylene-phophonate | 3 g |
| Sodium sulfite | 7 g |
| Sodium tertiary phosphate.12H$_2$O | 36 g |
| Potassium bromide | 1 g |
| Potassium iodide (0.1% solution) | 90 ml |
| Sodium hydroxide | 3 g |
| Citrazinic acid | 1.5 g |
| N-Ethyl-N-($\beta$-methanesulfonamidoethyl)-3-methyl-4-aminoaniline sulfate | 11 g |
| 3,6-dithiaoctane-1,8-diol | 1 g |
| Water to make | 1,000 ml |
| Compensating solution | |
| Water | 700 ml |
| Sodium sulfite | 12 g |
| Sodium ethylenediaminetetraacetate dihydrate | 8 g |
| Thioglycerin | 0.4 ml |
| Glacial acetic acid | 3 ml |
| Water to make | 1,000 ml |
| Bleaching Solution | |
| Water | 800 ml |
| Sodium ethylenediaminetetraacetate dehydrate | 2 g |
| Fe(III) ammonium ethylenediamine-tetraacetate dehydrate | 120 g |
| Potassium bromide | 100 g |
| Water to make | 1,000 ml |
| Fixing solution | |
| Water | 800 ml |
| Sodium thiosulfate | 80.0 g |
| Sodium sulfite | 5.0 g |
| Sodium bisulfite | 5.0 g |
| Water to make | 1,000 ml |
| Stabilizing solution | |
| Water | 800 ml |
| Formalin | 5.0 ml |
| Fuji Driwell (surface-active agent, prepared by Fuji Photo Film Co., Ltd.) | 5.0 ml |
| Water to make | 1,000 ml |

Results are shown in Table 5.

TABLE 5

| Sample | Coupler | Dmax | Remarks |
|---|---|---|---|
| 501 | YC-2 | 2.78 | Comparative Example |
| 502 | YC-8 | 2.92 | Comparative Example |
| 503 | YC-2, YC-8 | 2.88 | Comparative Example |
| 504 | Y-9 | 3.15 | This Invention |
| 505 | Y-8 | 3.32 | This Invention |
| 506 | Y-6 | 3.40 | This Invention |
| 507 | Y-46 | 3.18 | This Invention |

As is apparent from the results in Table 5, it can be understood that couplers of the present invention are excellent couplers giving high color density compared with comparative couplers.

EXAMPLE 6

A color photographic material was prepared by multi-coatings composed of the first to the twelfth layer as shown below on a both-sides polyethylene-laminated paper base. As a white pigment titanium white and as a bluish dye ultramarine blue were included in the first layer side polyethylene film laminated. Composition of photosensitive layers In the following compositions, each ingredient is indicated in g/m² of a coating amount, but the coating amount of the silver halide is indicated in terms of silver.

| | |
|---|---|
| First layer (Gelatin layer) | |
| Gelatin | 1.30 |
| Second layer (Antihalation layer) | |
| Black colloidal silver | 0.10 |
| Gelatin | 0.70 |
| Third layer (Low-sensitivity red-sensitive emulsion layer) | |
| Silver chloroiodobromide emulsion EM1 (AgCl: 1 mol %, AgI: 4 mol %; average grain size: 0.3 μm, distribution of grain size; 10%; cubic grains, core-shell type with core of iodide) spectral-sensitized by red-sensitizing dyes (ExS-1, -2, and -3) | 0.06 |
| Silver iodobromide emulsion EM2 (AgI: 5 mol %; average grain size: 0.45 μm, distribution of grain size: 20%; tabular grains (aspect ratio: 5)) spectral-sensitized by red-sensitizing dyes (ExS-1, -2, and -3) | 0.10 |
| Gelatin | 1.00 |
| Cyan coupler (ExC-1) | 0.14 |
| Cyan coupler (ExC-2) | 0.07 |
| Discoloration inhibitor (Cpd-2, -3, -4, and -9 each in equal amount) | 0.12 |
| Dispersive medium for coupler (Cpd-5) | 0.03 |
| Solvent for coupler (Solv-1, -2, and -3) | 0.06 |
| Fourth layer (High-sensitivity red-sensitive emulsion) layer | |
| Silver iodobromide emulsion EM3 (AgI: 6 mol %; average grain size: 0.75 μm, distribution of grain size: 25%; tabular grains (aspect ratio: 8, core: iodide)) spectral-sensitized by red-sensitizing dyes (ExS-1, -2, and -3) | 0.15 |
| Gelatin | 1.00 |
| Cyan coupler (ExC-1) | 0.20 |
| Cyan coupler (ExC-2) | 0.10 |
| Discoloration inhibitor (Cpd-2, -3, -4, and -9 each in equal amount) | 0.15 |
| Dispersive medium for coupler (Cpd-5) | 0.03 |
| Solvent for coupler (Solv-1, -2, and -3) | 0.10 |
| Fifth layer (Intermediate layer) | |
| Magenta colloidal silver | 0.02 |
| Gelatin | 1.00 |
| Color-mix inhibitor (Cpd-6 and -7) | 0.08 |
| Solvent for color-mix inhibitor (Solv-4 and -5) | 0.16 |
| Polymer latex (Cpd-8) | 0.10 |
| Sixth layer (Low-sensitivity green-sensitive emulsion layer) | |
| Silver chloroiodobromide emulsion EM4 (AgCl: 1 mol %, AgI: 2.5 mol %; average grain size: 0.28 μm, distribution of grain size: 12%; cubic grains, core-shell type with core of iodide) spectral-sensitized by green-sensitizing dye (ExS-3) | 0.04 |
| Silver iodobromide emusion EM5 (AgI: 2.8 mol %; average grain size: 0.45 μm, distribution of grain size: 12%; tabular grains (aspect atio: 5)) spectral-sensitized by green-sensitizing dyes (ExS-3) | 0.06 |
| Gelatin | 0.80 |
| Magenta coupler (ExM-1) | 0.10 |
| Discoloration inhibitor (Cpd-9) | 0.10 |
| Stain inhibitor (Cpd-10) | 0.01 |
| Stain inhibitor (Cpd-11) | 0.001 |
| Stain inhibitor (Cpd-12) | 0.01 |
| Dispersive medium for coupler (Cpd-5) | 0.05 |
| Solvent for coupler (Solv-4 and -6) | 0.15 |
| Seventh layer (High sensitivity green-sensitive emulsion layer) | |
| Silver iodobromide emulsion EM6 (AgI: 3.5 mol %; average grain size: 0.9 μm, distribution of grain size: 23%; tabular grains (aspect ratio: 9, uniform iodide-type)) spectral-sensitized by green-sensitive dye (ExS-3) | 0.10 |
| Gelatin | 0.80 |
| Magenta coupler (ExM-1) | 0.10 |
| Discoloration inhibitor (Cpd-9) | 0.10 |
| Stain inhibitor (Cpd-10) | 0.01 |
| Stain inhibitor (Cpd-11) | 0.001 |
| Stain inhibitor (Cpd-12) | 0.01 |
| Dispersive medium for coupler (Cpd-5) | 0.05 |
| Solvent for coupler (Solv-4 and -6) | 0.15 |
| Eighth layer (Yellow filter layer) | |
| Yellow colloidal silver | 0.20 |
| Gelatin | 1.00 |
| Color-mix inhibitor (Cpd-7) | 0.06 |
| Solvent for color-mix inhibitor (Solv-4 and -5) | 0.15 |
| Polymer latex (Cpd-8) | 0.10 |
| Ninth layer (Low-sensitivity blue-sensitive emulsion layer) | |
| Silver chloroiodobromide emulsion EM7 (AgCl: 2 mol %, AgI: 2.5 mol %; average grain size: 0.35 μm, distribution of grain size: 8%; cubic grains, core-shell type with core of iodide) spectral-sensitized by green-sensitizing dye (ExS-5 and -6) | 0.07 |
| Silver iodobromide emulsion EM5 (AgI: 2.5 mol %; average grain size: 0.45 μm, distribution of grain size: 16%; tabular grains (aspect ratio: 6)) spectral-sensitized by green-sensitizing dyes (ExS-5 and -6) | 0.10 |
| Gelatin | 0.50 |
| Yellow coupler (ExY-1) | 0.20 |
| Stain inhibitor (Cpd-11) | 0.001 |
| Discoloration inhibitor (Cpd-6) | 0.10 |
| Dispersive medium for coupler (Cpd-5) | 0.05 |
| Solvent for coupler (Solv-2) | 0.05 |
| Tenth layer (High-sensitivity blue-sensitive emulsion layer) | |
| Silver iodobromide emulsion EM9 (AgI: 2.5 mol %; average grain size: 1.2 μm, distribution of grain size: 21%; tabular grains (aspect ratio: 14)) spectral-sensitized by green-sensitive dyes (ExS-5 and -6) | 0.25 |
| Gelatin | 1.00 |
| Yellow coupler (ExY-1) | 0.40 |
| Stain inhibitor (Cpd-11) | 0.002 |
| Discoloration inhibitor (Cpd-6) | 0.10 |
| Dispersive medium for coupler (Cpd-5) | 0.15 |
| Solvent for coupler (Solv-2) | 0.10 |
| Eleventh layer (UV-absorbing layer) | |
| Gelatin | 1.50 |
| UV absorbent (Cpd-1, -3, and -13) | 1.00 |
| Color-mix inhibitor (Cpd-6 and -14) | 0.06 |
| Dispersive medium (Cpd-5) | 0.05 |
| Solvent for UV-absorbent (Solv-1 and -2) | 0.15 |
| Irradiation preventing dye (Cpd-15 and -16) | 0.02 |
| Irradiation preventing dye (Cpd-17 and -18) | 0.02 |
| Twelfth layer (Protective layer) | |
| Fine grain size silver chlorobromide emulsion (silver chloride: 97 mol %, average grain size: 0.2 μm) | 0.07 |
| Modified polyvinyl alcohol | 0.02 |
| Gelatin | 1.50 |
| Gelatin hardener (H-1) | 0.17 |

Further, Alkanol XC (trade name, made by Dupont) and sodium alkylbenzenesulfonate were used as auxiliary agents for the emulsification and dispersion, and succinate ester and Magefac F-120 (trade name, made by Dai Nippon Ink & Chemicals Inc.) were added as coating aids to each layer. In the layers containing silver halide emulsion or coloidal silver, compounds (Cpd-19, -20, and -21) were used as stabilizers. Compounds used in the Example are shown below.
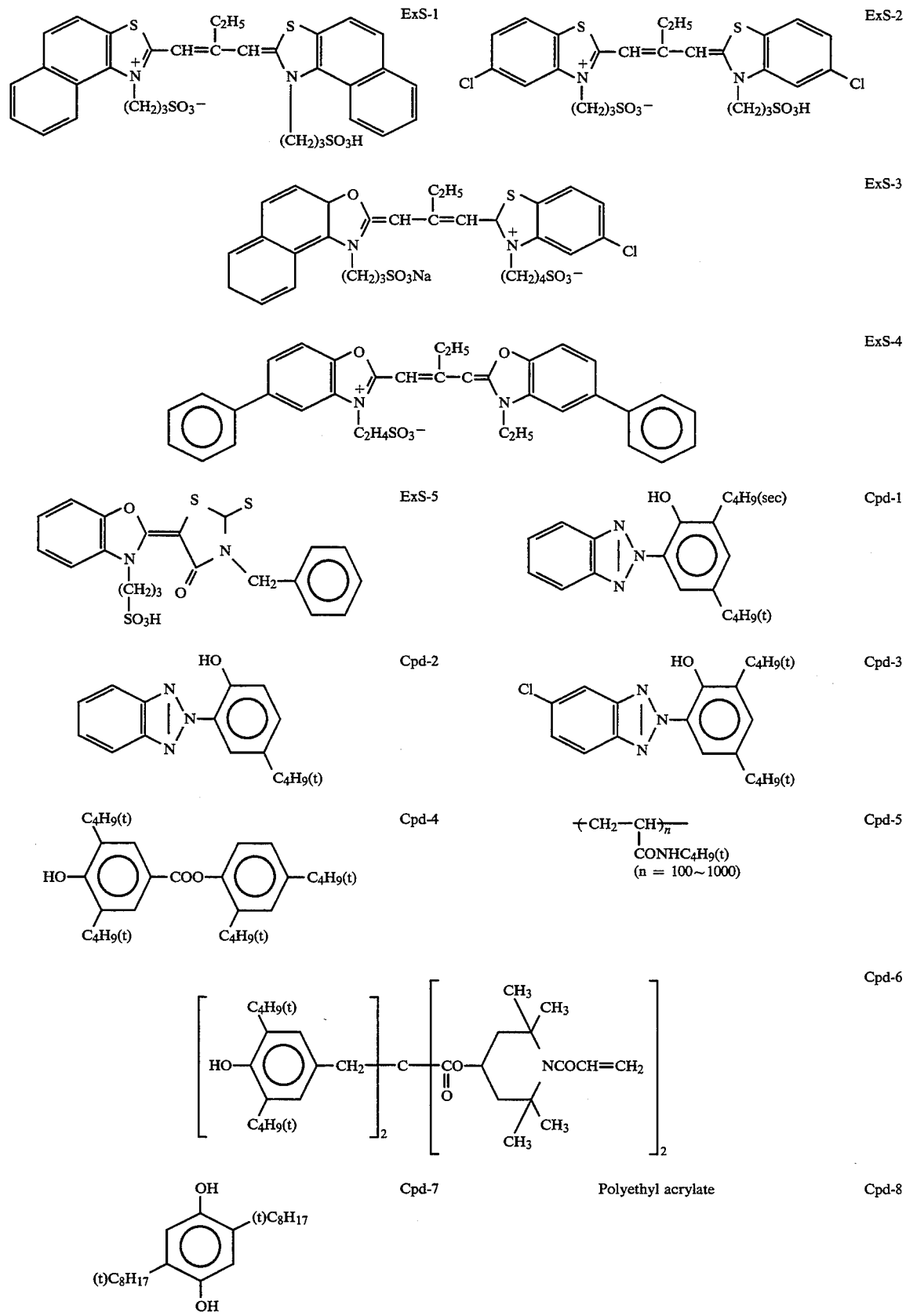

-continued
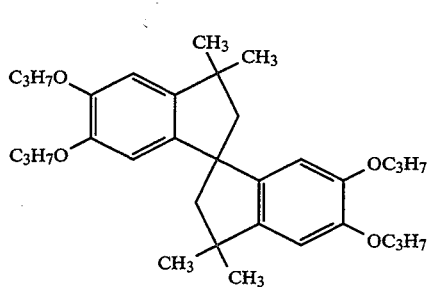 Cpd-9
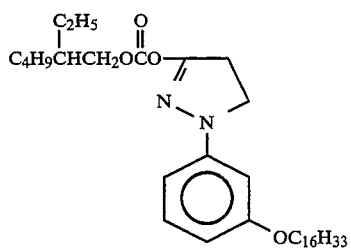 Cpd-10
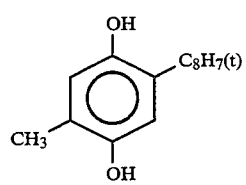 Cpd-11
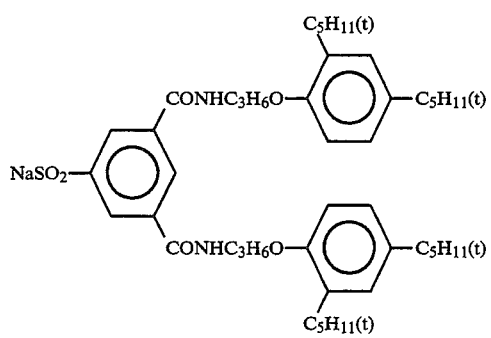 Cpd-12
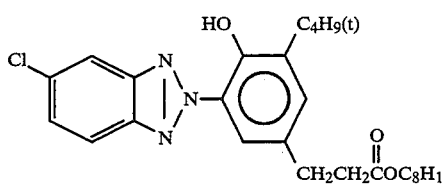 Cpd-13
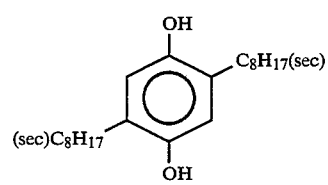 Cpd-14
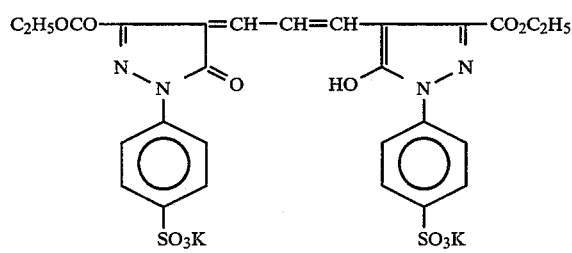 Cpd-15
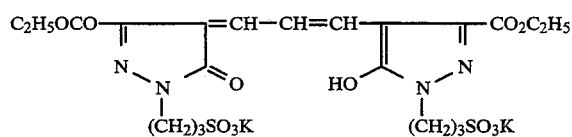 Cpd-16
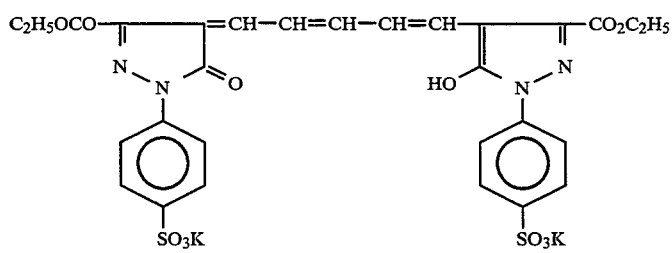 Cpd-17

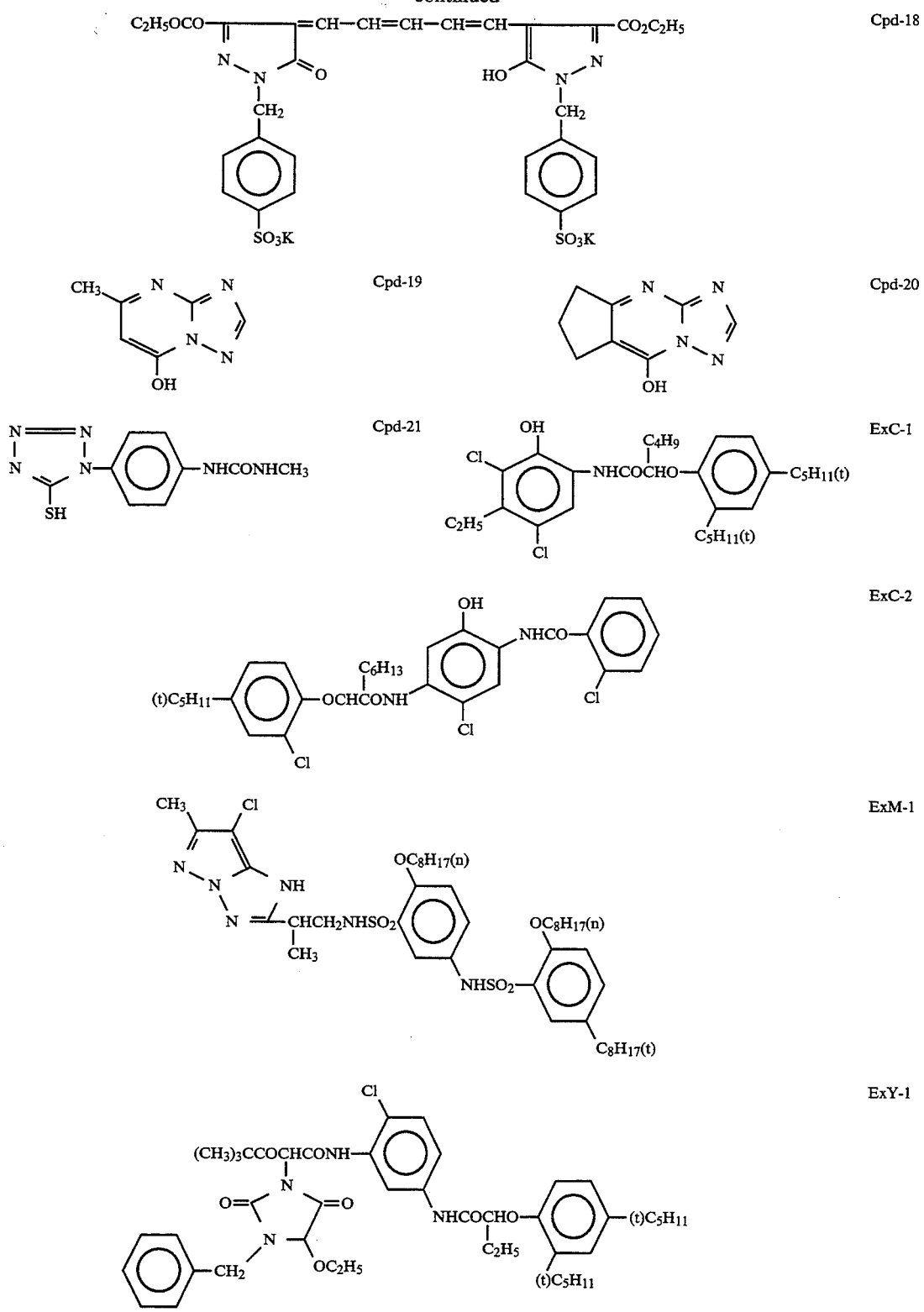

Emulsion A

Preparation of a Monodisperse Emulsion with (100) Crystal Habit

An aqueous silver nitrate solution and an aqueous solution containing KBr and KI were added by the double-jet method to an aqueous gelatin solution kept at 70° C., with the pBr being kept at 4.5, to prepare a monodisperse emulsion (the length of the edge: 0.68 μm) having (100) crystal habit. This core emulsion was divided into three, and shells were formed under different conditions shown below, so that the final grain size was 0.7 μm and the content of AgI was 3 mol %.

Sodium thiosulfate and potassium chloroaurate were added to the cores to carry out chemical sensitization. Thereafter, the shells were deposited under the same conditions as those for the formation of the cores.

Couplers for comparison and couplers of the present invention were prepared by replacing Yellow Coupler ExY-1 in the low-sensitive blue-sensitive layer and high-sensitive blue-sensitive layer so that it would be equimolar.

These samples were subjected to the processing according to the process shown below and to evaluation.

| Processing process | | |
|---|---|---|
| First developing (Black and white developing) | 38° C. | 75 sec |
| Water washing | 38° C. | 90 sec |
| Reversal exposure | over 100 Lux | over 60 sec |
| Color developing | 38° C. | 135 sec |
| Water washing | 38° C. | 45 sec |
| Bleach-fixing | 38° C. | 120 sec |
| Water washing | 38° C. | 135 sec |
| Drying | | |

| Composition of processing solution | |
|---|---|
| First developing solution | |
| Pentasodium nitrilo-N,N,N-trimethylene-phosphonate | 0.6 g |
| Pentasodium diethylenetriaminepentaacetate | 4.0 g |
| Potassium sulfite | 30.0 g |
| Potassium thiocyanate | 1.2 g |
| Potassium carbonate | 35.0 g |
| Potassium hydroquinonmonosulfonate | 25.0 g |
| Diethylene glycol | 15.0 ml |
| 1-Phenyl-4-hydroxy-methyl-4-methyl-3-pyrazolidon | 2.0 g |
| Potassium bromide | 0.5 g |
| Potassium iodide | 5.0 mg |
| Water to make | 1 l |
| | (pH 9.70) |
| Color developer | |
| Benzyl alcohol | 15.0 ml |
| Diethylene glycol | 12.0 ml |
| 3,6-Dithia-1,8-octanediol | 0.2 g |
| Pentasodium nitrylo-N,N,N-trimethylene phosphonate | 0.5 g |
| Pentasodium diethylenetriaminepentaacetate | 2.0 g |
| Sodium sulfite | 2.0 g |
| Potassium carbonate | 25.0 g |
| Hydroxylamine sulfonate | 3.0 g |
| N-Ethyl-N-(β-methanesulfonamidoethyl)-3-methyl-4-aminoaniline sulfonate | 5.0 g |
| Potassium bromide | 0.5 g |
| Potassium iodide | 1.0 mg |
| Water to make | 1 l |
| | (pH 10.40) |
| Bleach-fixing solution | |
| 2-Mercapto-1,3,4-triazole | 1.0 g |
| Disodium ethylenediaminetetraacetate dihydrate | 5.0 g |
| Iron(III) ammonium ethylenediamine-tetraacetate monohydrate | 80.0 g |
| Sodium sulfite | 15.0 g |
| Ammonium thiosulfate (700 g/l, solution) | 150.0 ml |
| Glacial acetic acid | 5.0 ml |
| Water to make | 1 l |
| | (pH 6.50) |

Water washing solution

Tap water was treated by passage through a hybrid-type column filled with an H-type strong acidic cation-exchange resin (Diaion SK-1B, tradename, made by Mitsubishi Chemical Industries, Ltd.) and an OH-type strong alkaline anion-exchange resin Diaion SA-10A, tradename, made by the same as the above) to obtain water having a quality as shown below. To the thus-treated water, 20 mg/l, of sodium dichloroisocyanurate was added as a bactericide.

In this case, the same results as in Example 1 were obtained.

EXAMPLE 7

A photographic material was prepared by multi-coatings composed of the following for the first to fourteenth layers on one side, and for the fifteenth and sixteenth layers on the back side of a double-sided polyethylene-laminated paper base (of thickness 100 μm). Titanium dioxide, as a white pigment, and a small amount of ultramarine blue, as a bluish dye, were included in the polyethylene film of the first-layer side (the chromaticies of the base surface in L*, a*, and b* were 88.0, −0.20, and −0.75, respectively).

Composition of Photosensitive Layers

In the following compositions each ingredient is indicated in g/m$^2$ of coating amount, but the coating amount of silver halide is indicated in terms of silver. Emulsions for each layer were prepared in accordance with the preparation procedure of EM1, providing that the emulsion of the 14th layer used a Lipman emulsion that was not chemically surface-ripened.

| First layer (Antihalation layer) | |
|---|---|
| Black colloidal silver | 0.10 |
| Gelatin | 0.70 |
| Second layer (Intermediate layer) | |
| Gelatin | 0.70 |
| Third layer (Low sensitivity red-sensitive emulsion layer) | |
| Silver bromide emulsion spectral-sensitized by red-sensitizing dyes (ExS-1, -2, and -3) (average grain size: 0.25 μm, grain size distribution (deviation coefficient): 8%, octahedral) | 0.04 |
| Silver chlorobromide emulsion spectral-sensitized by red-sensitizing dyes (ExS-1, -2, and -3) (silver chloride 5 mol %, average grain size: 0.40 μm, grain size distribution: 10%, octahedral) | 0.08 |
| Gelatin | 1.00 |
| Cyan coupler (a blend of ExC-1, -2, and -3 in a ratio of 1:1:0.2) | 0.30 |
| Discoloration inhibitor (a blend of Cpd-1, -2, -3, and -4, each in equal amount) | 0.18 |
| Stain inhibitor (Cpd-5) | 0.003 |
| Coupler dispersion medium (Cpd-6) | 0.03 |
| Coupler solvent (a blend of Solv-1, -2, and -3, each in equal amount) | 0.12 |
| Fourth layer (High sensitivity red-sensitive emulsion layer) | |
| Silver bromide emulsion spectral-sensitized by red-sensitizing dyes (ExS-1, -2, and -3) (average grain size: 0.60 μm, grain size | 0.14 |

| | |
|---|---|
| distribution: 15%, octahedral) | |
| Gelatin | 1.00 |
| Cyan coupler (a blend of ExC-1, -2, and -3 in a ratio of 1:1:0.2) | 0.30 |
| Discoloration inhibitor (a blend of Cpd-1, -2, -3 and -4, each in equal amount) | 0.18 |
| Coupler dispersion medium (Cpd-6) | 0.03 |
| Coupler solvent (a blend of Sovl-1, -2, and -3,-each in equal amount) | 0.12 |
| Fifth layer (Intermediate layer) | |
| Gelatin | 1.00 |
| Color-mix inhibitor (Cpd-7) | 0.08 |
| Color-mix inhibitor solvent (a blend of Solv-4 and -5, each in equal amount) | 0.16 |
| Polymer latex (Cpd-8) | 0.10 |
| Sixth layer (Low sensitivity green-sensitive emulsion layer) | |
| Silver bromide emulsion spectral-sensitized by green-sensitizing dye (ExS-4) (average grain size: 0.25 μm, grain size distribution: 8%, octahedral) | 0.04 |
| Silver chlorobromide emulsion spectral-sensitized by green-sensitizing dye (ExS-4) (silver chloride: 5 mol %, average grain size: 0.40 μm, grain size distribution: 10%, octahedral) | 0.06 |
| Gelatin | 0.80 |
| Magenta coupler (ExM-1) | 0.11 |
| Discoloration inhibitor (a blend of Cpd-9 and -26, each in equal amount) | 0.15 |
| Stain inhibitor (a blend of Cpd-10, -11, -12, and -13 in a ratio of 10:7:7:1) | 0.025 |
| Coupler dispersion medium (Cpd-6) | 0.05 |
| Coupler solvent (a blend of Solv-4 and -6, each in equal amount | 0.15 |
| Seventh layer (High sensitivity green-sensitive emulsion layer) | |
| Silver bromide emulsion spectral-sensitized by green-sensitizing dye (ExS-4) (average grain size: 0.65 μm, grain size distribution: 16%, octahedral) | 0.10 |
| Gelatin | 0.80 |
| Magenta coupler (a blend of ExM-1, -2, and -3, each in equal amount) | 0.11 |
| Discoloration inhibitor (a blend of Cpd-9 and -26, each in equal amount) | 0.15 |
| Stain inhibitor (a blend of Cpd-10, -11, -12, and -13 in a ratio of 10:7:7:1) | 0.025 |
| Coupler dispersion medium (Cpd-6) | 0.05 |
| Coupler solvent (a blend of Solv-4 and -6, each in equal amount) | 0.15 |
| Eighth layer (Intermediate layer) | |
| Same as the fifth layer | |
| Ninth later (Yellow filter layer) | |
| Yellow colloidal silver | 0.12 |
| Gelatin | 0.70 |
| Color-mix inhibitor (Cpd-7) | 0.03 |
| Color-mix-inhibitor solvent (a blend of Solv-4 and -5, each in equal amount) | 0.10 |
| Polymer latex (Cpd-8) | 0.07 |
| Tenth layer (Intermediate layer) | |
| Same as the fifth layer | |
| Eleventh layer (Low sensitivity blue-sensitive emulsion layer | |
| Silver bromide emulsion spectral-sensitized by blue-sensitizing dyes (ExS-5 and -6) (average grain size: 0.40 μm, grain size distribution: 8%, octahedral) | 0.07 |
| Silver chlorobromide emulsion spectral-sensitized by blue-sensitizing dyes (ExS-5 and -6) (silver chloride: 8 mol %, average grain size 0.60 μm, grain size distribution: 11% octahedral) | 0.14 |
| Gelatin | 0.80 |
| Yellow coupler (a blend of ExY-1 and -2, each in equal amount) | 0.35 |
| Discoloration inhibitor (Cpd-14) | 0.10 |
| Stain inhibitor (a blend of Cpd-5 and -15 in a ratio of 1:5) | 0.007 |
| Coupler dispersion medium (Cpd-6) | 0.05 |
| Coupler solvent (Solv-2) | 0.10 |
| Twelfth layer (High sensitivity blue-sensitive emulsion layer) | |
| Silver bromide emulsion spectral-sensitized by blue-sensitizing dyes (ExS-5 and -6) (average grain size: 0.85 μm, grain size distribution: 18%, octahedral) | 0.15 |
| Gelatin | 0.60 |
| Yellow coupler (a blend of ExY-1 and -2, each in equal amount) | 0.30 |
| Discoloration inhibitor (Cpd-14) | 0.10 |
| Stain inhibitor (a blend of Cpd-5 and -15 in a ratio of 1:5) | 0.007 |
| Coupler dispersion medium (Cpd-6) | 0.05 |
| Coupler solvent (Solv-2) | 0.10 |
| Thirteenth layer (Ultraviolet absorbing layer) | |
| Gelatin | 1.00 |
| Ultraviolet absorber (a blend of Cpd-2, -4, and -16, each in equal amount) | 0.50 |
| Color-mix inhibitor (a blend of Cpd-7 and -17, each in equal amount) | 0.03 |
| Dispersion medium (Cpd-6) | 0.02 |
| Ultraviolet absorber solvent (a blend of Solv-2 and -7, each in equal amount) | 0.08 |
| Irradiation-inhibiting dye (a blend of Cpd-18, -19, -20, -21, and -27 in a ratio of 10:10:13:15:20) | 0.05 |
| Fourteenth layer (Protective layer) | |
| Fine grain silver chlorobromide emulsion (silver chloride: 97 mol %, average grain size: 0.1 μm) | 0.03 |
| Copolymer of acryl-modified poly(vinyl alcohol) (Molecular weight: 50,000) | 0.01 |
| Poly(methyl methacrylate) particle (average particle size: 2.4 μm) and silicon dioxide (average particle size: 5 μm) (a blend, each in equal amount) | 0.05 |
| Gelatin | 1.80 |
| Gelatin hardener (a blend of H-1 and H-2, each in equal amount) | 0.18 |
| Fifteenth layer (Back-side layer) | |
| Gelatin | 2.50 |
| Ultraviolet absorber (a blend of Cpd-2, -4, and -16, each in equal amount) | 0.50 |
| Dye (a blend of Cpd-18, -19, -20, 21, and -27, each in equal amount) | 0.06 |
| Sixteenth layer (Back-side protective layer) | |
| Poly(methyl methacrylate) particle (average particle size: 2.4 μm) and silicon dioxide (average particle size: 5 μm) (a blend each in equal amount) | 0.05 |
| Gelatin | 2.00 |
| Gelatin hardener (a blend of H-1 and H-2, each in equal amount) | 0.14 |

Preparation of Emulsion EM-1

Aqueous solutions containing potassium bromide and silver nitrate were simultaneously added to an aqueous solution of gelatin with vigorous agitation at 75° C. over 15 minutes, to obtain a silver bromide emulsion of octahedral grains having an average grain size of 0.35 μm. A chemical-sensitizing treatment of the thus obtained emulsion was carried out by adding, in order, 0.3 g/mol-Ag of 3,4-dimethyl-1,3-thiazoline-2-thione, 6 mg/mol-Ag of sodium thiosulfate, and 7 mg/mol-Ag of chloroauric acid (tetrahydrate), and then heating the mixture at 70° C. for 80 minutes. The thus-obtained silver bromide grains were brought up as a core under the same precipitating conditions as the first precipitating process, to obtain a monodisperse core-shell silver bromide emulsion of octahedral-shaped grains having an average grain size of 0.7 μm. The deviation coefficient of the grain size distribution of this emulsion was about 10%. A further chemical sensitization of this emulsion was carried out by adding 1.5 mg/mol-Ag of sodium thiosulfate and 1.5 mg/mol-Ag of chloroauric acid (tetrahydrate), and then heating it at 60° C. for 60 minutes, to obtain an internal latent-image type silver halide emulsion.

In each photosensitive layer, the compounds, ExZK-1 and ExZK-2, in amounts of $13^{-3}$ and $10^{-2}$ weight % to the coating amount of silver halide, respectively, were included as nucleating agents, and $10^{-2}$ weight % of compound Cpd-22 was included as a nucleation accelerator. Further, Alkanol XC (trade name, made by Dupont) and sodium alkylbenzenesulfonate were used as auxiliary agents for the emulsification and dispersion, and succinate ester and Magefac F-120 (trade name, made by Dai Nippon Ink & Chemicals Inc.) were added as coating aids to each layer. In the layers containing silver halide emulsion or colloidal silver, compounds Cpd-23, −24, and −25 were used as stabilizers. Compounds used in the Example are shown below.

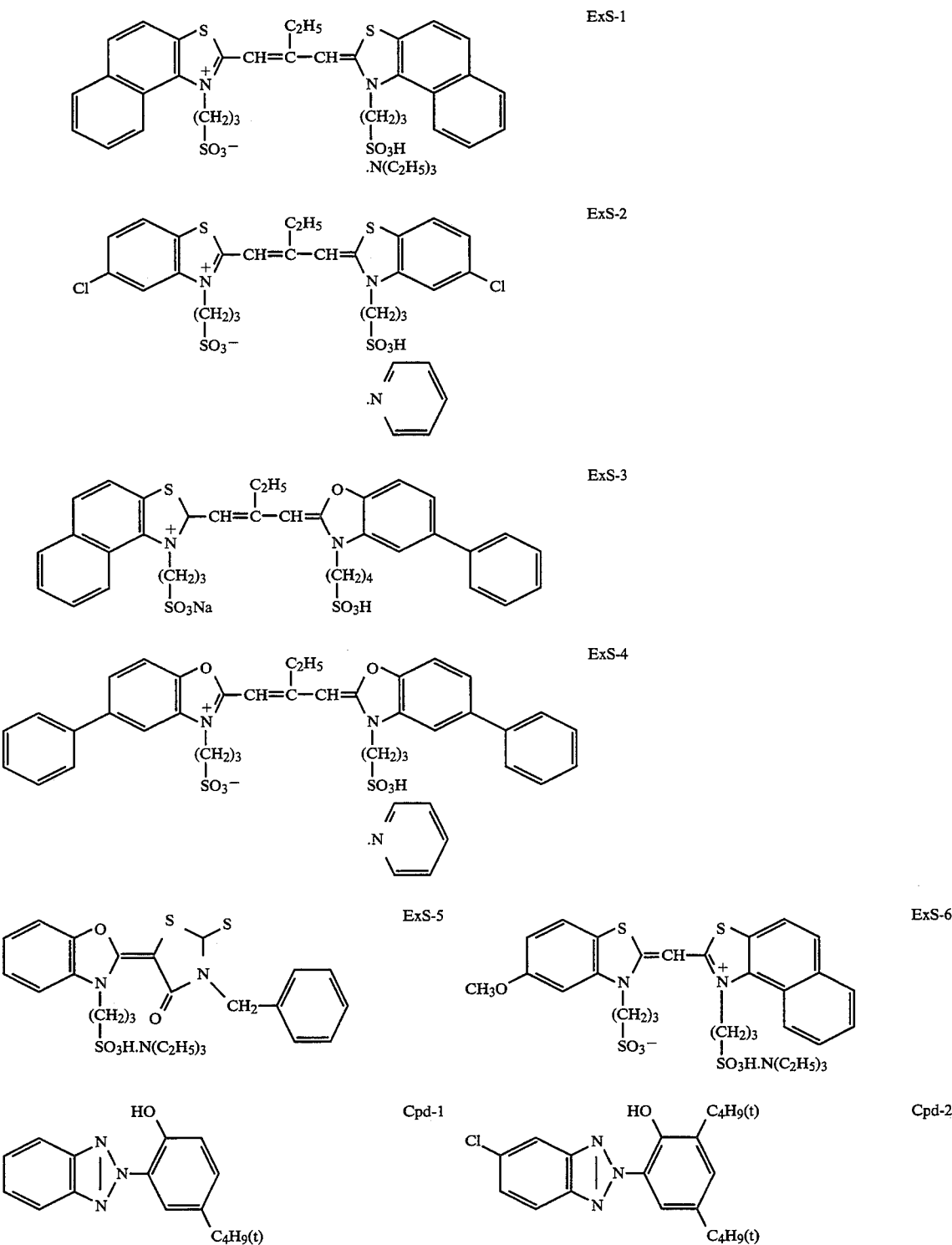

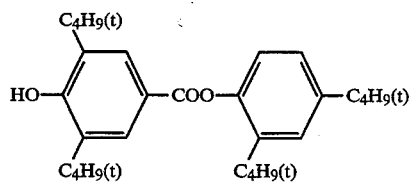 Cpd-3
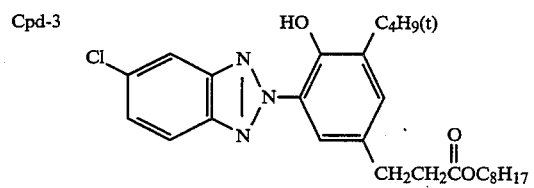 Cpd-4
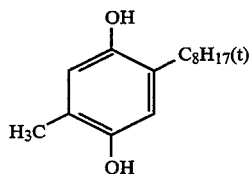 Cpd-5
 n = 100~1000  Cpd-6
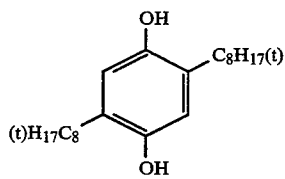 Cpd-7
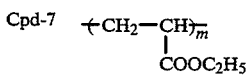 Cpd-8
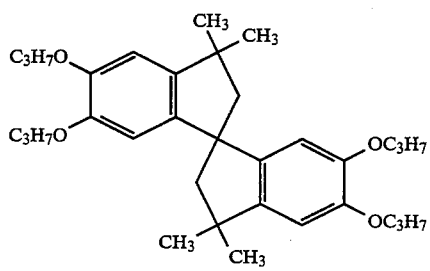 Cpd-9
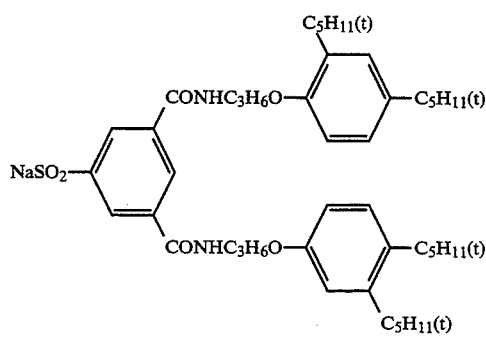 Cpd-10
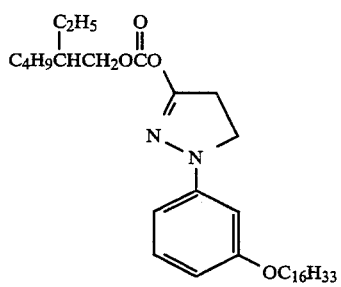 Cpd-11
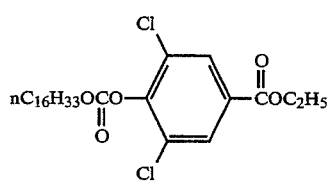 Cpd-12
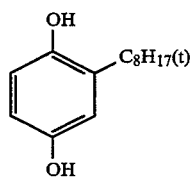 Cpd-13
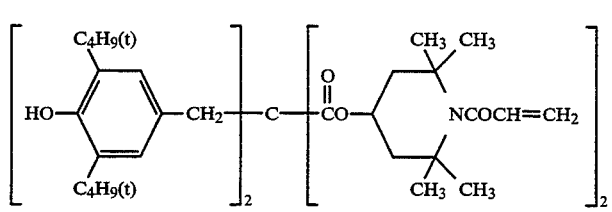 Cpd-14
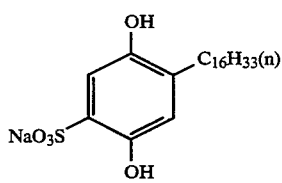 Cpd-15
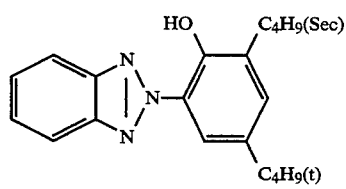 Cpd-16

-continued
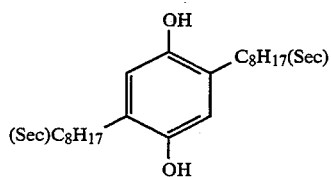 Cpd-17
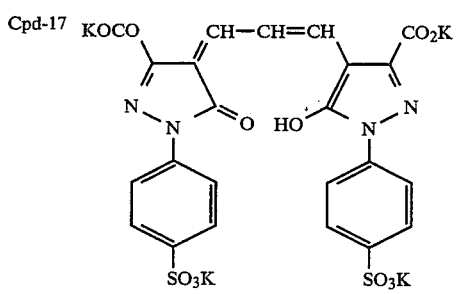 Cpd-18
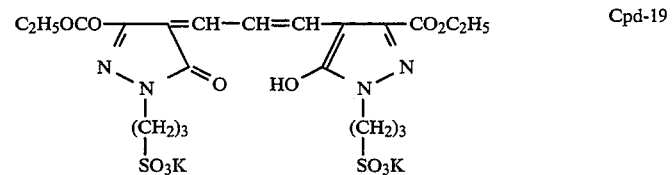 Cpd-19
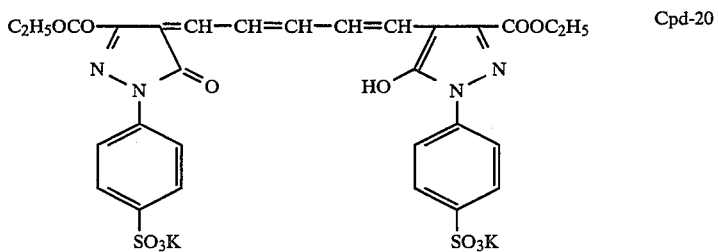 Cpd-20
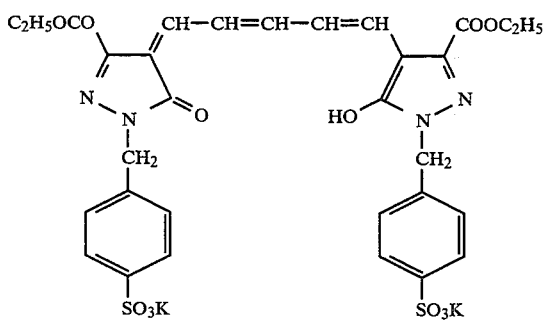 Cpd-21
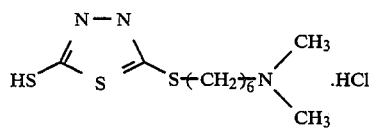 Cpd-22
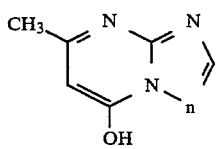 Cpd-23
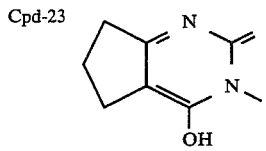 Cpd-24
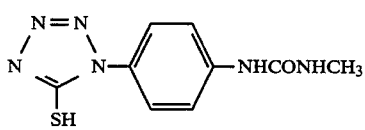 Cpd-25
Cpd-26
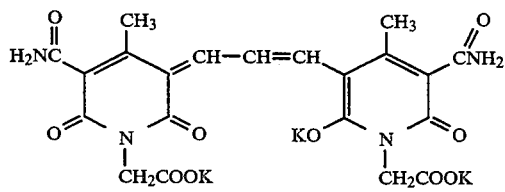 Cpd-27

-continued
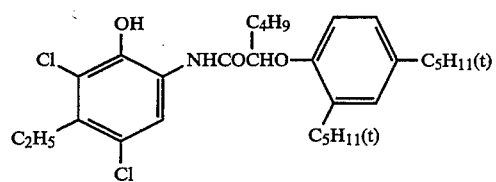
EXC-1
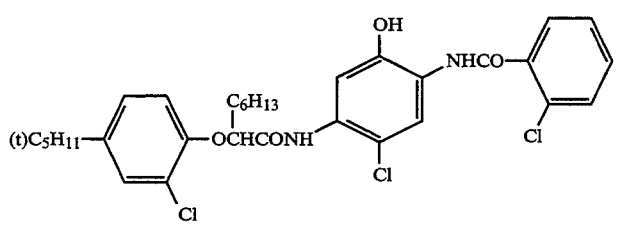
EXC-2
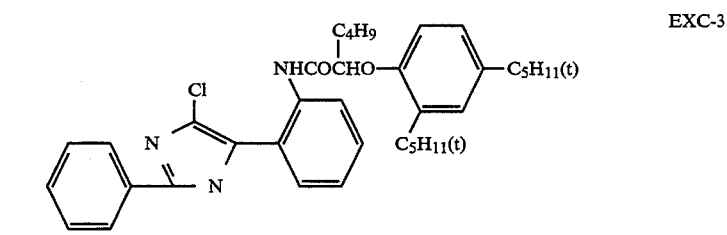
EXC-3
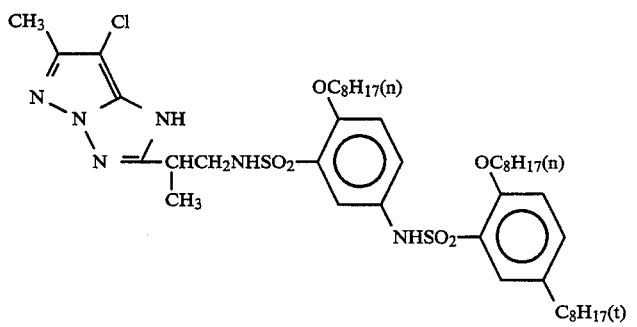
ExM-1
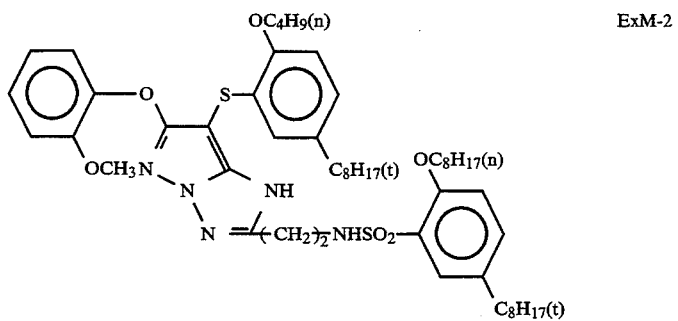
ExM-2
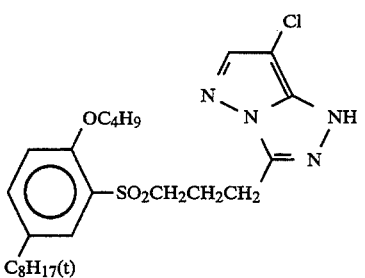
ExM-3
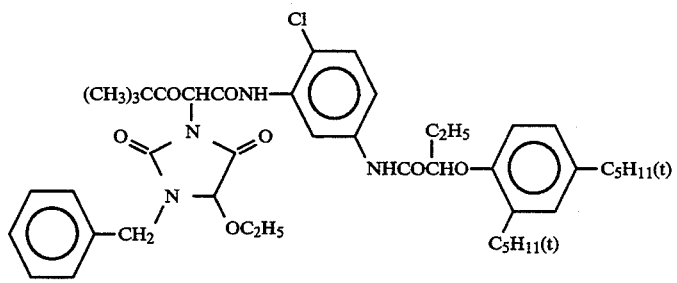
ExY-1

-continued

ExY-2

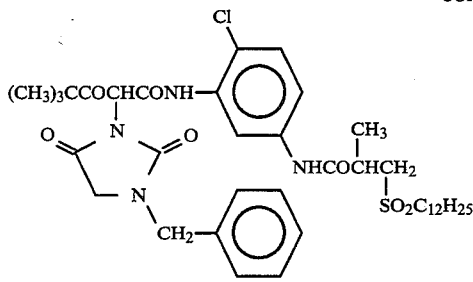

Solv-1: Di(2-ethylhexyl)sebacate
Solv-2: Trinonyl phosphate
Solv-3: Di(3-methylhexyl)phthalate
Solv-4: Tricresyl phophate
Solv-5: Dibutyl phthalate
Solv-6: Trioctyl phosphate
Solv-7: Di(2-ethylhexyl)phthalate
H-1: 1,2-Bis(vinylsulfonylacetoamido)ethane
H-2: 4,6-Dichloro-2-hydroxy-1,3,5-triazine sodium salt
ExZK-1: 7-(3-Ethoxycarbonylaminobenzamido)-9-methyl-10-propargyl-1,2,3,4-tetrahydroacrylginium trifluoromethanesulfonate
ExZK-2: 2-[4-{3-[3-{-[5-{3-[2-chloro-5-(1-dodecyloxycarbonylethoxycarbonyl)phenylcarbamoyl]-4-hydroxylnaphtylthio}tetrazole-1-yl]phenyl-}ureido]benzenesulfonamido}phenyl]-1-formylhydrazine Samples for comparison and samples of the present invention were prepared by replacing Yellow Couplers ExY-1 and ExY-2 in the low-sensitive blue-sensitive layer and high-sensitive blue-sensitive layer with the couplers for comparison or those of this invention.

These Samples were processed and assessed according to the following procedures and processes.

The prepared silver halide color photographic materials were exposed to light image-wise and were processed by an automatic processor in accordance with the following method continuously until the accumulated replenishing amount of the solution reached three times the tank volume.

| Processing Steps | Time | Temperature | Tank Volume | Replenisher Amount |
|---|---|---|---|---|
| Color Development | 135 sec | 38° C. | 15 l | 300 ml/m² |
| Bleach-fixing | 40 sec | 33° C. | 3 l | 300 ml/m² |
| Water washing (1) | 40 sec | 33° C. | 3 l | — |
| Water washing (2) | 40 sec | 33° C. | 3 l | 320 ml/m² |
| Drying | 30 sec | 80° C. | | |

Washing was carried out in a so-called countercurrent mode, in which the overflow solution of the tank of washing (2) was led to the tank of washing (1). The amount of carried over bleach-fixing solution by the photographic material from the bleach-fixing tank to the tank of washing (1) was 35 ml/m² and the magnification of replenishing amount to the carried over amount of bleach-fixing was 9.1.

The composition of each processing solution was as follows:

| Color developer | Mother Solution | Replenisher |
|---|---|---|
| D-Sorbit | 0.15 g | 0.20 g |
| Sodium naphthalenesufonate folmarin adduct | 0.15 g | 0.20 g |
| Ethylenediaminetetrakismethylene phosphonic acid | 1.5 g | 1.5 g |
| Diethylene glycol | 12.0 ml | 16.0 ml |
| Benzyl alcohol | 13.5 ml | 18.0 ml |
| Potassium bromide | 0.80 g | — |
| Benzotriazole | 0.003 g | 0.004 g |
| Sodium sulfite | 2.4 g | 3.2 g |
| N,N-Bis(carboxymethyl)hydrazine | 6.0 g | 8.0 g |
| D-Glucose | 2.0 g | 2.4 g |
| Triethanolamine | 6.0 g | 8.0 g |
| N-Ethyl-N-(β-methanesulfonamidoethyl)-3-methyl-4-aminoaniline sulfate | 6.4 g | 8.5 g |
| Potassium carbonate | 30.0 g | 25.0 g |
| Fluorescent brightening agent (diaminostyrbene series) | 1.0 g | 1.2 g |
| Water to make | 1000 ml | 1000 ml |
| pH (25° C.) | 10.25 | 10.75 |

| Bleach-fixing solution (Mother solution and replenisher are the same) | |
|---|---|
| Disodium ethylenediaminetetraacetate | 4.0 g |
| Iron(III) ammonium ethylenediaminetetraacetate | 70.0 g |
| Ammonium thiosulfate (700 g/l) | 180 ml |
| Sodium p-toluenesulfinate | 20.0 g |
| Sodium bisulfite | 20.0 g |
| 5-Mercapto-1,3,4-triazole | 0.5 g |
| Ammonium nitrate | 10.0 g |
| Water to make | 1000 ml |
| pH (25° C.) | 6.20 |

Water washing solution
(Mother solution and replenisher are the same)

Tap water was treated by passage through a hybrid-type column filled with an H-type strong acidic cation-exchange resin (Amberlite IR-120B, tradename, made by Rohm & Haas) and an OH-type strong alkaline anion-exchange resin (Amberlite IR-400, tradename, made by the same as the above) so as to make the concentrations of calcium ions and magnesium ions 3 mg/l or less. Then 20 mg/l of sodium dichloroisocyanurate and 1.5 g/l of sodium sulfate were added. The pH of the solution was in a range of 6.5 to 7.5.

In this case the same results as in Example 1 were obtained.

EXAMPLE 8

To 9.15 g of comparative coupler (ExY-1) 10.0 g of tricresyl phosphate, as a high-boiling organic solvent, and 20 ml of ethylacetate were added. The mixture was heated to obtain a solution. The solution was added to 250 g of 10% gelatin solution, 1.2 g of dodecylbenzenesulfonic acid was added to the solution, and the mixture was emulsified and dispersed.

To the emulsified dispersion, 75.7 g of silver chlorobromide emulsion (containing 64.9 g/kg of silver, silver bromide: 70 mol %) and 300 g of 10% aqueous gelatin solution and 153 ml of water were added. After adding of 1.0 g of sodium 1-oxy-3,5-dichloro-s-triazinate, as a hardener, Sample 801 was prepared by coating the dispersion on a prime coated triacetyl cellulose base such that the coating amount of coupler would be 1 mmol/m$^2$. In this case, 1.66 g/m$^2$ of gelatin layer was provided on that coated layer, as a protective layer.

Samples 802 to 804 were prepared in the same manner as Sample 801, except that coupler was changed to other comparative couplers and a coupler of the present invention, as shown in Table 6, so as to get an equimolar amount of coated coupler.

The above samples were subjected to an exposure to white light through an optical wedge and then subjected to the processing shown below.

| Processing Process | Temperature | Time |
|---|---|---|
| Color development | 35° C. | 120 sec. |
| Bleach-fixing | 33° C. | 90 sec. |
| Water washing | 30–35° C. | 120 sec. |
| Drying | 80° C. | |

The composition of each processing solution was as follows:

| Color developer | |
|---|---|
| Water | 700 ml |
| Ethylenediaminetetraacetic acid | 3.0 g |
| Disodium-1,2-dihydroxybenzen-4,6-disulfonate | 4.0 g |
| Triethanolamine | 12.0 g |
| Potassium bromide | 1.5 g |
| Potassium carbonate | 27.0 g |
| Fluorescent whitening agent (WHITEX 4B, manufactured by Sumitomo Chem. Co.) | 1.0 g |
| Sodium sulfite | 0.1 g |
| Disodium-N,N-bis(sulfonatoethyl)-3-hydroxylamine | 10.0 g |
| N-Ethyl-N-(β-methanesulfonamidoethyl)-3-methyl-4-aminoaniline sulfonate- | 5.0 g |
| Water to make | 1000 ml |
| pH (25° C.) | 10.05 |
| Bleach-fixing solution | |
| Water | 600 g |
| Ammonium thiosulfate (700 g/l) | 100 ml |
| Iron(III) ammonium ethylenediamine-tetraacetate | 55.0 g |
| Ethylendiaminetetraacetic acid | 5.0 g |
| Ammonium bromide | 40.0 g |
| Nitric acid (67%) | 30.0 g |
| Water to make | 1000 ml |
| pH (25° C.)(adjusted by acetic acid and aqueous ammonia) | 5.8 |

Yellow couplers for comparison are as follows:

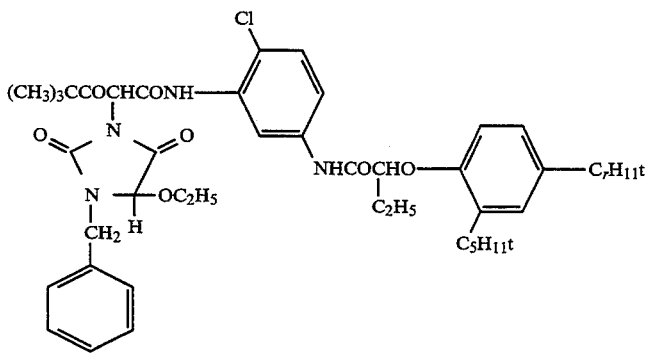

ExY-1

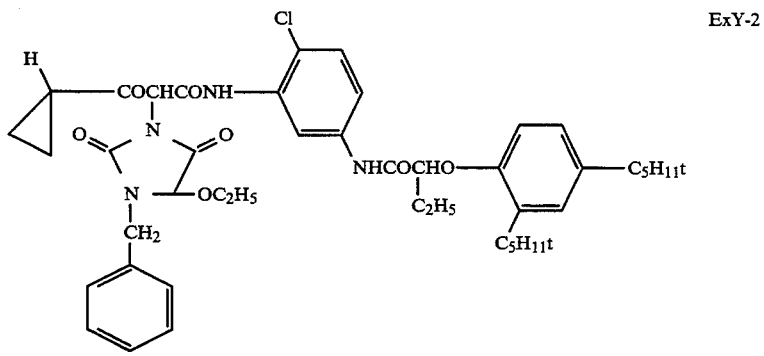

ExY-2

ExY-3

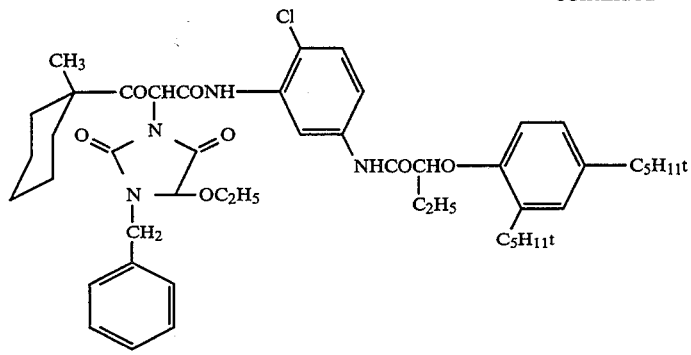

Thus processed samples were measured the density of colored yellow and the maximum color density Dmax are shown in Table 6.

TABLE 6

| Sample | Coupler | Dmax | Remarks |
| --- | --- | --- | --- |
| 801 | ExY-1 | 1.46 | Comparative Example |
| 802 | ExY-2 | 1.60 | " |
| 803 | ExY-3 | 1.39 | " |
| 804 | Y-1 | 1.90 | This Invention |

Figure 2:
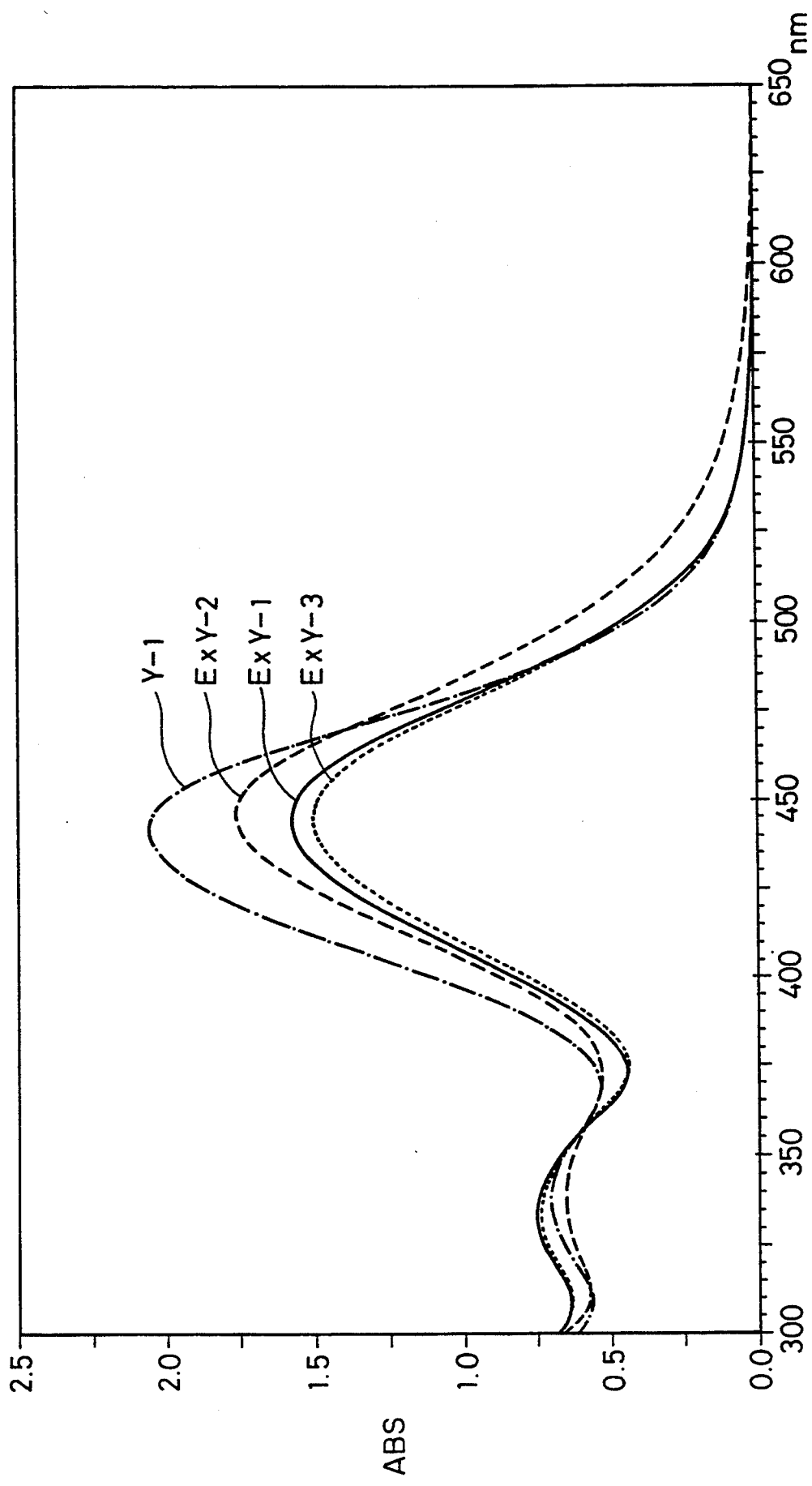
FIG. 2 is a diagram of the absorption spectra of other dyes, wherein the absorbence is plotted in the same manner as in FIG. 1.

The absorption spectra of each sample above-described was measured and the results are shown in FIG. 2.

As is apparent form the results in Table 6, it can be noticed that coupler Y-1 of the present invention give a higher density than those of comparative couplers.

Further, as is apparent from FIG. 2, comparative coupler ExY-2 having a cyclopropane ring in the molecular similarly to the coupler of the present invention has apparently unpreferable absorption at long wavelength side, although it spectral characteristics shows a little increased absorbance. On the other hand, comparative coupler ExY-3 of cyclohexyl ring structure having a methyl group on 1-position is nearly similar to the comparative coupler ExY-1 that is pivaloyl-type coupler in the spectral characteristics and its absorbance is rather reduced.

On the contrary, it can be noticed that, in the case of coupler Y-1 of the present invention, not only the absorbance increases remarkably, but also the absorption at long wavelength side is improved remarkably in the sharpness of down curve. It was quit unexpected that the coupler Y-1 of the present invention would have such an excellent property as shown FIG. 2 even by an analogy from known coupler ExY-2 and ExY-3.

EXAMPLE 9

A multilayer photographic material (901) was prepared by multi-coatings composed of the following layer composition on a paper support which has been both sides polyethylene laminated and subjected to a corona discharge treatment followed by providing a subbing layer coated by gelatin containing sodium dodecylbenzenesulfonate. Coating solutions were prepared as follows:

Preparation of the First Layer Coating Solution

To a mixture of 15.4 g of yellow coupler (ExY-1), 4.8 g of image-dye stabilizer (Cpd-1) 1.3 g of image-dye stabilizer (Cpd-7), 1.3 g of image dye stabilizer (Cpd-9), and 0.3 g of stabilizer (Cpd-12), 25.0 ml of ethyl acetate and each 3.8 g of solvents (Solv-3) and (Solv-7) were added and dissolved. The resulting solution was dispersed and emulsified in 185 ml of 10% aqueous gelatin solution containing 8 ml of sodium dodecylbenzenesulfonate to obtain emulsified dispersion A. Separately silver chlorobromide emulsion A (cubic grains, 3:7 (silver mol ratio) blend of grains having a 0.88 μm and a 0.7 μm average grain size, and a 0.08 and a 0.10 deviation coefficient of grain size distribution, respectively, each in which 0.3 mol % of silver bromide was located at the surface of grains) was prepared. To this emulsion two kinds of blue-sensitive sensitizing dye A and B were added in such amounts that emulsion and $2.5 \times 10^{-4}$ mol to the small size emulsion per mol of silver, and then sulfur-sensitized. The chemical ripening of this emulsion was conducted by adding sulfur sensitizing agent and gold sensitizing agent. The thus-prepared emulsion A and the above-obtained emulsified dispersion A were mixed together and dissolved to give the composition shown below, thereby preparing the first layer coating solution.

Coating solutions for the second to seventh layers were also prepared in the same manner as the first-layer coating solution. As a gelatin hardener for the respective layers, H-1 and H-2 were used.

To each layer Cpd-10 and Cpd-11 were added in such amount that respective total amount would be 25.0 mg/m$^2$ and 50.0 mg/m$^2$.

As spectral-sensitizing dyes for the respective layers, the following compounds were used:

Sensitizing Dye A for Blue-Sensitive Emulsion Layer:

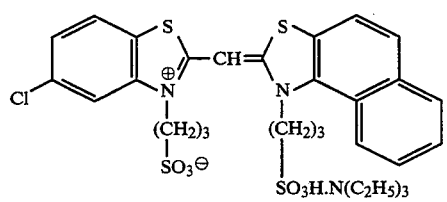

Sensitizing Dye B for Blue-Sensitive Emulsion Layer:

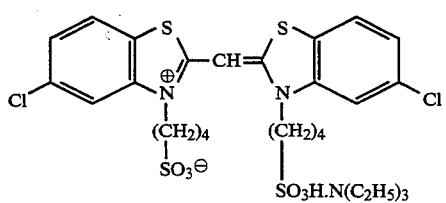

(each $2.0\times10^{-4}$ mol to the large size emulsion and $2.5\times10^{-4}$ mol to the small size emulsion, per mol of silver halide.)

Sensitizing Dye C for Green-Sensitive Emulsion Layer:

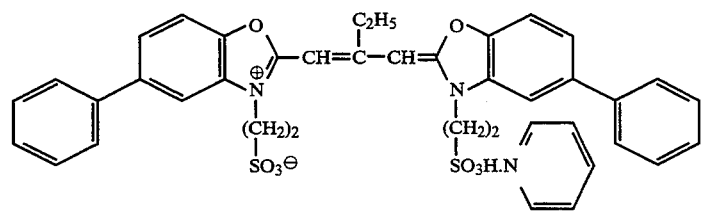

($4.0\times10^{-4}$ mol to the large size emulsion and $5.6\times10^{-4}$ mol to the small size emulsion, per mol of silver halide) and Sensitizing Dye D for Green-Sensitive Emulsion

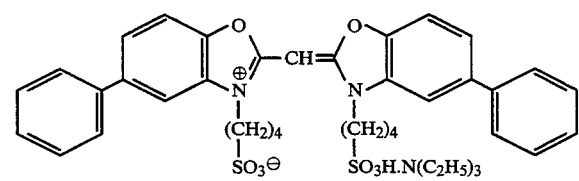

($7.0\times10^{-5}$ mol to the large size emulsion and $1.0\times10^{-5}$ mol to the small size emulsion, per mol of silver halide).

Sensitizing Dye E for Red-Sensitive Emulsion Layer:

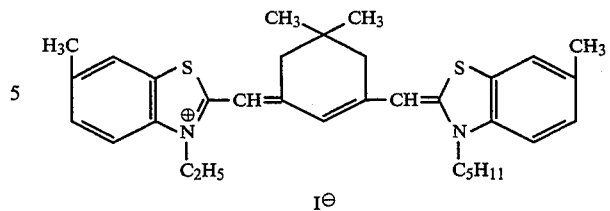

($0.9\times10^{-4}$ mol to the large size emulsion and $1.1\times10^{-4}$ mol to the small size emulsion, per mol of silver halide).

To the red-sensitive emulsion layer, the following compound was added in an amount of $2.6\times10^{-3}$ mol per mol of silver halide:

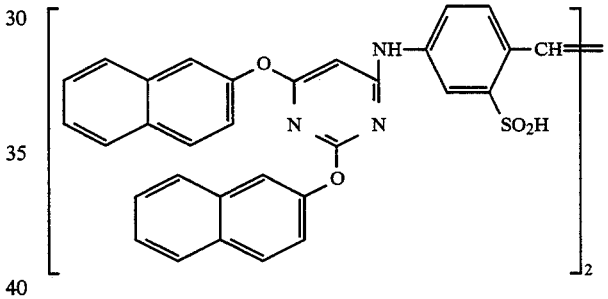

Further, 1-(5-methylureidophenyl)-5-mercaptotetrazole was added to the blue-sensitive emulsion layer, the green-sensitive emulsion layer, and the red-sensitive emulsion layer in amount of $8.5\times10^{-5}$ mol, $7.7\times10^{-4}$ mol, and $2.5\times10^{-4}$ mol, per mol of silver halide respectively.

Further, to the blue-sensitive emulsion layer and the green-sensitive layer 4-hydroxy-6-methyl-1,3,3a,7-tetrazaubdebe was added in amounts of $1\times10^{-4}$ mol and $2\times10^{-4}$ mol per mol of silver halide, respectively.

The following dyes were added to the emulsion were to prevent irradiation. (Figures in parentheses show each coating amount.)

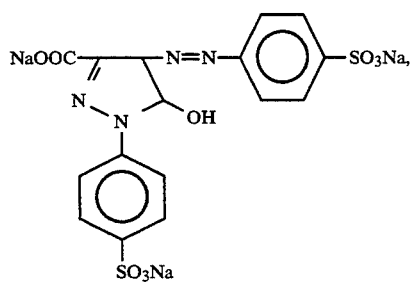

(10 mg/m²)

-continued

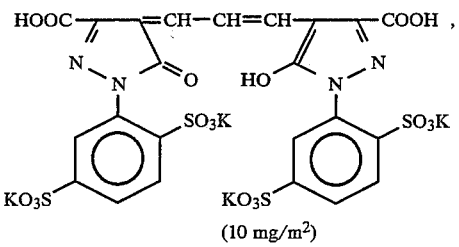

(10 mg/m²)

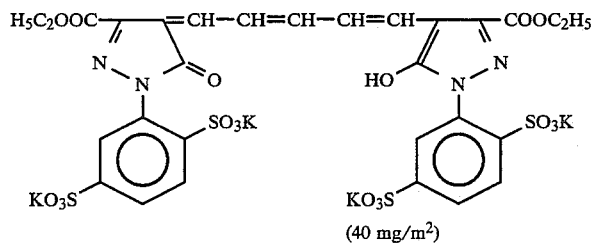

(40 mg/m²)

and

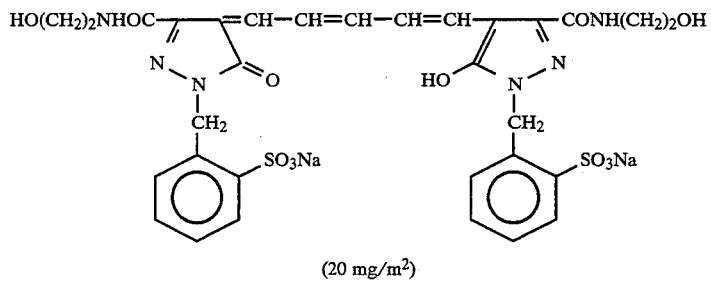

(20 mg/m²)

Composition of Layers

The composition of each layer is shown below. The figures represent coating amount (g/m²). The coating amount of each silver halide emulsion is given in terms of silver.

| Supporting Base | |
|---|---|
| Paper laminated on both sides with polyethylene (a white pigment, TiO₂, and a bluish dye, ultramarine, were included in the first layer side of the polyethylene-laminated film) | |
| First Layer (Blue-sensitive emulsion layer): | |
| The above-described silver chlorobromide emulsion A | 0.26 |
| Gelatin | 1.54 |
| Yellow coupler (ExY-1) | 0.48 |
| Image-dye stabilizer (Cpd-1) | 0.15 |
| Solvent (Solv-3) | 0.12 |
| Solvent (Solv-7) | 0.12 |
| Image-dye stabilizer (Cpd-7) | 0.04 |
| Image-dye stabilizer (Cpd-9) | 0.03 |
| Stabilizer (Cpd-12) | 0.01 |
| Second Layer (Color-mix preventing layer): | |
| Gelatin | 0.99 |
| Color mix inhibitor (Cpd-5) | 0.08 |
| Solvent (Solv-1) | 0.16 |
| Solvent (Solv-4) | 0.08 |
| Third Layer (Green-sensitive emulsion layer): | |
| Silver chlorobromide emulsions (cubic grains, 1:3 (Ag mol ratio) blend of grains having a 0.55 μm and a 0.39 μm average grain size, and a 0.10 and a 0.08 deviation coefficient of grain size distribution, respectively, each in which 0.8 mol % of AgBr was located at the surface of grains) | 0.12 |
| Gelatin | 1.24 |
| Magenta coupler (ExM) | 0.20 |
| Image-dye stabilizer (Cpd-2) | 0.03 |
| Image-dye stabilizer (Cpd-3) | 0.15 |
| Image-dye stabilizer (Cpd-4) | 0.02 |

| -continued | |
|---|---|
| Image-dye stabilizer (Cpd-9) | 0.02 |
| Solvent (Solv-2) | 0.40 |
| Fourth Layer (Ultraviolet absorbing layer): | |
| Gelatin | 1.58 |
| Ultraviolet absorber (UV-1) | 0.47 |
| Color-mix inhibitor (Cpd-5) | 0.05 |
| Solvent (Solv-5) | 0.24 |
| Fifth Layer (Red-sensitive emulsion layer): | |
| Silver chlorobromide emulsions (cubic grains, 1:4 (Ag mol ratio) blend of grains having a 0.58 μm and a 0.45 μm average grain size, and a 0.09 and a 0.11 deviation coefficient of grain size distribution, respectively, each in which 0.6 mol % of AgBr was located at the surface of grains) | 0.23 |
| Gelatin | 1.34 |
| Cyan coupler (ExC) | 0.32 |
| Image-dye stabilizer (Cpd-2) | 0.03 |
| Image-dye stabilizer (Cpd-4) | 0.02 |
| Image-dye stabilizer (Cpd-6) | 0.16 |
| Image-dye stabilizer (Cpd-7) | 0.40 |
| Image-dye stabilizer (Cpd-8) | 0.05 |
| Solvent (Solv-6) | 0.14 |
| Sixth layer (Ultraviolet ray absorbing layer): | |
| Gelatin | 0.53 |
| Ultraviolet absorber (UV-1) | 0.16 |
| Color-mix inhibitor (Cpd-5) | 0.02 |
| Solvent (Solv-5) | 0.08 |
| Seventh layer (Protective layer): | |
| Gelatin | 1.33 |
| Acryl-modified copolymer of polyvinyl alcohol (modification degree: 17%) | 0.17 |
| Liquid paraffin | 0.03 |

Compounds used are as follows:
(ExY) Yellow coupler
ExY-1 The same as in Example 8
ExY-2 The same as in Example 8
ExY-3 The same as in Example 8
(ExM) Magenta coupler

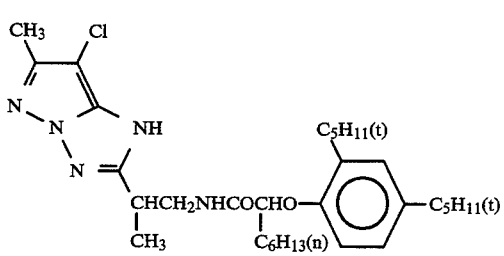

(ExC) Cyan coupler
Mixture (1:1 in weight ratio) of

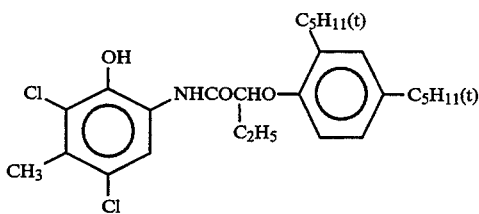

and

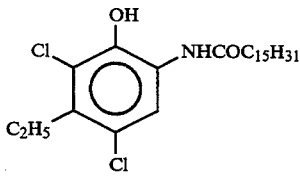

(Cpd-1) Image-dye stabilizer

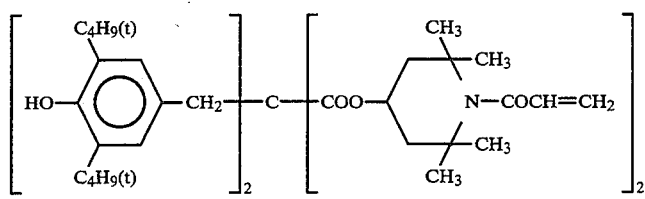
(Cpd-2) Image-dye stabilizer
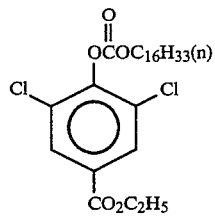
(Cpd-3) Image-dye stabilizer
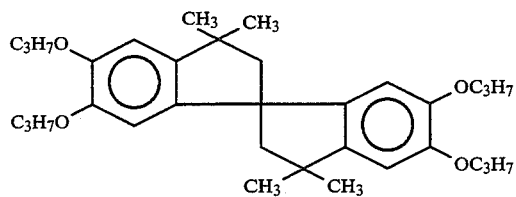
(Cpd-4) Image-dye stabilizer
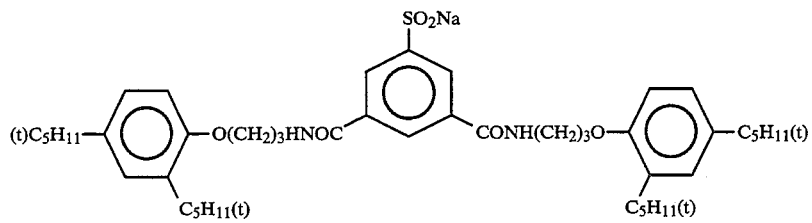
(Cpd-5) Color-mix inhibitor
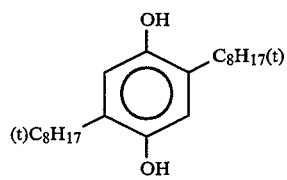
(Cpd-6) Image-dye stabilizer
Mixture (2:4:4 in weight ratio) of
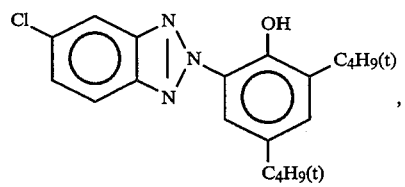,
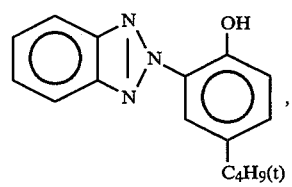,
and

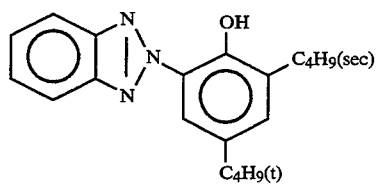
(Cpd-7) Image-dye stabilizer
Average molecular weight: 60,000
(Cpd-8) Image-dye stabilizer
Mixture (1:1 in weight ratio) of
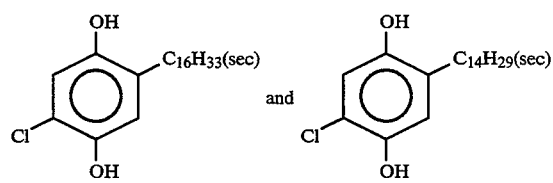
(Cpd-9) Image-dye stabilizer
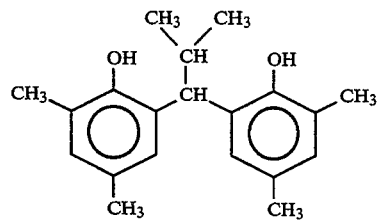
(Cpd-10) Antiseptics
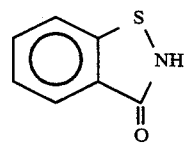
(Cpd-11) Antiseptics
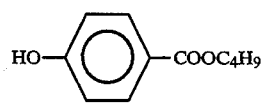
(Cpd-12)
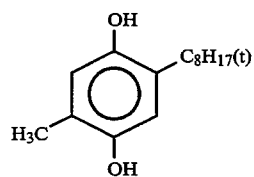
(UV-1) Ultraviolet ray absorber
Mixture (4:2:4 in weight ratio) of -continued
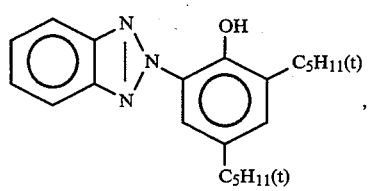,
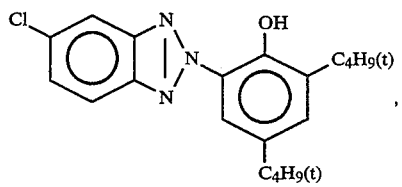,
and
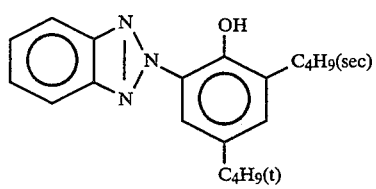
(Solv-1) Solvent
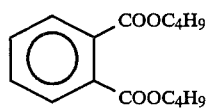
(Solv-2) Solvent
Mixture (1:1 in volume ratio) of
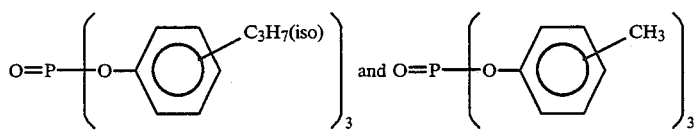
(Solv-3) Solvent
O = P⁅O—C₉H₁₉(iso)]₃
(Solv-4) Solvent
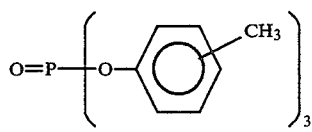
(Solv-5) Solvent
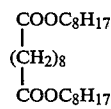
(Solv-6) Solvent
Mixture (80:20 in volume ratio) of
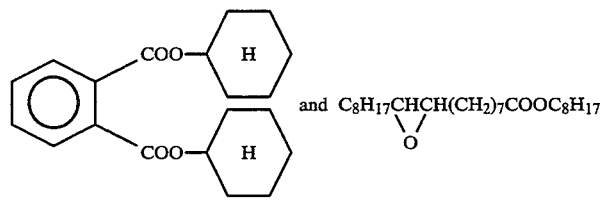

(Solv-7) Solvent

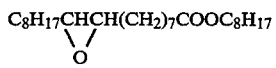

H-1

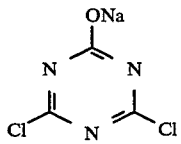

H-2

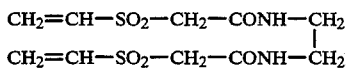

Samples 902 to 913 were prepared in the same manner as sample 901, except that the kind and the coating amount of yellow coupler were changed as shown in Table 7, respectively, provided that the molar ratio of coupler to silver halide in the coating amount was adjusted to be constant (the same as in Sample 901).

Then, these photographic papers were given gradation exposure of a three-color separation filter for sensitometry by using a sensitometer (manufactured by Fuji Photo Film Co., Ltd., FWH model, the color temperature of the source of light being 3200° K.). The exposure was carried out so that the exposure amount would be 250 CMS with an exposure time of 0.1 sec.

After image-wise exposure of the above photographic Materials, they were continuously processed (running test) by using a paper processor in the following processing steps until the replenishing amount reached a point twice the amount of the tank volume for color development.

| Processing steps | Temperature | Time | Replenisher Amount* | Tank Volume |
|---|---|---|---|---|
| Color Developing | 35° C. | 45 sec. | 161 ml | 17 l |
| Bleach-fixing | 30-35° C. | 45 sec. | 215 ml | 17 l |
| Rinsing 1 | 30-35° C. | 20 sec. | — | 10 l |
| Rinsing 2 | 30-35° C. | 20 sec. | — | 10 l |
| Rinsing 3 | 30-35° C. | 20 sec. | 350 ml | 10 l |
| Drying | 70-80° C. | 60 sec. | | |

Note:
*Replenisher amount is shown in ml per $m^2$ of photographic material. Rinsing steps were carried out in 3-tanks counter-flow mode from the tank of rinsing 3 towards the tank of rinsing 1. The opened surface ratio was changed by changing the size of floating lid.

The compositions of each processing solution were as follows:

| | Tank Solution | Replenisher |
|---|---|---|
| Color developer | | |
| Water | 800 ml | 800 ml |
| Ethylenediamine-N,N,N',N'-tetra-methylenephosphonic acid | 1.5 g | 2.0 g |
| Potassium bromide | 0.015 g | — |
| Triethanolamine | 8.0 g | 12.0 g |
| Sodium chloride | 1.4 g | — |
| Potassium carbonate | 25 g | 25 g |
| N-ethyl-N-(β-methanesulfonamidoethyl)-3-methyl-4-aminoaniline sulfonate | 5.0 g | 7.0 g |
| N,N-bis(carboxymethyl)hydrazine | 5.5 g | 7.0 g |
| N,N-di(sulfoethyl)hydroxylamine.1Na | 4.0 g | 5.0 g |
| Fluorescent brightening agent (WHITEX-4, made by Sumitomo Chemical Ind. Co.) | 1.0 g | 2.0 g |
| Water to make | 1000 ml | 1000 m |
| pH (25° C.) | 10.05 | 10.45 |
| Bleach-fixing solution | | |
| (Both tank solution and replenisher) | | |
| Water | 400 ml | |
| Ammonium thiosulfate (70%) | 100 ml | |
| Sodium sulfite | 17 g | |
| Iron (III) ammonium ethylenediamine-tetraacetate dehydrate | 55 g | |
| Disodium ethylenediaminetetraacetate | 5 g | |
| Ammonium bromide | 40 g | |
| Water to make | 1000 ml | |
| pH (25° C.) | 6.0 | |
| Rinsing solution | | |

(Both tank solution and replenisher) Ion-exchanged water
(Calcium and magnesium each are contained in an amount of 3 ppm or below)

The yellow coupler density of thus processed each Samples was measured. The results are shown in Table 7.

TABLE 7

| No. | Coupler | Coating amount (mmol/$m^2$) | Dmax | Remarks |
|---|---|---|---|---|
| 901 | ExY-1 | 0.6 | 2.05 | Comparative Example |
| 902 | ExY-2 | " | 2.14 | " |
| 903 | ExY-3 | " | 1.98 | " |
| 904 | Y-1 | " | 2.45 | This Invention |
| 905 | Y-42 | " | 2.33 | " |
| 906 | Y-43 | " | 2.21 | " |
| 907 | Y-53 | " | 2.44 | " |
| 908 | Y-56 | " | 2.43 | " |
| 909 | ExY-1 | 0.7 | 2.27 | Comparative Example |
| 910 | " | 0.8 | 2.52 | " |
| 911 | " | 0.9 | 2.67 | " |
| 912 | Y-1 | 0.5 | 2.24 | This Invention |
| 913 | " | 0.7 | 2.69 | " |

As is apparent from the results in Table 7, it can be noticed that, in the comparison of samples at the same coating amount, the couplers of the present invention give higher densities than those of known comparative couplers. In particular, couplers Y-1, Y-53 and Y-56 which have preferable structure of the present invention are excellent.

Further, in order to obtain the similar color density to sample 904 which used coupler Y-1 of the present invention by using the comparative coupler ExY-1, it is needed to increase coating amounts of coupler and silver halide emulsion about 1.3 times. Thus the coupler of the present invention is preferable in view of saving resources.

Although comparative coupler ExY-2 gave a little higher color density among comparative couplers, the hue of this sample cannot be said preferable because the hue being orange by visual observation.

Thus, it can be said that the coupler of the present invention is an excellent coupler because it not only gives a high color density but also brings a preferable color reproduction.

Having described our invention as related to the present embodiments, it is our intention that the invention not be limited by any of the details of the description, unless otherwise specified, but rather be construed broadly within its spirit and scope as set out in the accompanying claims.

What we claim is:

1. An acylacetamide yellow photographic coupler represented by formula (Y):

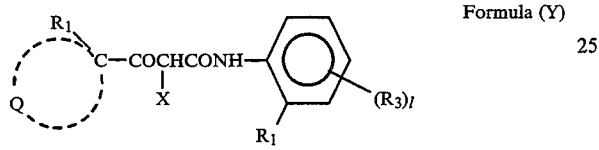

wherein:

$R_1$ is a halogen atom, a cyano group, an unsubstituted or a substituted alkyl group, an unsubstituted or a substituted alkoxy group, an unsubstituted or a substituted aryl group, an unsubstituted or a substituted aryloxy group, benzyl hydroxymethyl, methoxyethyl, ethoxycarbonylmethyl or phenoxyethyl, wherein the substituents, except for the aryl group, are selected from the group consisting of a halogen atom, an alkyl group, an alkoxy group, a nitro group, an amino group, a 1-pyrrolidinyl group, a carbonamido group, a sulfonamido group, an acyl group, and combinations of two or more of said substituents thereof, and the aryl group is selected from the group consisting of phenyl, 1-naphthyl, p-tolyl, o-tolyl, p-chlorophenyl, 4-methoxyphenyl, 8-quinolyl, 4-hexadecyloxyphenyl, pentafluorophenyl, p-hydroxyphenyl, p-cyanophenyl, 3-pentadecylphenyl, 2,4-di-t-pentylphenyl, p-methanesulfonamideophenyl, and 3,4-dichlorophenyl, Q represents a group of non-metallic atoms that forms together with the carbon atom a substituted or unsubstituted 3 to 5 membered cyclic hydrocarbon ring having a total carbon number of 3 to 30 and said Q is selected from the group consisting of:

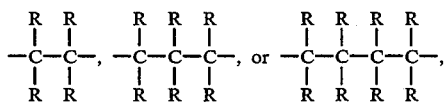

wherein the R groups may be the same or different and represent a halogen atom, a hydrogen atom, or an alkyl group having a carbon number of 1 to 24;

$R_2$ represents a hydrogen atom, a halogen atom, a substituted or unsubstituted alkoxy group, a substituted or unsubstituted aryloxy group, a substituted or unsubstituted alkyl group, or an amino group, wherein the substituents are selected from the group consisting of a halogen atom, an alkyl group, an alkoxy group, an aryloxy group and combinations of two or more of said substituents thereof;

$R_3$ is a halogen atom, an unsubstituted or substituted alkyl group, an unsubstituted or substituted aryl group, an unsubstituted or substituted alkoxy group, an unsubstituted or substituted aryloxy group, an unsubstituted or substituted alkoxycarbonyl group, an unsubstituted or substituted aryloxycarbonyl group, an unsubstituted or substituted carbonamido group, an unsubstituted or substituted sulfonamido group, an unsubstituted or substituted carbamoyl group, an unsubstituted or substituted sulfamoyl group, an unsubstituted or substituted alkylsulfonyl group, an unsubstituted or substituted arylsulfonyl group, an unsubstituted or substituted ureido group, an unsubstituted or substituted sulfamoylamino group, an unsubstituted or substituted alkoxycarbonylamino group, an unsubstituted or substituted alkoxysulfonyl group, a nitro group, an unsubstituted or substituted heterocyclic group, a cyano group, an unsubstituted or substituted acyl group, an unsubstituted or substituted acyloxy group, an unsubstituted or substituted alkylsulfonyloxy group, or an unsubstituted or substituted arylsulfonyloxy group, wherein the substituents are selected from the group consisting of a halogen atom, an alkyl group, an aryl group, a heterocyclic group, an alkoxy group, an aryloxy group, a heterocyclic oxy group, an alkylthio group, an arylthio group, a heterocyclic thio group, an alkylsulfonyl group, an arylsulfonyl group, an acyl group, a carbonamido group, a sulfonamido group, a carbamoyl group, a sulfamoyl group, an alkoxycarbonylamino group, a sulfamoylamino group, a ureido group, a cyano group, a nitro group, an acyloxy group, an alkoxycarbonyl group, an aryloxycarbonyl group, an alkylsulfonyloxy group, an arylsulfonyloxy group and combinations of two or more of said substituents thereof;

X represents a hydrogen atom or a group capable of being released upon a coupling reaction thereof with an oxidized product of an aromatic primary amine developing agent;

l is an integer of 0 to 4, and when l is 2 or more, the $R_3$ groups may be the same or different.

2. The acylacetamide yellow coupler of claim 1, wherein $R_3$ in formula (Y) is selected from the group consisting of a halogen atom, an alkyl group having C-number of 1 to 30, an aryl group having C-number of 6 to 30, an alkoxy group having C-number of 1 to 30, an aryloxy group having C-number of 6 to 30, an alkoxycarbonyl group having C-number of 2 to 30, an aryloxycarbonyl group having C-number of 7 to 30, a carbonamido group having C-number of 1 to 30, a sulfonamido group having C-number of 1 to 30, a carbamoyl group having C-number of 1 to 30, a sulfamoyl group having C-number of 1 to 30, an alkylsulfonyl group having C-number of 1 to 30, a ureido group having C-number of 1 to 30, a sulfamoylamino group having C-number of 0 to 30, an alkoxycarbonylamino group having C-number of 2 to 30, an alkoxysulfonyl group having C-number of 1 to 30, a nitro group, a heterocyclic group having C-number of 1 to 30, a cyano group, an acyl group having C-number of 1 to 30, an acyloxy group having C-number of 2 to 30, an alkylsulfonyloxy group having C-number of 1 to 30, and an arylsulfonyloxy group having C-number of 6 to 30.

3. The acylacetamide yellow coupler of claim 1, wherein the ring formed by Q together with the C is selected from the group consisting of an unsubstituted cyclopropane ring, an unsubstituted cyclobutane ring, and an unsubstituted cyclopentane ring.

4. The acylacetamide yellow coupler of claim 1, wherein X in formula (Y) represents a 5- to 7-membered heterocyclic group bonded to the coupling active site through a nitrogen atom or an aryloxy group.

5. The acylacetamide yellow coupler of claim 1, wherein X in formula (Y) represent a heterocyclic group selected from succinimido, maleinimido, phthalimido, diglycolimido, pyrrole, pyrazole, imidazole, 1,2,4-triazole, tetrazole, indole, indazole, benzimidazole, benztriazole, imidazolidin-2,4-dione, oxazolidin-2,4-dione, thiazolidin-2,4-dione, imidazolidin-2-one, oxazolidin-2-one, thiazolidin-2-one, benzimidazolin-2-one, benzoxazolidin-2-one, benzothiazolin-2-one, 2-pyrrolin-5-one, 2-imidazolin-5-one, indolin-2,3-dione, 2,6-dioxypurine, parabanic acid, 1,2,4-triazolidin-3,5-dione, 2-pyridone, 4-pyridone, 2-pyrimidone, 6-pyridazone-2-pyrazone, 2-amino-1,3,4-thiazolidine, and 2-imino-1,3,4-thiazolidin-4-one.

6. The acylacetamide yellow coupler of claim 1, wherein $R_1$ in formula (Y) is a methyl group.

7. The acylacetamide yellow coupler of claim 1, wherein $R_2$ in formula (Y) represents a chlorine atom.

8. The acylacetamide yellow coupler of claim 1, wherein $R_3$ in formula (Y) represents a halogen atom, an alkoxy group having C-number of 1 to 30, an alkoxycarbonyl group having C-number of 2 to 30, an aryloxycarbonyl group having C-number of 7 to 30, a carbonamido group having C-number of 1 to 30, a sulfonamido group having C-number of 1 to 30, a carbamoyl group having C-number of 1 to 30, or a sulfamoyl group having C-number of 0 to 30.

9. The acylacetamide yellow coupler of claim 1, wherein X is a group represented by the following formula (Y-1) or (Y-2):

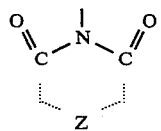

Formula (Y-1)

wherein Z represents

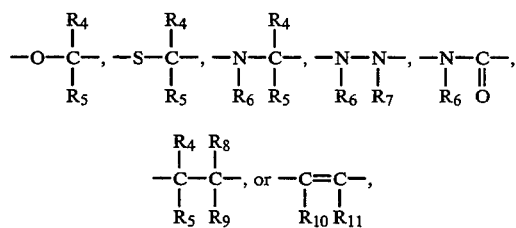

wherein $R_4$, $R_5$, $R_8$, and $R_9$ same or different, each represent a hydrogen atom, an alkyl group, an aryl group, an alkoxy group, an aryloxy group, an alkylthio group, an arylthio group, an alkylsulfonyl group, an arylsulfonyl group, or an amino group; $R_6$ and $R_7$ each represent a hydrogen atom, an alkyl group, an aryl group, an alkylsulfonyl group, an arylsulfonyl group, or an alkoxycarbonyl group; $R_{10}$ and $R_{11}$ each represent a hydrogen atom, an alkyl group, or an aryl group, or $R_{10}$ and $R_{11}$ may bond together to form a benzene ring; and $R_4$ and $R_5$, $R_5$ and $R_6$, $R_6$ and $R_7$, or $R_4$ and $R_8$ may bond together to form a 3- to 8-membered heterocyclic or hydrocarbon ring, which may be substituted;

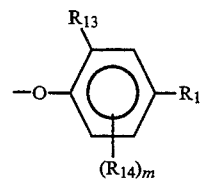

Formula (Y-2)

wherein at least one of $R_{12}$ and $R_{13}$ represents a group selected from a halogen atom, a cyano group, a nitro group, a trifluoromethyl, a carboxyl group, an alkoxycarbonyl group, a carbonamido group, a sulfonamido group, a carbamoyl group, a sulfamoyl group, an alkylsulfonyl group, an arylsulfonyl group, and an acyl group and the other may be a hydrogen atom, an alkyl group, or an alkoxy group; $R_{14}$ has the same meaning as that of $R_{12}$ or $R_{13}$, and m is an integer of 0 to 2.

10. The acylacetamide yellow coupler of claim 1, wherein $R_1$ is a halogen atom, a cyano group, an alkyl group having 1 to 30 carbon atoms, an alkoxy group having 1 to 30 carbon atoms, an aryl group having 6 to 30 carbon atoms, an aryloxy group having 6 to 30 carbon atoms, hydroxymethyl, methoxyethyl, ethoxycarbonylmethyl or phenoxyethyl.

11. The acylacetamide yellow coupler of claim 1, wherein the

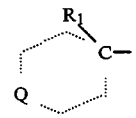

group formed by $R_1$ and Q with C are selected from the group consisting of:

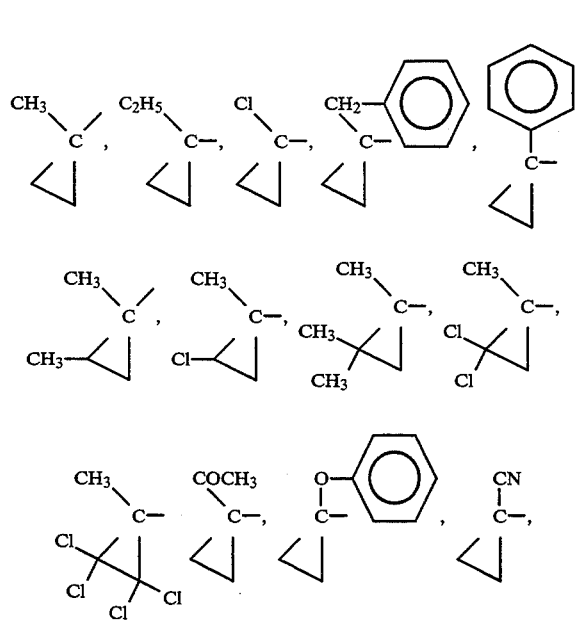

-continued

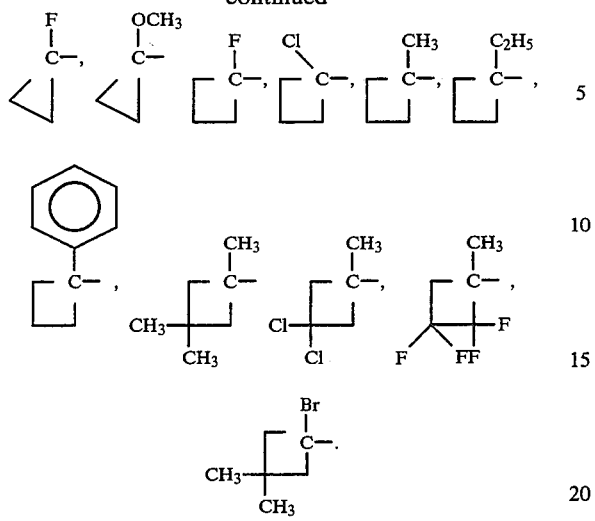

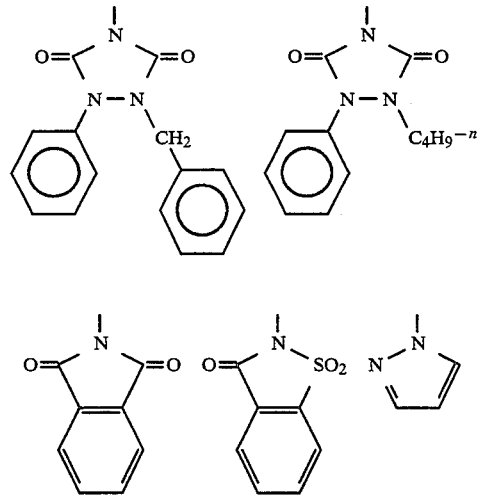

12. The acylacetamide yellow coupler of claim 1, wherein X represents a hydrogen atom or a 3 to 8 heterocyclic ring containing group that contains at least one heteroatom selected from the group consisting of O, N, S, P, Se and Te and is bonded to the coupling site through a nitrogen atom or an aryloxy group and contains from 2 to 36 carbon atoms and is capable of being released upon a coupling reaction thereof with an oxidizing product of an aromatic primary amine developing agent.

13. The acylacetamide yellow coupler of claim 1, where X is selected from the group consisting of:

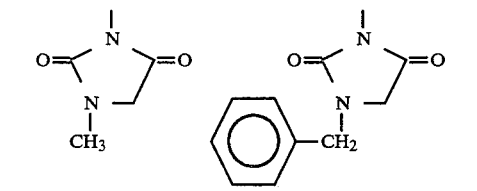

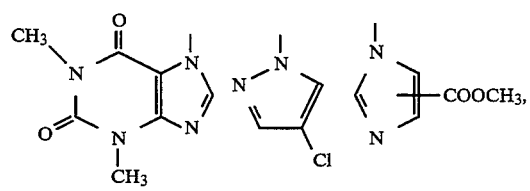

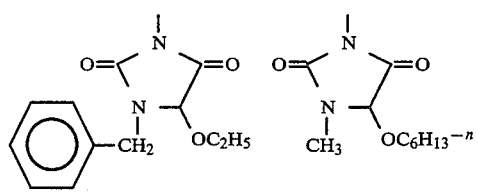

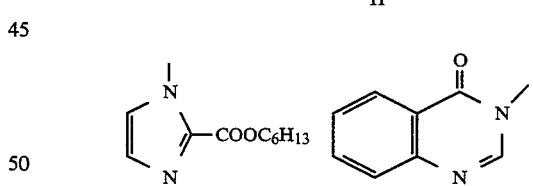

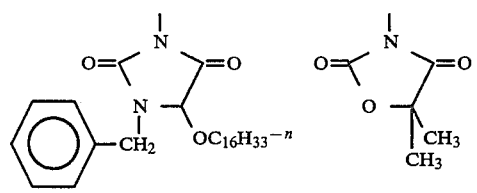

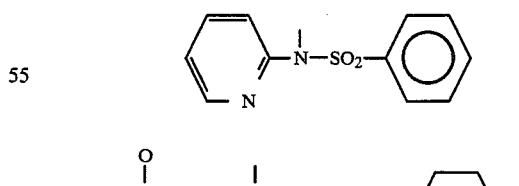

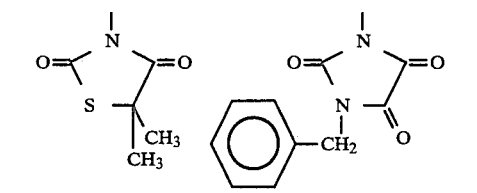

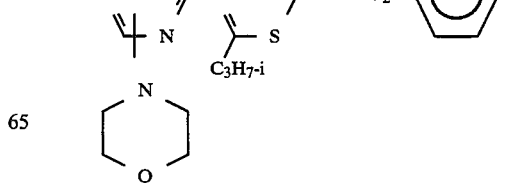

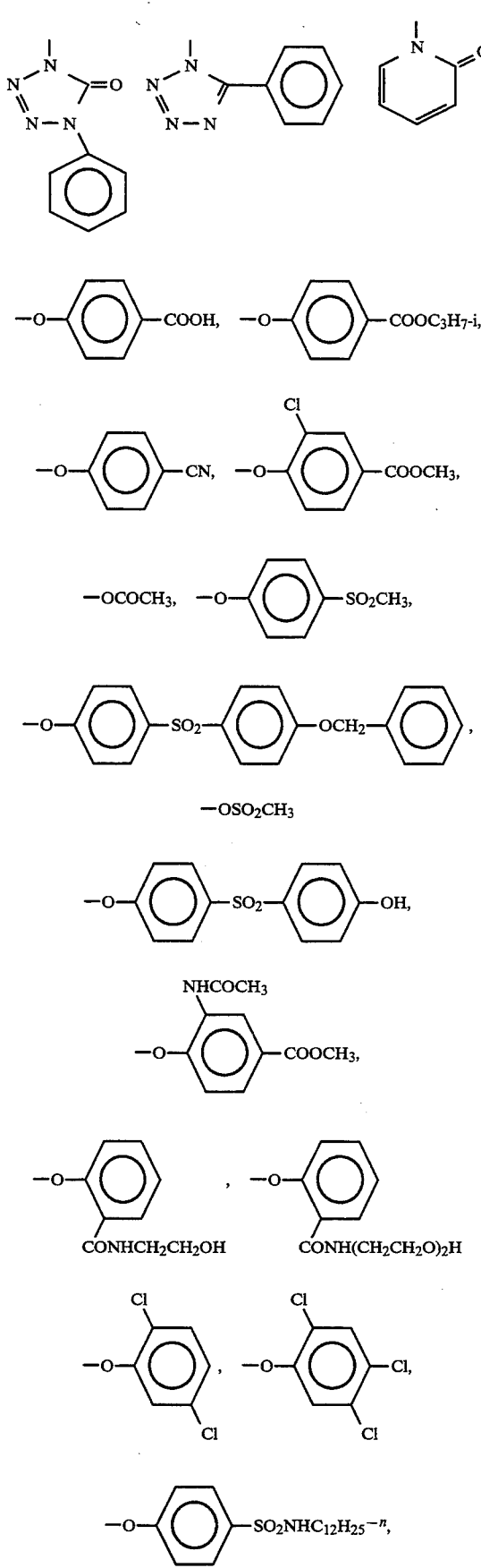

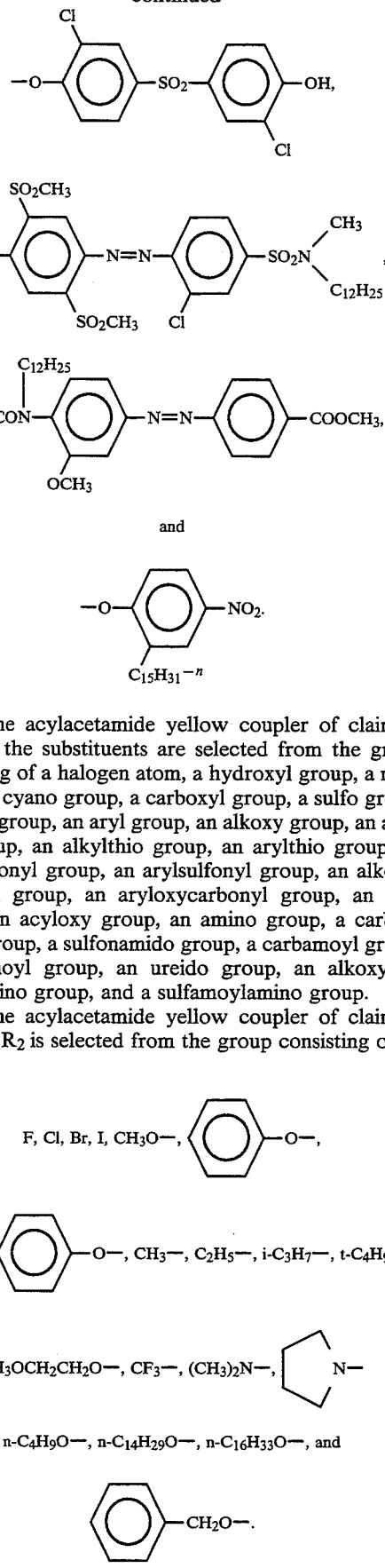

14. The acylacetamide yellow coupler of claim 5, wherein the substituents are selected from the group consisting of a halogen atom, a hydroxyl group, a nitro group, a cyano group, a carboxyl group, a sulfo group, an alkyl group, an aryl group, an alkoxy group, an aryloxy group, an alkylthio group, an arylthio group, an alkylsulfonyl group, an arylsulfonyl group, an alkoxycarbonyl group, an aryloxycarbonyl group, an acyl group, an acyloxy group, an amino group, a carbonamido group, a sulfonamido group, a carbamoyl group, a sulfamoyl group, an ureido group, an alkoxycarbonylamino group, and a sulfamoylamino group.

15. The acylacetamide yellow coupler of claim 1, wherein $R_2$ is selected from the group consisting of:

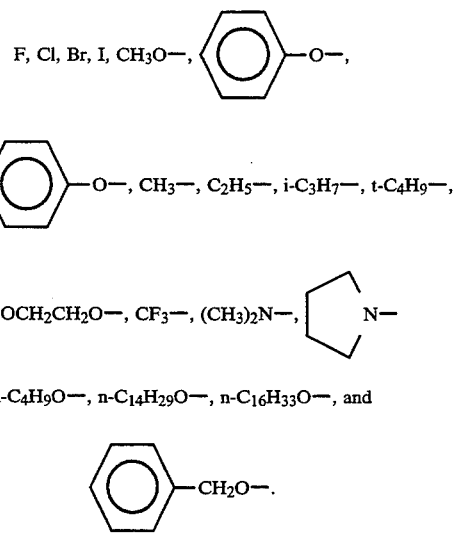

16. The acylacetamido yellow coupler of claim 1, wherein $R_2$ represents a halogen atom, an alkoxy group that may be substituted and has a total of 1 to 30 carbon atoms, an aryloxy group that may be substituted and has a total of 6 to 30 carbon atoms, an alkyl group that may be substituted and has a total of 1 to 30 carbon atoms or an amino group that may be substituted and has a total of 0 to 30 carbon atoms, wherein the substituents of the alkoxy group, aryloxy group, alkyl group and amino group is selected from the group consisting of a halogen atom, an alkyl group, an alkoxy group and an aryloxy group.

17. The acylactamine yellow coupler of claim 16, wherein $R_2$ represents a chlorine atom, a fluorine atom, a substituted or unsubstituted alkyl group having 1 to 6 carbon atoms exclusive of its substituents, an alkoxy group having 1 to 8 carbon atoms, or an aryloxy group having 6 to 24 carbon atoms.

18. The acylactamide yellow coupler of claim 1, wherein $R_3$ represents a halogen atom, an alkoxy group, an alkoxycarbonyl group, an aryloxycarbonyl group, a carbonamido group, a sulfonamido group, a carbamoyl group, or a sulfamoyl group.

19. The acylactamide yellow coupler of claim 1, wherein $R_3$ is selected from the group consisting of:

F, Cl, Br, I, $CH_3O-$, $C_2H_5O-$, n-$C_{12}H_{25}O-$,
$CH_3$, t-$C_4H_9-$, $-COOCH_3$, $COOC_2H_5$,
$-COOC_4H_9^{-n}$, $-COOC_{12}H_{25}^{-n}$, $$-COO\underset{CH_3}{\overset{|}{C}H}COOC_{12}H_{25}, \quad -COO\underset{C_4H_9^{-n}}{\overset{|}{C}H}COOC_{12}H_{29},$$

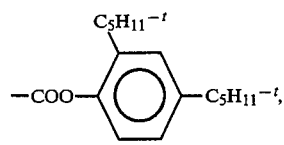

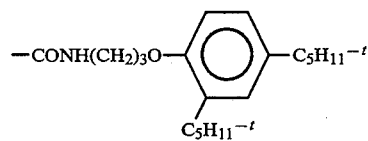

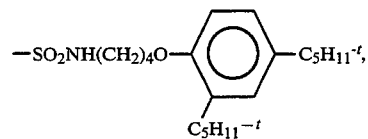

$$-SO_2N\begin{matrix}\diagup CH_3\\ \diagdown CH_3\end{matrix}, \quad -SO_2NHCOC_2H_5, \quad -SO_2NHC_{16}H_{33}^{-n},$$

$-NHCOC_{13}H_{27}^{-n}$, $-NHCOC_{15}H_{31}^{-n}$, $-NHCOC_{17}H_{35}^{-n}$

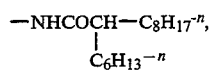

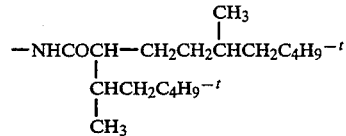

-continued
$$-NHCO\underset{CH_3}{\overset{|}{C}H}CH_2SO_2C_{16}H_{33}^{-n}$$

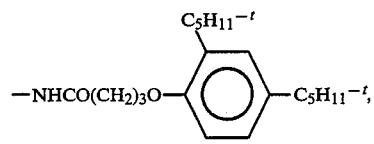

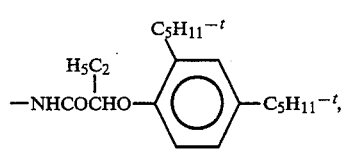

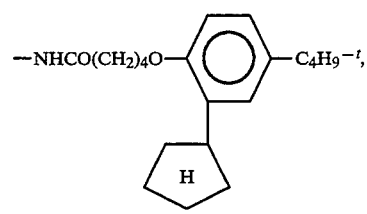

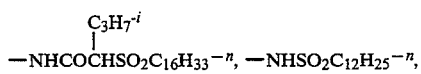

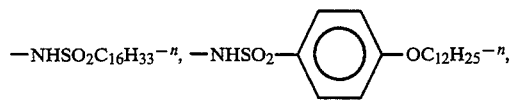

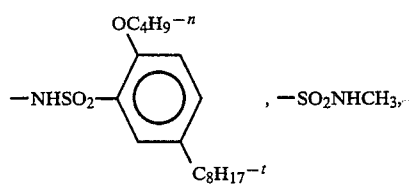

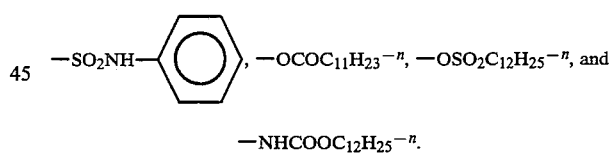

$-NHCOOC_{12}H_{25}^{-n}$.

20. The acylactamide yellow coupler of claim 1, wherein l is an integer of 1 or 2 and the position of the substitution of $R_3$ is the meta-position or ortho-position relative to

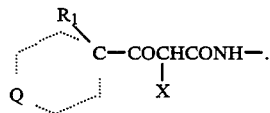

21. The acylacetamide yellow coupler of claim 9, wherein the total number of carbon atoms of the heterocyclic group represented by formula (Y-1) is 2 to 30.

22. The acylacetamide yellow coupler of claim 9, wherein the total number of carbon atoms of the aryloxy group represented by formula (Y-2) is 6 to 30.

23. The acylacetamide yellow coupler of claim 9, wherein the heterocyclic groups represented by formula (Y-1) are heterocyclic groups wherein Z represents $$-O-\underset{R_5}{\overset{R_4}{\underset{|}{C}}}-, \quad -N-\underset{R_5}{\overset{R_4}{\underset{|}{C}}}-, \text{ or } -N-N-,$$

and $R_4$, $R_5$, $R_6$ and $R_7$, are the same or different and are as defined above.

24. The acylacetamide yellow coupler of claim 1, wherein $R_1$ represents an unsubstituted or substituted alkyl group, an unsubstituted or a substituted benzyl group, an unsubstituted or a substituted cycloalkyl group, or an unsubstituted or a substituted aryl group.

25. The acylacetamide yellow coupler of claim 1, wherein $R_1$ represents an unsubstituted or a substituted alkyl group, or an unsubstituted or a substituted benzyl group.

26. The acylacetamide yellow coupler of claim 1, wherein $R_1$ represents a methyl group, an ethyl group, an n-propyl group, an n-butyl group, an isobutyl group or a benzyl group.

27. The acylacetamide yellow coupler of claim 1, wherein $R_1$ represents a methyl group, an ethyl group, or a benzyl group.

28. The acylacetamide yellow coupler of claim 1, wherein Q represents $$-\underset{R}{\overset{R}{\underset{|}{C}}}-\underset{R}{\overset{R}{\underset{|}{C}}}- \text{ or } -\underset{R}{\overset{R}{\underset{|}{C}}}-\underset{R}{\overset{R}{\underset{|}{C}}}-\underset{R}{\overset{R}{\underset{|}{C}}}-,$$

wherein the R groups may be the same or different and represent a halogen atom, a hydrogen atom, or an alkyl group having a carbon number of 1 to 24.

29. The acylacetamide yellow coupler of claim 1, wherein Q represents $$-\underset{R}{\overset{R}{\underset{|}{C}}}-\underset{R}{\overset{R}{\underset{|}{C}}}-,$$

wherein the R groups may be the same or different and represent a halogen atom, a hydrogen atom, or an alkyl group having a carbon number of 1 to 24.

30. The acylacetamide yellow coupler of claim 1, wherein

[structure with $R_1$, C, Q]

represents

[CH$_3$ cyclopropyl structure], [C$_2$H$_5$ cyclopropyl structure], or [CH$_2$-phenyl cyclopropyl structure].

31. The acylacetamide yellow coupler of claim 25, wherein Q represents $$-\underset{R}{\overset{R}{\underset{|}{C}}}-\underset{R}{\overset{R}{\underset{|}{C}}}-,$$

wherein the R groups may be the same or different and represent a halogen atom, a hydrogen atom, or an alkyl group having a carbon number of 1 to 24.

32. The acylacetamide yellow coupler of claim 25, wherein $R_3$ represents a halogen atom, an alkoxy group, an alkoxycarbonyl group, an aryloxycarbonyl group, a carbonamido group, a sulfonamido group, a carbamoyl group, or a sulfamoyl group.

33. The acylacetamide yellow coupler of claim 25, wherein $R_2$ is selected from the group consisting of:

F, Cl, Br, I, CH$_3$O—, [phenyl-O—],

CH$_3$O—[phenyl]—O—, CH$_3$—, C$_2$H$_5$—, i-C$_3$H$_7$—, t-C$_4$H$_9$—,

CH$_3$OCH$_2$CH$_2$O—, CF$_3$—, (CH$_3$)$_2$N—, [pyrrolidinyl N—]

n-C$_4$H$_9$O—, n-C$_{14}$H$_{29}$O—, n-C$_{16}$H$_{33}$O—, and

[phenyl]—CH$_2$O—.

34. The acylacetamide yellow coupler of claim 25, wherein $R_3$ represents a halogen atom, an alkoxy group, an alkoxycarbonyl group, an aryloxycarbonyl group, a carbonamido group, a sulfonamido group, a carbamoyl group, or a sulfamoyl group.

35. The acylacetamide yellow coupler of claim 25, wherein X is a group represented by the following formula (Y-1) or (Y-2):

Formula (Y-1)

$$\underset{C}{\overset{O}{\|}}-N-\underset{C}{\overset{O}{\|}}$$
$$\qquad Z$$

wherein Z represents $$-O-\underset{R_5}{\overset{R_4}{\underset{|}{C}}}-, -S-\underset{R_5}{\overset{R_4}{\underset{|}{C}}}-, -N-\underset{R_5}{\overset{R_4}{\underset{|}{C}}}-, -N-N-,$$

$$-N-\underset{R_6}{\overset{R_4}{\underset{\|}{C}}}-, -\underset{R_5}{\overset{R_4}{\underset{|}{C}}}-\underset{R_9}{\overset{R_8}{\underset{|}{C}}}-, \text{ or } -\underset{R_{10}}{\overset{}{\underset{|}{C}}}=\underset{R_{11}}{\overset{}{\underset{|}{C}}}-,$$

wherein $R_4$, $R_5$, $R_8$, and $R_9$ are the same or different, and each represents a hydrogen atom, an alkyl group, an aryl group, an alkoxy group, an aryloxy group, an alkylthio group, an arylthio group, an alkylsulfonyl group, an arylsulfonyl group, or an amino group; $R_6$ and $R_7$ each represent a hydrogen atom, an alkyl group, an aryl group, an alkylsulfonyl group, an arylsulfonyl group, or an alkoxycarbonyl group; $R_{10}$ and $R_{11}$ each represent a hydrogen atom, an alkyl group, or an aryl group, or $R_{10}$ and $R_{11}$ may bond together to form a benzene ring; and $R_4$ and $R_5$, $R_5$ and $R_6$, $R_6$ and $R_7$, or $R_4$ and $R_8$ may bond together to form a 3- to 5-membered heterocyclic or hydrocarbon ring, which may be substituted:

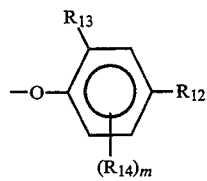

wherein at least one of $R_{12}$ and $R_{13}$ represents a group selected from a halogen atom, a cyano group, a nitro group, a trifluoromethyl, a carboxyl group, an alkoxycarbonyl group, a carbonamido group, a sulfonamido group, a carbamoyl group, a sulfamoyl group, an alkylsulfonyl group, an arylsulfonyl group, and an acyl group and the other may be a hydrogen atom, an alkyl group, or an alkoxy group; $R_{14}$ has the same meaning as that of $R_{12}$ or $R_{13}$, and m is an integer of 0 to 2.

36. The acylacetamide yellow coupler of claim 1, wherein $R_1$ is ethyl.

37. The acylacetamide yellow coupler of claim 1, wherein said coupler has the following formula:

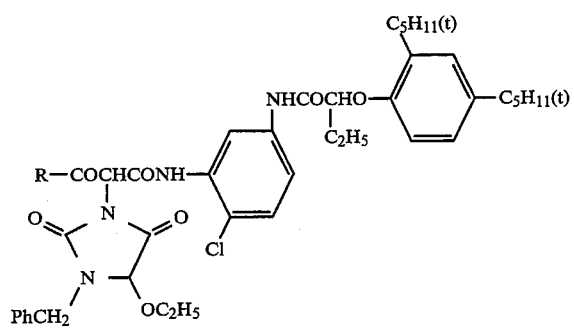

wherein R is

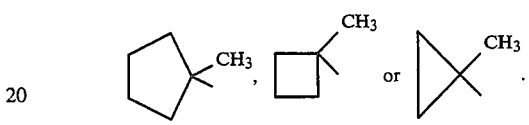

38. The acylacetamide yellow coupler of claim 1, wherein said coupler has the following formula:

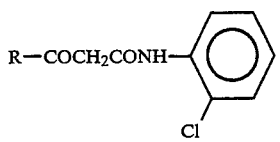

wherein R is

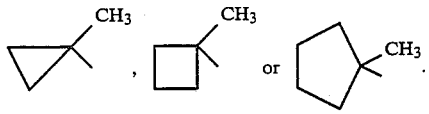

39. The acylacetamide yellow coupler of claim 1, wherein said acylacetamide-type yellow coupler has the following formula:

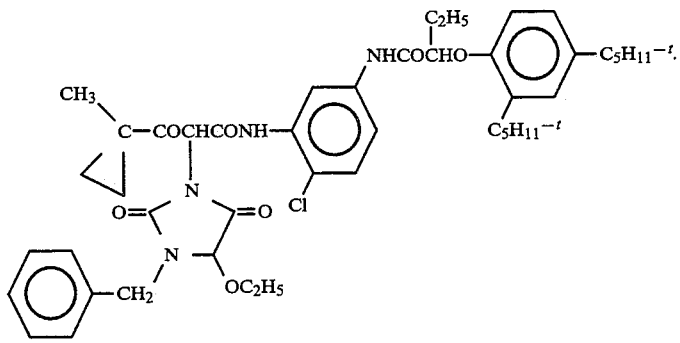

* * * * *